US010004898B2

(12) United States Patent
Ahmed et al.

(10) Patent No.: US 10,004,898 B2
(45) Date of Patent: Jun. 26, 2018

(54) DIPOLE ELECTRICAL STIMULATION EMPLOYING DIRECT CURRENT FOR RECOVERY FROM SPINAL CORD INJURY

(71) Applicants: Zaghloul Ahmed, Staten Island, NY (US); Andrzej Wieraszko, Princeton, NJ (US)

(72) Inventors: Zaghloul Ahmed, Staten Island, NY (US); Andrzej Wieraszko, Princeton, NJ (US)

(73) Assignee: THE RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 0 days. days.

(21) Appl. No.: 15/163,955

(22) Filed: May 25, 2016

(65) Prior Publication Data

US 2016/0263381 A1  Sep. 15, 2016

Related U.S. Application Data

(63) Continuation of application No. 13/503,216, filed as application No. PCT/US2010/053720 on Oct. 22, 2010.

(Continued)

(51) Int. Cl.
*A61N 1/36* (2006.01)
*A61N 1/20* (2006.01)
*A61N 1/05* (2006.01)

(52) U.S. Cl.
CPC ........... *A61N 1/205* (2013.01); *A61N 1/0551* (2013.01); *A61N 1/36003* (2013.01);

(Continued)

(58) Field of Classification Search
CPC ........... A61N 1/36003; A61N 1/36067; A61N 1/36103; A61N 1/36175; A61N 1/36157; A61N 1/36171; A61N 1/36153

(Continued)

(56) References Cited

U.S. PATENT DOCUMENTS 5,047,005 A 9/1991 Cadwell
5,450,859 A 9/1995 Litovitz (Continued)

FOREIGN PATENT DOCUMENTS

WO 2011119251 A2 9/2011

OTHER PUBLICATIONS

International Search Report dated Aug. 2, 2011 for PCT/US10/53720.

(Continued)

*Primary Examiner* — Alyssa M Alter
(74) *Attorney, Agent, or Firm* — Burns & Levinson LLP; Orlando Lopez

(57) ABSTRACT

A system and method to treat neuromuscular conditions, including spinal cord injury, by what is characterized as dipole (two point) cortico-muscular stimulation. Two-point stimulation, with oppositely charged electrodes, allows pulsed, direct current to pass through the cortico-muscular pathway. The electrodes are placed on nerves, muscles, or a combination of both, that are on opposite sides of the spinal column, forming a current that passes across the spinal column. Further, an active electrode can be placed on the spinal column and a reference electrode can be placed outside the central nervous system. These methods improve functional recovery of the motor pathway.

11 Claims, 34 Drawing Sheets

Related U.S. Application Data

(60) Provisional application No. 61/316,319, filed on Mar. 22, 2010, provisional application No. 61/253,948, filed on Oct. 22, 2009.

(52) U.S. Cl.
CPC ..... *A61N 1/36067* (2013.01); *A61N 1/36071* (2013.01); *A61N 1/36082* (2013.01); *A61N 1/36096* (2013.01); *A61N 1/36103* (2013.01); *A61N 1/36153* (2013.01); *A61N 1/36171* (2013.01); *A61N 1/36175* (2013.01); *A61N 1/36157* (2013.01)

(58) Field of Classification Search
USPC .................................... 607/45, 117
See application file for complete search history.

(56) References Cited

U.S. PATENT DOCUMENTS

| | | |
|---|---|---|
| 5,562,718 A | 10/1996 | Palermo |
| 5,738,625 A | 4/1998 | Gluck |
| 7,160,241 B1 | 1/2007 | Herbst |
| 7,660,631 B2 | 2/2010 | Whitehurst et al. |
| 2002/0161415 A1 | 10/2002 | Cohen et al. |
| 2003/0171640 A1 | 9/2003 | Canedo |
| 2003/0217754 A1 | 11/2003 | Thomas et al. |
| 2004/0172097 A1 | 9/2004 | Brodard et al. |
| 2005/0137648 A1 | 6/2005 | Cosendai et al. |
| 2006/0052657 A9 | 3/2006 | Zabara |
| 2006/0116720 A1 | 6/2006 | Knoblich |
| 2008/0004484 A1 | 1/2008 | Wieraszko et al. |
| 2008/0208287 A1* | 8/2008 | Palermo ............... A61N 1/0452 607/48 |
| 2009/0204175 A1 | 8/2009 | Zanella et al. |

OTHER PUBLICATIONS

Laycock, D.C., Pulse Magnetic Field Therapy and the Physiotherapist, http://www.lgselectronics.com.au/physio.html, Jul. 1997.

Agrawal, S. K. et al. Mechanisms of Secondary Injury to Spinal Cord Axons In Vitro: Role of Na+, Na+-K-ATPase, the Na+-H+ Exchanger, and the Na+=Ca2+ Exchanger, J. Neuroscience, 16(2): 545-552, 1996.

Wieraszko, A. Dantrolene Modulates the Influence of Steady Magnetic Fields on Hippocampal Evoked Potentials in Vitro, Bioelectromagnetics 21 :175-182, 2000.

* cited by examiner

FIG. 1B

Normal

Normal

SCI

Lesion Epicentre

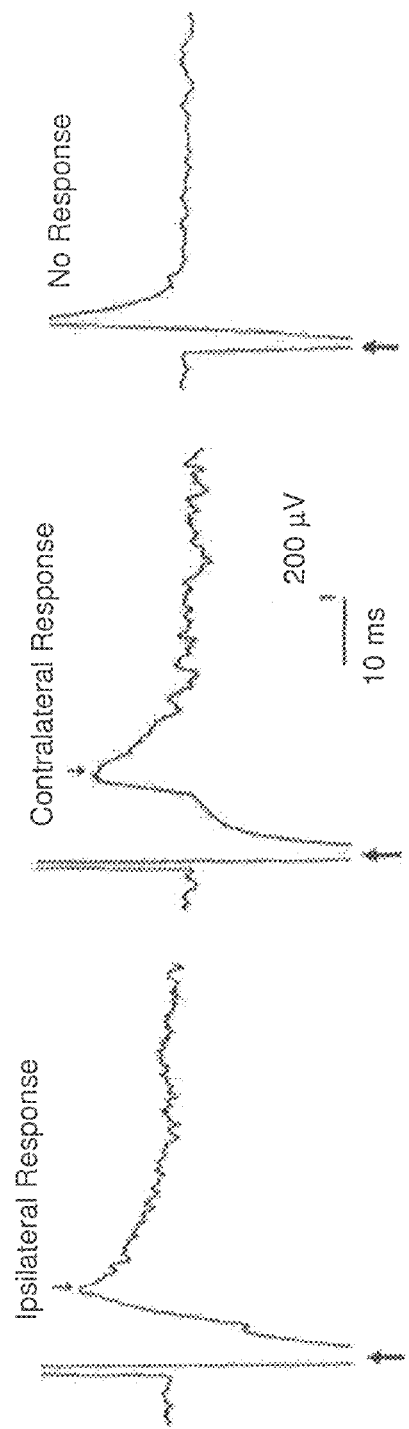

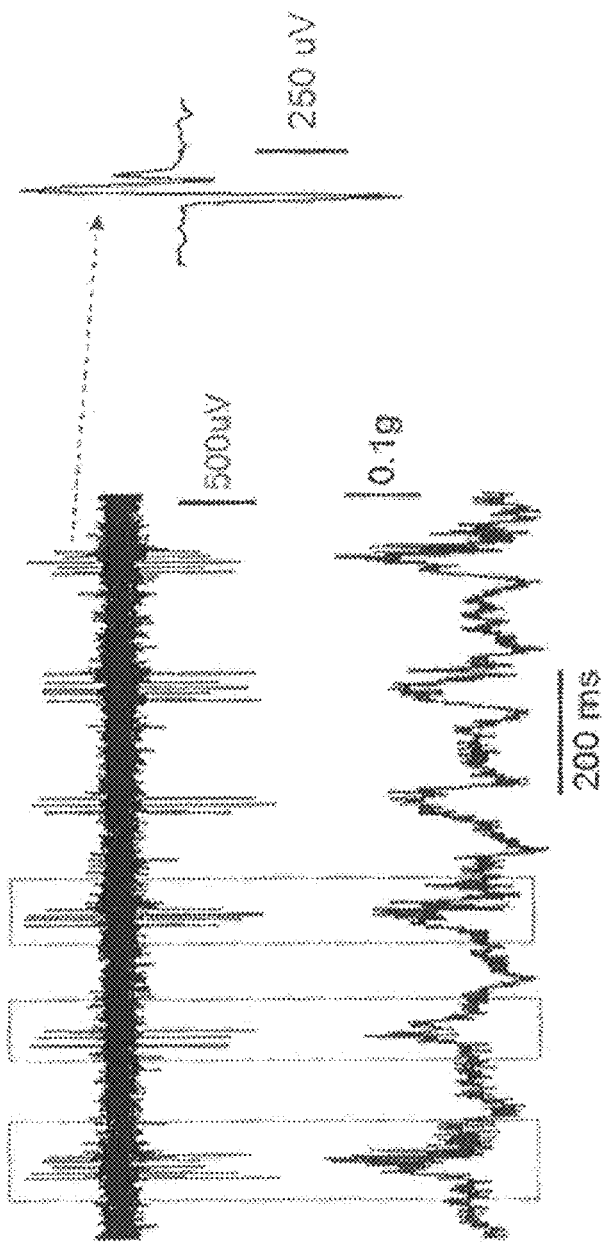

DIPOLE ELECTRICAL STIMULATION EMPLOYING DIRECT CURRENT FOR RECOVERY FROM SPINAL CORD INJURY

CROSS-REFERENCE TO RELATED APPLICATIONS

This application is a continuation of co-pending U.S. patent application Ser. No. 13/503,216, filed on Nov. 7, 2012, entitled DIPOLE ELECTRICAL STIMULATION EMPLOYING DIRECT CURRENT FOR RECOVERY FROM SPINAL CORD INJURY, which in turn is the national phase entry under 35 USC § 371 of International Patent Application No. PCT/US2010/053720 filed on Oct. 22, 2010, which in turn claims the benefit of priority from U.S. Provisional Application Ser. No. 61/253,948, filed on Oct. 22, 2009 and U.S. Provisional Application Ser. No. 61/316,319, filed on Mar. 22, 2010, the entire contents of which are incorporated herein by reference for all purposes.

STATEMENT REGARDING FEDERALLY SPONSORED RESEARCH OR DEVELOPMENT

This invention was made with support under New York State Department of Health (NYS/DOH) grant No. CO23684 and Professional Staff Congress at the City University of New York (PSCCUNY) grant No. 60027-37-39. The state of New York has certain rights in this invention.

FIELD OF THE INVENTION

The present invention generally relates to the field of providing stimulation of central nervous system tissue, muscles, nerves, or combinations thereof, and more particularly to a system and method for treating neuromuscular conditions through two-point electrical stimulation.

BACKGROUND OF THE INVENTION

The nervous system comprises the central and the peripheral nervous system. The central nervous system is composed of the brain and the spinal cord, and the peripheral nervous system consists of all of the other neural elements, namely the nerves and ganglia outside of the brain and spinal cord.

Damage to the nervous system may result from a traumatic injury, such as penetrating trauma or blunt trauma, or a disease or disorder including, but not limited to Alzheimers disease, multiple sclerosis, Huntington's disease. amyotrophic lateral sclerosis (ALS), diabetic neuropathy, senile dementia, stroke and ischemia.

After spinal cord injury (SCI), spared regions of the central nervous system are spontaneously capable of repairing the damaged pathway, although the process is very limited. Moreover, despite the many promising treatment strategies to improve connections across the damaged spinal cord, the strength of connectivity and functional recovery of the impaired spinal cord are still unsatisfactory. It is well known that spared axons sprout after SCI. See Murray M., Goldberger M. E., Restitution of function and collateral sprouting in the cat spinal cord: the partially hemisected animal, J. Comp. Neurol., 158(1):19-36 (1974); Bareyre F. M., Kerschensteiner M., Raineteau O., Mettenleiter T. C., Weinmann O., Schwab M. E., The injured spinal cord spontaneously forms a new intraspinal circuit in adult rats, Nat. Neurosci. 7:269-77 (2004); Brus-Ramer M., Carmel J. B., Chakrabarty S., Martin J. H., Electrical stimulation of spared corticospinal axons augments connections with ipsilateral spinal motor circuits after injury, J. Neurosci. 27:13793-13901 (2007). But fine-tuning of the process of sprouting of spared axons after SCI as well as synapse stabilization might be dependent on precise pathway-selective activity.

Electrical stimulation of the central and peripheral nervous systems improves neuronal connectivity, and can be employed used to improve functional recovery after neuronal injury. It is an effective method that promotes reactive sprouting through which an increase in the number of functional connections may be possible. Electrical stimulation can also improve functional connections by strengthening the weak existing synapses and/or by promoting synaptogenesis. One of the emerging concepts is that the nervous system contains latent pathways that can be awoken by electrical stimulation or pharmacological manipulation.

The majority of the methods employing electrical stimulation utilize a one-point experimental paradigm in which unipolar or bipolar stimuli are delivered at one point of the sensorimotor pathway. The effectiveness of this stimulation depends on active propagation of an action potential through spared axons. Practically, one-point stimulation would be only effective if the neuronal connections exist and can support active and successful propagation of generated potentials. Therefore, one-point stimulation would be restricted in its efficacy and inclined toward stronger connections.

The loss of neuromuscular activity after SCI leads to inevitable abnormalities that limit the effectiveness of one-point stimulation by blocking excitatory responses from traveling across the sensorimotor pathway. Some of these abnormalities are muscle atrophy and peripheral nerve inexcitability. In addition, changes of the sensorimotor pathway below and above the lesion may involve several different mechanisms; some of them may be maladaptative. This maladaptive function will bias stimuli toward connections with better integrity, further limiting the effectiveness of localized stimulation.

According to the Habbian plasticity principle, physiological processes strengthen synaptic connections when presynaptic activity correlates with postsynaptic firing. See, for example, Hebb D, Organization of Behavior, New York, Wiley (1949). This phenomenon is known as long term potentiation ("LTP"). LTP could be induced by high-frequency presynaptic stimulation or by pairing low-frequency stimulation with postsynaptic depolarization. LTP can also be induced if a pre-synaptic input is activated concurrently with post-synaptic input. In addition, direct current passed through a neuronal pathway can modulate the excitability of that pathway depending on the current polarity and neuronal geometry. In that, anodal stimulation would excite while cathodal stimulation inhibits neuronal activity.

Thus, there is a great desire to improve the effectiveness of electrical stimulation when treating neuromuscular conditions, such as SCI.

SUMMARY OF THE INVENTION

A system and method for treating neuromuscular conditions including spinal cord injury (SCI) are disclosed herein, which employ dipole (two point) cortico-muscular stimulation ("dCMS"). The system and method advantageously employ a discovery that utilizing a two point method of cortico-muscular stimulation dramatically improves the performance of the skeletal muscles after SCI. Two-point stimulation, with oppositely charged electrodes, allows pulsed, direct current to pass through the cortico-muscular pathway regardless of the extent of injury and number of spared neurons. These methods enable permanent functional recovery of the motor pathway.

The research leading to the present invention has demonstrated that dCMS substantially improved muscle twitch force and spinal cord responses in control and SCI animals, and that passage of pulsed direct current across the cortico-muscular pathway promotes stronger connections between spinal motor circuits and the motor cortex.

In one exemplary embodiment, the dCMS configuration involves an active electrode at a first point and a reference electrode at a second point, and is situated such that the current passes across the spinal cord. The first and second points may be the motor cortex, muscles, or a combination thereof. In one configuration, the active electrode can be situated at the motor cortex and the reference electrode is at a contralateral muscle (e.g., a partially isolated gastrocnemius muscle). The passage of pulsed direct current across the cortico-muscular pathway overcomes many of the excitability-confounding factors previously described. The advantage of using this method of stimulation is that the passage of such current will not be dependent on factors affected by lesion such as the degree of myelination, density of existing connections, synaptic strength and/or general excitability of the sensorimotor pathway. Instead, the current will passively flow along the core conductors of the target neuronal pathway leading to the activation of the entire pathway regardless of its morphological integrity. Dipolar cortico-muscular stimulation substantially improves muscle twitch force and spinal cord responses.

In another exemplary embodiment, electrical pulses can be applied to the spinal column employing an active electrode applied thereto. At least one reference electrode is applied to a point outside the central nervous system. The electrical pulses can be employed alone, or in combination with additional electrical pulses applied to the motor cortex and/or at least one muscle to enhance neuromuscular performance. Multiple stimulator units can be used synchronously or asynchronously to treat various traumas and/or injuries to the nervous system that are present in the brain, spinal column, or in the peripheral nerves.

The use of dCMS enhances the excitability of the cortico-muscular connections and can be used in human patients suffering from not just spinal cord injury, but also stroke, multiple sclerosis, and the like. Even humans who engage in athletic activity may use dCMS to enhance neuromuscular performance. It can practically be employed to strengthen or awaken any weak or dormant pathway in the nervous system.

According to another aspect of the present invention, a method of improving a neuromuscular condition of a vertebrate being is provided. The method includes: placing at least one active electrode at, or in proximity to, or over, a first point, and at least one reference electrode at, or in proximity to, a second point, wherein the first point is located at the central nerve system of a vertebrate being, and the second point is located outside the central nervous system of the vertebrate being, such as at the abdomen; and enhancing a neural connection between the first point and the second point by passing an electrical current between the at least one active electrode and the at least one reference electrode. In one embodiment, the reference electrode is a split electrode.

Trans-spinal direct current (tsDC) may be used to provide stimulation to the damaged or dysfunctional portions of the central nervous system and/or peripheral nerves. Transcranial DC stimulation (tcDC) may be used to modulate the excitability of the motor cortex, ameliorate the perception of pain, modulate cognitive functions, and/or treat depression. These modalities may be used alone or in conjunction with each other.

In one embodiment, the first point can be located at the spinal column of the vertebrate being. According to this embodiment, the electrical current can be provided by a stimulator including at least one stimulator unit that applies electrical pulses across the at least one active electrode and the at least one reference electrode. One or more additional reference electrodes can be placed at, or in proximity to, an additional point located outside the central nervous system of the vertebrate being. If the vertebrate being is a human, the second point and the additional point can be located at the pelvis of the human.

In another embodiment, an additional electrical stimulus can be applied to the motor cortex of the vertebrate being during passing of the electrical current between the first and second point (or "the primary electrical current") The additional electrical stimulus can be a local stimulus in the form of at least one electrical pulse. The at least one electrical pulse can be applied synchronously with, or asynchronously from, the passing of the primary electrical current.

In even another embodiment, an additional electrical stimulus can be applied to at least one muscle of the vertebrate being during passing of the primary electrical current. The additional electrical stimulus can be a stimulus in the form of at least one electrical pulse. The at least one electrical pulse can be applied synchronously with, or asynchronously from, the passing of the primary electrical current.

In yet another embodiment, a first additional electrical stimulus can be applied to the motor cortex of the vertebrate being during passing of the primary electrical current, and a second additional electrical stimulus can be applied to at least one muscle of the vertebrate being during passing of the primary electrical current. The first additional electrical stimulus can be a local stimulus in the form of at least one first electrical pulse, and the second additional electrical stimulus can be a stimulus in the form of at least one second electrical pulse. The at least one first electrical pulse and the at least one second electrical pulse can be applied synchronously with, or asynchronously from, the passing of the primary electrical current.

In still another embodiment, the primary electrical current is passed as a plurality of pulses, wherein each of the plurality of pulses has a duration from 0.5 ms to 5 ms.

In a further embodiment, the primary electrical current is passed a plurality of pulses having a frequency from 0.5 Hz to 5 Hz.

In an even further embodiment, a prompt to move a limb can be applied to the vertebrate being during, or immediately before, the passing of the primary electrical current. The prompt can be an aural prompt, a visual prompt, or a tactile prompt. The vertebrate being can be a human, and the prompt can be provided by another human to the human. Alternatively or additionally, the prompt can be provided by an automated control unit configured to generate the prompt in synchronization with the passing of the primary electrical current.

In a yet further embodiment, the vertebrate being can be a mammal, and second points can be located at a muscle in a limb of the mammal.

In a still further embodiment, the vertebrate being can be a human, and second points can be located at a muscle in a human limb.

According to another aspect of the present disclosure, another method of improving a neuromuscular condition of a vertebrate being is provided. The method includes: placing at least one active electrode at, or in proximity to, a first point located on one side of a spinal column of a vertebrate being and at least one reference electrode at, or in proximity to, a second point, wherein the first point is located on the opposite side of the spinal column, wherein locations of the first point and the second point are independently selected from the motor cortex and a muscle of the vertebrate being; and enhancing a neural connection between the first point and the second point by passing an electrical current between the at least one active electrode and the at least one reference electrode (or "the primary electrical current"). At least one path of the primary electrical current can run across the spinal column and between the first point and the second point.

In one embodiment, the at least one path of the primary electrical current includes a motor pathway between the motor cortex and a muscle. The first point can be a point at the motor cortex and the second point can be a point at a muscle. Alternatively, the second point can be a point at the motor cortex and the first point can be a point at a muscle.

In another embodiment, the first point is a point at a first muscle, and the second point is a point at a second muscle that is different from the first muscle and located on the opposite side of the spinal column from the first muscle. The at least one path of the primary electrical current includes at least one first lower motoneuron connected to the first point and at least one second lower motoneuron connected to the second point.

In even another embodiment, the at least one active electrode is a single active electrode, and the at least one reference electrode is a single reference electrode.

In yet another embodiment, the at least one active electrode is a plurality of active electrodes or the at least one reference electrode is a plurality of reference electrodes.

In still another embodiment, each of the at least one active electrode and the at least one reference electrode can be attached to the motor cortex or a muscle of the vertebrate being topically, underneath a skin, or by surgical implantation.

In still yet another embodiment, the method can further include identifying a motoneuron that affects movement of a muscle of the vertebrate being in the spinal column, wherein the muscle is subsequently attached to one of the at least one active electrode or the at least one reference electrode. The method can further include: determining a maximal stimulus strength for the motoneuron at which no further increase in muscle contraction of the muscle is observed with an increase in strength of electrical stimulation to the motoneuron; and setting a voltage differential between at least one active electrode and the at least one electrode during the passing of the current in proportion to the determined maximal stimulus strength. The voltage differential can be set at a same voltage as the maximal stimulus strength.

In a further embodiment, the primary electrical current can be passed as a plurality of pulses, wherein each of the plurality of pulses has a duration from 0.5 ms to 5 ms.

In an even further embodiment, the primary electrical current can be passed a plurality of pulses having a frequency from 0.5 Hz to 5 Hz.

In a yet further embodiment, the principle of the dipolar cortico-muscular stimulation can be achieved by applying local electrical stimulation on the target muscle at the same time of asking the individual to attempt to move the limb. As a person tries to activate the nerve muscle, a signal from the brain and through the spinal cord would be in its way to the group of muscles under activity. If the two signals—a first signal from the brain and a second signal from the nerve by electrical stimulation—meet at the level of spinal circuits, the connection specific to this group of muscles will be markedly strengthened. This principle has been applied to patients with neurologic pathology (e.g. cerebral palsy) and significant improvements have been demonstrated.

Accordingly, the method can further include providing a prompt to move a limb to the vertebrate being during, or immediately before, the passing of the primary electrical current. The prompt can be an aural prompt, a visual prompt, or a tactile prompt. The vertebrate being can be a human, and the prompt can be provided by another human to the human. The prompt can be provided by an automated control unit configured to generate the prompt in synchronization with the passing of the primary electrical current.

The vertebrate being can be a mammal, and one of the first and second points can be located at a muscle in a limb of the mammal. The vertebrate being can be a human, and one of the first and second points can be located at a muscle in a human limb.

In a still further embodiment, the primary electrical current can be provided by a stimulator that applies a first voltage to the at least one active electrode and a second voltage to the at least one reference electrode simultaneously. The primary electrical current can flow through a plurality of paths, and the plurality of paths can include a first path between the motor cortex and a muscle and a second path between two different muscles. Each of the plurality of paths can run across the spinal column, wherein at least one path of the primary electrical current runs across the spinal column.

In still yet further embodiment, one or more additional electrical stimuli can be employed synchronously or asynchronously with the flowing of the primary electrical current. The stimulator may include a plurality of stimulator units so that the additional stimulus/stimuli can be provided by a different stimulator unit than the stimulator unit(s) that provide(s) the primary electrical current between the first point and the second point. The additional stimulus/stimuli can be applied between a pair of muscles so that the additional electrical current flows through a different path that crosses the spinal column.

According to yet another aspect of the present disclosure, a system for improving a neuromuscular condition of a vertebrate being is provided. The system includes: at least one active electrode, each sized and configured to be placed at, or in proximity to, a first point located at the central nerve system of a vertebrate being; at least one reference electrode, each sized and configured to be placed at, or in proximity to, a second point that is located outside the central nervous system of the vertebrate being; a stimulator unit configured to generate electrical stimulation waveforms; and at least one first lead wire that couples the stimulator unit to the at least one active electrode and at least one second lead wire that couples the stimulator unit to the at least one reference electrode, wherein the system is configured to form a current path through a motor pathway across the spinal column between the first point and the second point.

In one embodiment, each of the at least one active electrode can be sized and configured to be placed at, or in proximity to, a spinal column of the vertebrate being. The at least one active electrode and the at least one reference electrode can be sized and configured to be placed at, or in proximity to, the spinal column of a human.

In another embodiment, the system can further include at least another active electrode and at least another reference electrode, each sized and configured to be placed at, or in proximity to, the motor cortex of the vertebrate being. The at least another active electrode and the at least another reference electrode can be sized and configured to be placed at, or in proximity to, the motor cortex of a human. The system can further include another stimulator unit configured to generate additional electrical stimulation waveforms that are applied across the at least another active electrode and the at least another reference electrode. The stimulator unit and the other stimulator unit can be synchronized to provide the electrical stimulation and the additional electrical stimulation simultaneously.

In yet another embodiment, the system can further include at least another active electrode and at least another reference electrode, each sized and configured to be placed at, or in proximity to, a muscle of the vertebrate being. The at least another active electrode and the at least another reference electrode can be sized and configured to be placed at, or in proximity to, a muscle of a human. The stimulator unit and the other stimulator unit can be synchronized to provide the electrical stimulation and the additional electrical stimulation simultaneously.

In still another embodiment, the system can further include prompt means for providing a prompt to move a limb to the vertebrate being during, or immediately before, the passing of the electrical current.

According to still another aspect of the present disclosure, another system for improving a neuromuscular condition of a vertebrate being is provided. This system includes: at least one active electrode, each sized and configured to be placed on, or in proximity to, a first point that is selected from the motor cortex and a muscle and is located on one side of a spinal column of a vertebrate being; at least one reference electrode, each sized and configured to be placed on, or in proximity to, a second point that is selected from the motor cortex and a muscle and is located on the opposite side of the spinal column; a stimulator unit configured to generate electrical stimulation waveforms; and at least one first lead wire that couples the stimulator unit to the at least one active electrode and at least one second lead wire that couples the stimulator unit to the at least one reference electrode, wherein the system is configured to form a current path through a motor pathway across the spinal column between the first point and the second point.

In one embodiment, one of the at least one active electrode and the at least one reference electrode is sized and configured to be placed on, or in proximity to, the motor cortex. This electrode can be sized and configured to be placed on, or in proximity to, the motor cortex of a mammal having limbs. Alternatively or additionally, this electrode or another electrode can be sized and configured to be placed on, or in proximity to, the motor cortex of a human.

In another embodiment, all of the at least one active electrode and the at least one reference electrode are sized and configured to be placed on, or in proximity to, a muscle of the vertebrate being. All of the at least one active electrode and the at least one reference electrode can be sized and configured to be placed on, or in proximity to, a muscle in a limb of a mammal having limbs. Further, all of the at least one active electrode and the at least one reference electrode can be sized and configured to be placed on, or in proximity to, a human limb.

In even another embodiment, the at least one active electrode is a single active electrode, and the at least one reference electrode is a single reference electrode.

In yet another embodiment, the at least one active electrode is a plurality of active electrodes or the at least one reference electrode is a plurality of reference electrodes.

In still another embodiment, each of the at least one active electrode and the at least one reference electrode is configured to be attached to the motor cortex or a muscle of the vertebrate being topically, underneath a skin, or by surgical implantation.

In still yet another embodiment, the system further includes at least one probe for identifying a motoneuron that affects movement of a muscle of the vertebrate being and located in the spinal column by applying electrical voltage thereto.

In a further embodiment, the stimulator is configured to pass the electrical current as a plurality of pulses having a duration from 0.5 ms to 5 ms.

In an even further embodiment, the stimulator is configured to pass the electrical current as a plurality of pulses having a frequency from 0.5 Hz to 5 Hz.

In a yet further embodiment, the system further includes prompt means for providing a prompt to move a limb to the vertebrate being during, or immediately before, the passing of the electrical current. The prompt can be an aural prompt, a visual prompt, or a tactile prompt. The prompt means can be an automated control unit configured to generate the prompt in synchronization with the passing of the electrical current.

In a still further embodiment, the stimulator is configured to apply a first voltage to the at least one active electrode and a second voltage to the at least one reference electrode simultaneously.

In further another embodiment, the stimulator is configured to pass the electrical current flows through a plurality of paths. The plurality of paths can include a first path between the motor cortex and one of the plurality of muscles and a second path between two of the plurality of muscles.

In even further another embodiment, the stimulator can be configured to apply a first voltage to the at least one active electrode and a second voltage to the at least one reference electrode simultaneously. The electrical current can be provided by the stimulator including at least one stimulator unit that applies the first voltage to the at least one active electrode and the second voltage to the at least one reference electrode to improve the neuromuscular condition of the vertebrate being. The at least one stimulator unit can apply the first voltage and the second voltage simultaneously to improve the neuromuscular condition of the vertebrate being.

In yet further another embodiment, the at least one stimulator unit can include a plurality of stimulator units. The first voltage can be applied by a first stimulator unit and the second voltage can be applied by a second stimulator unit simultaneously. Further, polarizing current can be delivered between the brain of the vertebrate being and a muscle of the vertebrate being by employing a third stimulator unit to improve the neuromuscular condition of the vertebrate being. The third stimulator unit can be synchronized with the first and second stimulator units so that the polarizing current is delivered simultaneously with the first voltage and the second voltages. Alternatively, the third stimulator unit can be operated independently from the first and/or second stimulator unit(s) so that the polarizing current is delivered asynchronously from the first voltage and/or the second voltage.

In still further another embodiment, the at least one stimulator unit can be a plurality of stimulator units including a stimulator unit configured to apply the first voltage and the second voltage simultaneously. Polarizing current can be delivered between the brain of the vertebrate being and a muscle of the vertebrate being employing another stimulator unit such as the third stimulator unit. The other stimulator unit, e.g., the third stimulator unit, can be synchronized with the stimulator unit that delivers the first voltage and/or the second voltage so that the polarizing current is delivered simultaneously with the first voltage and the second voltages. Alternatively, the other stimulator unit can be operated independently from the stimulator unit so that the polarizing current is delivered asynchronously from the first voltage and the second voltages to improve the neuromuscular condition of the vertebrate being.

The present disclosure provides new motor pathway therapies, which provide permanent restoration of neural communications after a series of therapy sessions. The absence of the need for re-treatment is a distinguishing feature of the present disclosure over prior art methods such as functional electric stimulation (FES) that require periodic re-treatment of muscles. The motor pathway therapies of the present disclosure can repair neural connection to improve the function of an existing communication pathway and/or can create/facilitate new neuronal growth for additional neural communication in such pathway. The motor pathway therapies of the present disclosure can permanently restore healthy neural communications without the need for re-treatment in order to continue to enjoy such improvement.

As an illustration of treatment of a partially or wholly immobilized patient, treatment of the inured neuronal motor pathway for several short stimulation sessions repeated over several weeks can result in permanent neuronal pathway communication improvement: now the patient can grasp an object. However, follow-on treatment to induce still further restoration of neural health in such treated pathway would be a next step: now the treated patient can lift the grasped object.

BRIEF DESCRIPTION OF THE DRAWINGS

FIG. 1B is an illustration of three phases of pulses designed to evaluate dCMS.

FIG. 3A illustrates the responses to the gastrocnemius muscle after stimulation.

FIG. 3B is an illustration showing the identification of motoneurons when their spontaneous activity (upper panel) is time locked and spontaneous contractions at the ipsilateral muscle (lower panel).

FIGS. 14 A and 14B are examples of spontaneous activity recorded before (baseline), during, and after a-tsDC (A) or c-tsDC (B) are shown.

In FIG. 14C, the firing frequency during a-tsDC showed a significant effect of condition (F=135.40, p<0.001, repeated measures ANOVA). Post hoc tests revealed a higher firing frequency during a-tsDC steps +1, +2, and +3 mA.

In FIG. 14D, firing frequency during c-tsDC also showed a significant effect of condition (F=338.00, p<0.001, repeated measures ANOVA). Post hoc testing revealed a significant difference during c-tsDC steps −2, and −3 mA.

In FIG. 14E, spike amplitude during a-tsDC showed a significant effect of condition (H=738.14 p=0.001, Kruskal-Wallis ANOVA). Post hoc tests revealed a higher spike amplitude during a-tsDC +2 and +3 mA.

In FIG. 14F, spike amplitude during c-tsDC also showed an effect of condition (H=262.40, p≤0.001, Kruskal-Wallis ANOVA). Post hoc tests revealed a higher spike amplitude during c-tsDC. Error bars represent S.E.M. *p<0.05 relative to baseline.

In FIG. 5A, autocorrelogram of a-tsDC-induced activity shows no oscillation or bursting. In FIG. 5B, autocorrelogram of c-tsDC-induced activity shows strong bursts by 10 ms and oscillations. In FIG. 5C, oscillatory activity was also induced by injecting the glycine and GABA receptor blockers picrotoxin and strychnine into the spinal cord at L3-L4.

In FIG. 16A, examples of TS twitches evoked before (baseline), during, and immediately after a-tsDC are shown. Note that a-tsDC depressed the ability of the motor cortex to elicit TS twitches during stimulation, but facilitated twitches after stimulation. In FIG. 16B, however, c-tsDC improved the ability of the motor cortex to elicit TS twitches during stimulation, but not afterwards. For each animal (n=5/group), the average of ten TS twitches was analyzed before stimulation (baseline), during the five intensity steps, and after stimulation (0, 5, and 20 min) with a-tsDC as illustrated in FIG. 16C or c-tsDC as illustrated in FIG. 16D.

In FIG. 17A, latencies of tibial nerve potentials, measured from the stimulus artifact (SA) to the first deflection of the potential, were prolonged during a-tsDC and shortened after a-tsDC. Dashed vertical lines mark the points of measurement. Note the difference in the scale bars. In FIG. 17B, latencies of cortically-elicited tibial nerve potentials were shortened during c-tsDC and prolonged afterwards. FIG. 17C illustrate that, for a-tsDC, there was a significant effect of condition (H=30.10, p<0.001, Kruskal-Wallis ANOVA). Post hocs revealed a significantly longer latency during +2 mA and a shorter latency afterwards. FIG. 17D illustrate that, for c-tsDC, there was also a significant effect of condition (H=29.84, p<0.001, Kruskal-Wallis ANOVA). Post hocs revealed a significantly shorter latency during −2 mA and a longer latency afterwards. Error bars represent S.E.M. *p<0.05 relative to baseline.

DETAILED DESCRIPTION OF THE INVENTION

Figure 1A:
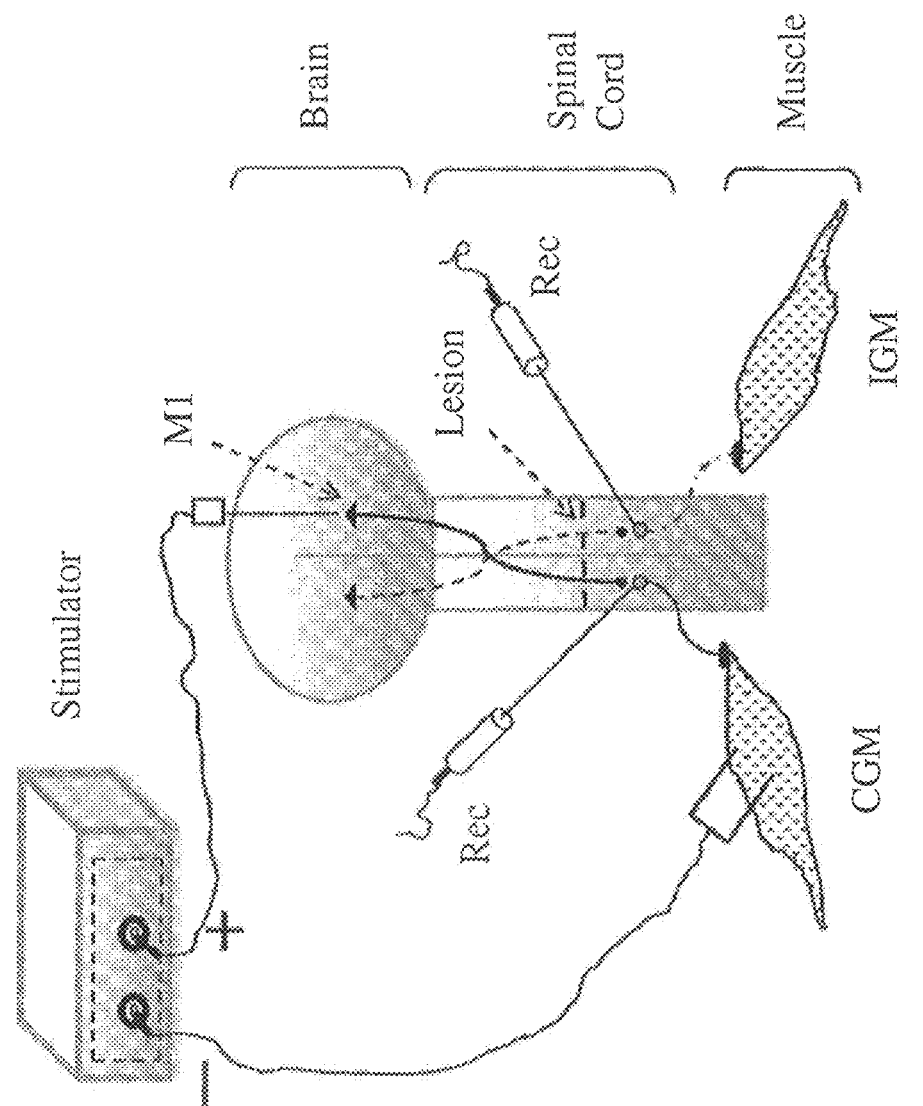
FIG. 1A is an illustration of the basic configuration and setup for utilizing dipole cortico-muscular stimulation (dCMS).

As stated above, the present invention relates to a system and method for treating neuromuscular conditions through two-point electrical stimulation, which are now described in detail with accompanying figures. It is also noted that drawings are not necessarily drawn to scale.

As used herein, a "vertebrate being" refers to any biological animal that has a spinal column, and includes humans and all animals classified under subphyla Vertebrata.

As used herein, a "limb" is a leg, an arm, a wing, a flipper, a side of a fin, or any anatomical equivalent thereof of a vertebrate being.

As used herein, a first element is placed "in proximity to" a second element if a predominant portion (greater than 50%) of electrical current applied to the first element flows to the first element or vice versa. When multiple electrodes are said to be placed in proximity to a point, a predominant portion of electrical current applied to the multiple electrodes flow through the point, and consequently through an element including that point.

As used herein, a "point" refers to a tissue site of an animal or a human.

As used herein, an element is "configured to" perform an act if the element is shaped, and includes all necessarily intrinsic features, to enable performance of the act as a natural consequence of having the shape and the necessary feature.

As used herein, an "active electrode" is an electrode to which an electrical pulse is applied either as at least one positive voltage pulse or at least one negative voltage pulse. Therefore, an active electrode can be a positive electrode or a negative electrode depending on the polarity of the applied electrical pulse.

As used herein, a "reference electrode" is an electrode that provides a reference voltage to a vertebrate being while an active electrode applies an electrical pulse. A reference electrode may be held at a constant electrostatic potential, or an electrical pulse may be applied to the reference electrode such that the electrical pulse applied to the reference electrode has a polarity that is the opposite of the polarity of the electrical pulse applied to at least one active electrode. If at least one active electrode is at least one positive electrode, a reference electrode is a negative electrode, and vice versa.

As used herein, a "polarizing current" refers to a direct current electrical current that flows and through a neuron between a first electrode and a second electrode and causes polarization of electrical charges in the neuron.

As used herein, a "central nervous system" is the set of a brain and a spinal column of a vertebrate being.

As used herein, a "lower motoneuron" or a "lower motor neuron" is a motor neuron connecting the spinal column to a muscle fiber(s) and including an axon that terminates at the muscle fiber(s).

The application of dipole cortico-muscular stimulation (dCMS) results in a remarkable enhancement of the excitability of the motor pathway. This enhancement was observed in both animals and humans. In control animals and in SCI animals, which had severe locomotor impairment associated with signs of spastic syndrome, the effect was observed both in the ipsilateral and contralateral pathways. Maximal threshold of the ipsilateral cortex was reduced. Improvement in muscle strength was accompanied by an increase in spontaneous activity and potentiation of evoked responses of the spinal motoneurons. Spinal motoneuronal responses and muscle twitches evoked by stimulation of the contralateral, non-treated M1 (motor cortex) were significantly enhanced as well. The dCMS-induced effect persisted beyond the phase of stimulation and extended through the entire period of the experiment as explained in detail further below.

The electrodes may be attached topically on the surface, or underneath the skin, or surgically implanted. In one embodiment, an active electrode is situated on the motor cortex (first point) and a reference electrode is situated on the desired muscle (second point), allowing the current to travel across the spinal cord. In another embodiment, an active electrode is situated on the desired muscle (first point) and a reference electrode is situated on the motor cortex (second point), again allowing the current to travel across the spinal cord. In yet another embodiment, neither the active electrode nor the reference electrode is placed on the motor cortex. Instead, both the active electrode and reference electrode are placed on desired first and second point muscles, which are on opposite sides of the body, allowing the current to travel across the spinal cord.

Figure 10:
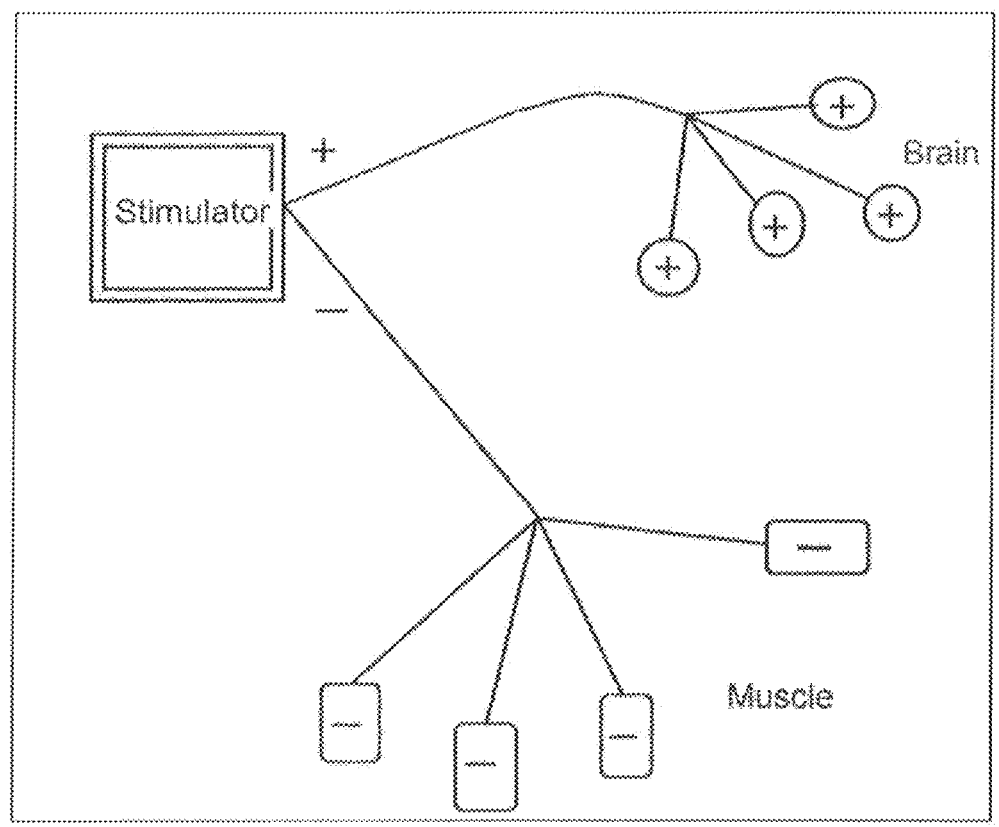
FIG. 10 is a first configuration of a simulator and a plurality of active electrodes (labeled "+") and a plurality of reference electrodes (labeled "−").

In one embodiment of the present disclosure, a dipolar cortico-muscular stimulator can be employed to provide electrical pulses for the purposes of the present disclosure. FIG. 10 illustrates an exemplary connection scheme employing a dipolar cortico-muscular stimulator. A dipolar cortico-muscular stimulator can include a stimulator box with a LCD Display or computer connections to a software control system. In a non-limiting illustrative example, a dipolar cortico-muscular stimulator having the following configuration can be employed:

Pulse Type: Constant current
Wave form: Rectangular
Pulse duration 0.5 to 5 ms
Pulse amplitude 1 to 15 mA (Voltages at 1 to 35V)
Frequency range 0.5 to 5 Hz
Inherent Safety/shutdown features to prevent over stimulation The outputs are connected in a way that makes the stimulus intensity to be the difference between the voltages at the positive and negative outputs. The regulations of both outputs are synchronized to make the absolute value of the difference between these two outputs always the same. Thus, when the positive output increases the negative output should decrease the same amount. For example, when the positive output is increased from +4 V to +5 V, the negative output decreases from −1 V to 0 V.

Digital-to-analog converter (DAC) can be used to provide analog output, i.e., stimulation, through analog outputs of the stimulator box. The DACs can produce constant DC voltage levels or waveforms under software control. The output of the DACs may be fed through a programmable attenuation network to produce different output ranges. The signal may be then split into a positive and negative output through buffer amplifiers.

Optionally, each of the electrode wires can be split and connected to multiple locations. For example, active electrode can be split into multiple wires each with its own electrode. This is important in human application in case more areas needed to be stimulated. For example, at the cortex, an operator can use only one active electrode for focal stimulation or two active electrodes for more broad but less painful stimulation. Also, at the muscle, the operator can include more parts of the limb in the same session. Individual electrode size should be about 5 cm$^2$.

This system can be employed to improve a neuromuscular condition of the vertebrate being. The at least one active electrode is placed at, or in proximity to, a first point. The at least one reference electrode is placed at, or in proximity to, a second point. As discussed above, each of the first point is located on one side of a spinal column of a vertebrate being, and each of the second point is located on the opposite side of the spinal column. Each location of the first point and the second point can be independently selected from the motor cortex and a muscle of the vertebrate being. Each muscle includes at least one nerve. Electrical current is passed between the at least one active electrode and the second electrode. At least one path of the electrical current runs across the spinal column and between the first point and the second point.

In one embodiment, one of the at least one active electrode and the at least one reference electrode can be sized and configured to be placed at, or in proximity to, the motor cortex. Such an electrode can be sized and configured to be placed at, or in proximity to, the motor cortex of a mammal having limbs or the motor cortex of a human. The at least one active electrode and the at least one reference electrode can be placed on the vertebrate being such that the at least one path of the electrical current includes a motor pathway between the motor cortex and a muscle. The first point can be a point at the motor cortex and one of the second point can be a point at a muscle. Alternatively, the second point can be a point at the motor cortex and the first point can be a point at a muscle.

In another embodiment, all of the at least one active electrode and the at least one reference electrode can be sized and configured to be placed at, or in proximity to, a muscle of the vertebrate being. Thus, all of the at least one active electrode and the at least one reference electrode can be sized and configured to be placed at, or in proximity to, a muscle in a limb of a mammal having limbs or a human limb. The at least one active electrode and the at least one reference electrode can be placed on the vertebrate being such that the first point is a point at a first muscle, and the second point is a point at a second muscle. The at least one path of the electrical current can include at least one first lower motoneuron connected to the first point and at least one second lower motoneuron connected to the second point.

Figure 11:
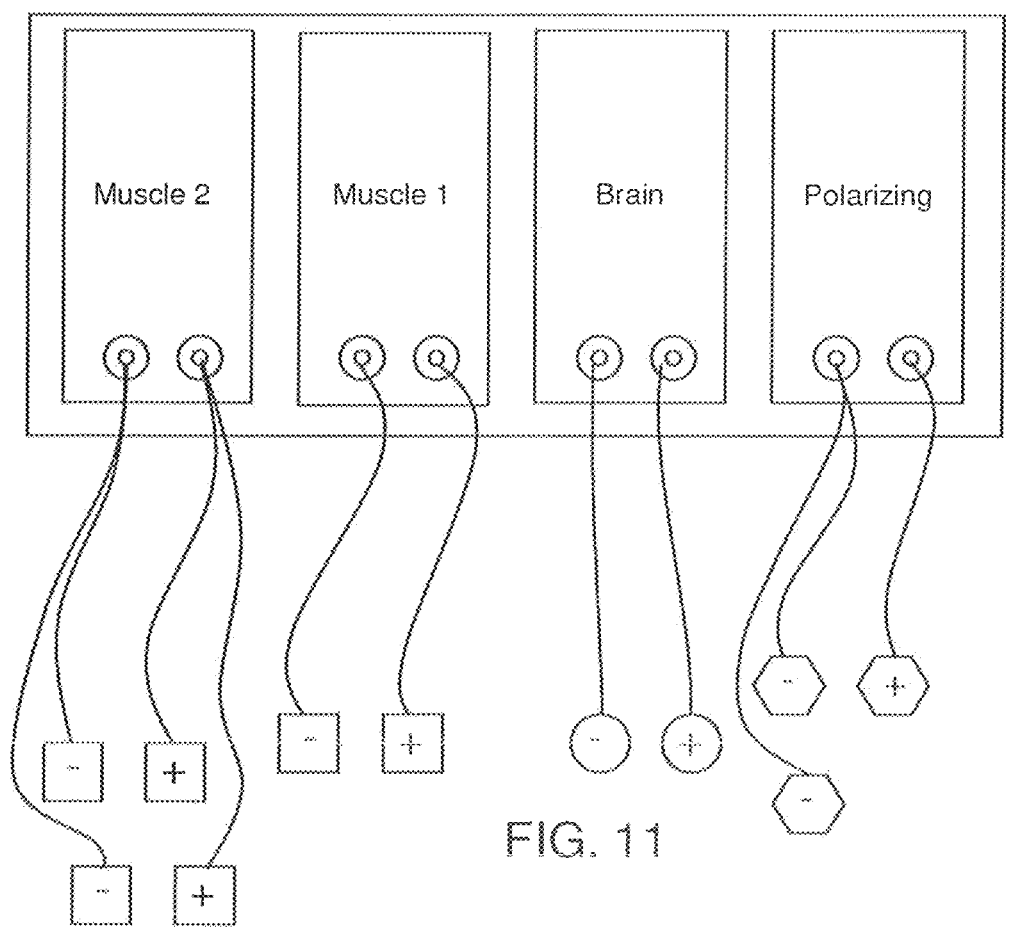
FIG. 11 is a second configuration of a simulator including multiple simulator units and electrodes attached thereto.

The at least one active electrode can be a single active electrode, and the at least one reference electrode can be a single reference electrode as illustrated in FIG. 1A. Alternatively, the at least one active electrode can be a plurality of active electrodes and/or the at least one reference electrode can be a plurality of reference electrodes as illustrated in FIGS. 10 and 11.

If multiple electrodes are employed for either the at least one active electrode or the at least one reference electrode, the multiple electrodes can be placed at, or in proximity with, the same muscle. For example, a plurality of first electrodes can be placed at, or in proximity with, the motor cortex, and a plurality of second electrodes can be placed at, or in proximity with, a muscle. Further, a plurality of first electrodes can be placed at, or in proximity with, a first muscle, and a plurality of second electrodes can be placed at, or in proximity with, a second muscle that is different from the first muscle. In each of the examples above, the at least one active electrode can be the plurality of first electrodes and the at least one reference electrode can be the plurality of second electrodes, or vice versa.

Each of the at least one active electrode and the at least one reference electrode can be configured for attachment to the motor cortex or a muscle of the vertebrate being by any method, and particularly, topically, underneath a skin, and/or by surgical implantation. In this case, the method of the present disclosure can include attaching each of the at least one active electrode and the at least one reference electrode to the motor cortex or a muscle of the vertebrate being topically, underneath a skin, and/or by surgical implantation.

In still yet another embodiment, the system can include at least one probe for identifying a motoneuron that affects movement of a muscle of the vertebrate being and located in the spinal column by applying electrical voltage thereto. An example of such at least one probe is the pair of pure iridium microelectrodes illustrated in FIG. 1A and labeled as "Rec." If provided, the at least one probe can be employed to identifying a motoneuron that affects movement of a muscle of the vertebrate being in the spinal column. The muscle is subsequently attached to an active electrode or a reference electrode. The at least one probe can be employed to determine a maximal stimulus strength for the motoneuron at which no further increase in muscle contraction of the muscle is observed with an increase in strength of electrical stimulation to the motoneuron. Then, a voltage differential between at least one active electrode and the at least one electrode during the passing of the current can be set in proportion to the determined maximal stimulus strength. For example, the voltage differential can be set at a same voltage as the maximal stimulus strength, or can be a predefined percentage of the maximal stimulus strength (e.g., 25% to 200%).

In one embodiment, the stimulator can be linked to EMG (electro-myograph, muscle activity monitor) monitor to adjust the level (e.g. 50%) of muscle contraction at which the treatment session will be delivered. Similar monitor for vital signs (heart rate; blood pressure, breathing rate) can be added. Electrode gel can be used to prevent burns due to electrolysis.

Another method of employing a dipolar cortico-muscular stimulator is illustrated in FIG. 11. The stimulation system includes multiple independent stimulator units that are integrated in a single system, either in one box or in a plurality of boxes with electrical connections therebetween. A first stimulator unit, labeled "polarizing," delivers a polarizing current between a point on a spinal column and a point located outside of the central nervous system. Optionally, a second stimulator unit, labeled "brain," can deliver current to the motor cortex either synchronously with the polarization current or asynchronously with the polarization current to reinforce the stimulation provided by the first stimulator. Optionally, a third stimulator unit, labeled "muscle 1," can deliver current to a muscle area either synchronously with the polarization current or asynchronously with the polarization current to reinforce the stimulation provided by the first stimulator. The third stimulator unit can be used with the second stimulator unit, or without the second stimulator unit. Additional stimulator units, represented by a fourth stimulator unit labeled "muscle 2," can be used with the third stimulator unit to deliver monopolar negative current to another muscle area.

Figure 12:
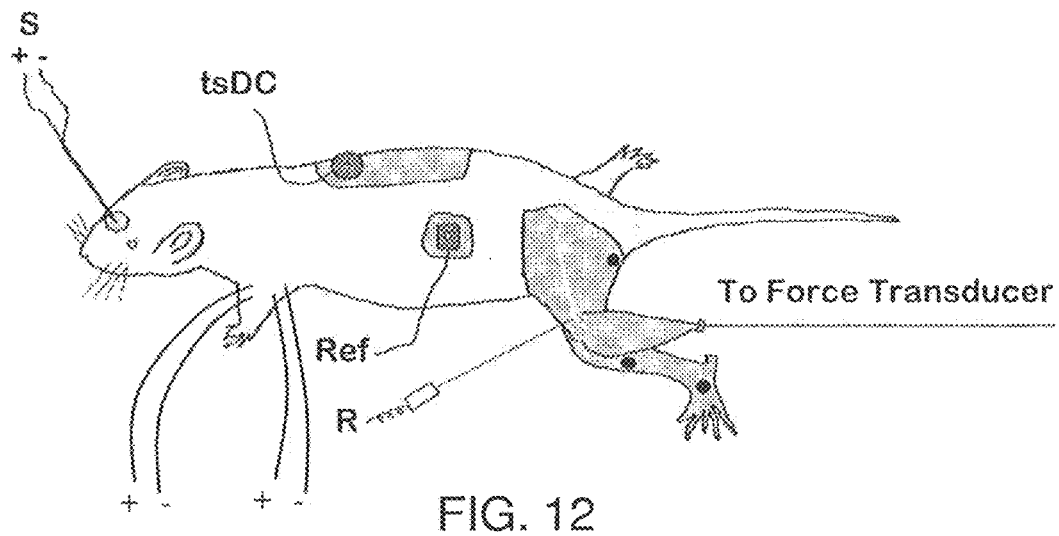
FIG. 12 is an exemplary setup employing the second configuration. This setup was also employed for an experimental setup for the study described below.

The points at which the polarizing current is applied to a vertebrate being are schematically illustrated in FIG. 12. While a mouse is schematically shown in FIG. 2, this configuration can be employed for any vertebrate being including a human. Specifically, an active electrode, labeled "tsDC," is placed on a first point located at the spinal column, which can be at any level within the spinal column between, and including, the first spinal cord level and the last spinal cord level. A reference electrode, labeled "Ref," can be placed on a second point located at any area other than the area of the central nervous system, i.e., outside of the brain and the spinal column. Because simulation of an area of the spinal column contacted by the active electrode is preferred than stimulation of the area contacted by the reference electrode, the reference electrode is preferably placed at some distance away from the spinal column. While the reference electrode is shown as a single electrode in FIG. 12, the reference electrode can be replaced with a plurality of reference electrodes as illustrated in FIG. 11. Using a plurality of reference electrodes instead of a single reference electrode enhances the effect of the electrical stimulation provided by the active stimulus because the current density at the plurality of reference electrodes can be maintained low, while the current density at the active electrode can be maintained high.

Typically, the voltage at the reference electrode(s) is held constant, and the voltage at the active electrode has the form of electrical pulses with a pulse duration 0.5 to 5 ms and a frequency from 0.5 Hz to 5 Hz, although lesser and greater pulse durations and lesser and greater frequencies can also be employed. The polarity of the electrical pulse applied to the active electrode can be either positive or negative depending on applications.

In case the vertebrate being is a human, a pair of reference electrodes placed on an anterior pelvis can provide effective stimulation to an area of the spinal column. One of the most effective configurations for placement of a pair of reference electrodes employs a point at the anterior superior iliac spine on the right side and a point at the anterior superior iliac spine on the left side. In this case, a second point for placing a reference electrode in an embodiment employing a single reference electrode is replaced by a second point and an additional point on which two reference electrodes are placed. In other words, a reference electrode for spinal polarizing current can be implemented as a pair of reference electrodes that are split and placed over the right and left anterior superior iliac spines. The pair of reference electrodes is held at the same electrostatic potential.

The location of the first point, i.e., the point at which the active electrode is placed, depends on the nature of the neuromuscular condition for which the treatment is performed. The location of the first point can be selected to maximize the effect of the treatment. For example, if the treatment is intended to improve the neuromuscular condition of a vertebrate being for injuries suffered at a location in the spinal column, the first point can be located in a spinal cord level immediately above, i.e., immediately more proximal to the brain than, the site of the spinal injury. In other words, for treatment of a spinal cord injury, the active electrode of polarizing current can be placed so that the primary current passes through the injury site. An active electrode is placed at the spinal cord level immediately above the injury site, and reference electrodes can be placed as described above. In one embodiment, repetitive stimulations at the brain (pulsed DC current that are applied synchronously with, or asynchronously from, the primary electrical current through the active electrode and the reference electrode(s)) can be paired with the polarizing spinal current.

If the treatment is intended to improve the neuromuscular condition of a vertebrate being for conditions caused by a trauma or a dysfunction in the brain, the first point can be located at the spinal cord level one, i.e., the part of the spinal column closest to the brain. Conditions caused by a trauma or a dysfunction in the brain include such disabilities as cerebral palsy, amyotrophic lateral sclerosis (ALS, otherwise known as Lou Gehrig's disease), traumatic brain injury, stroke, etc. In other words, for treatment of conditions where the injury is located in the brain, the polarizing electrode can be located on the spinal area innervating the target limb. For treatment of conditions affecting lower extremities, the active polarizing electrode should be situated at vertebral level T10 to L1 above the lumbar enlargement. For treatment of conditions affecting upper extremities, the active polarizing electrode can be placed at the level of T2 and below.

In one embodiment, repetitive stimulations at the brain (pulsed DC current that are applied synchronously with, or asynchronously from, the primary electrical current through the active electrode and the reference electrode(s)) can be paired with the polarizing spinal current.

For treating a condition such as ALS, stimulation intervention can also be applied to target muscles (in the form of localized pulsed DC current) affected by the condition, simultaneously with application of the polarizing current to a spinal cord region innervating the target muscles and application of local stimulation to the motor cortex (in the form of localized pulsed DC current). These treatments should be repeated at different areas according to the condition.

If the treatment is intended to improve the neuromuscular condition of a vertebrate being for injuries to, or disabilities caused by a malfunction at, a peripheral nerve, the first point can be located in a spinal cold level at which a corresponding lower extremity circuit is located, and preferably at a spinal cord level that is most proximal to the location of the injury or the disability. Conditions caused by an injury or a disability located at a nerve include, for example, peripheral palsy, Erb's palsy, and/or other peripheral nerve injuries due to nerve compression, tension, or torsion (e.g., sciatica). For treating a condition such as Erb's palsy, stimulation intervention can also be applied to target muscles (in the form of localized pulsed DC current) affected by the condition, simultaneously with application of the polarizing current to a spinal cord region innervating the target muscles and application of local stimulation to the motor cortex (in the form of localized pulsed DC current). These treatments should be repeated at different areas according to the condition.

The electrical simulation to the spinal column can be provided alone or in combination with additional electrical stimulations to the brain and/or to at least one muscle. The effectiveness of synchronous or asynchronous application of additional electrical simulation to the brain and/or the at least one muscle depends on the nature of the injury or disability.

An electrical stimulation to the brain is schematically illustrated in FIG. 12 by two electrodes placed at the motor cortex of a vertebrate being. The electrical stimulation provided to the brain is a local stimulation in which an area of the motor cortex of the electrical being is stimulated synchronously with, or asynchronously from, the electrical stimulation of the spinal column by the first stimulator unit. The local electrical stimulation to the motor cortex can be applied employing a concentric electrode pair as illustrated in FIG. 12, or can be employed by a set of electrodes, e.g., a third electrode and a fourth electrode that are placed at two different points at the motor cortex. The third electrode and the fourth electrode are schematically shown in FIG. 11 as two electrodes connected to the second stimulator unit labeled "Brain."

Additional electrical stimulation can be provided to at least one muscle, i.e., a single muscle or a plurality of muscles, synchronously with, or asynchronously from, the electrical stimulation of the spinal column by the first stimulator unit. If a local electrical stimulation to the brain is employed, the additional electrical stimulation the at least one muscle can be applied synchronously with, or asynchronously from, the local electrical stimulation to the brain by the second stimulator unit. The additional electrical stimulation can be provided by a third stimulator unit and/or additional stimulator unit(s), such as the stimulator units labeled "Muscle 1" and "Muscle 2" in FIG. 11. A single pair of electrodes or multiple pairs of electrodes can be connected to a stimulator unit that stimulates a muscle. FIG. 12 schematically illustrates an exemplary placement scheme for the additional electrodes in which the additional electrodes are placed on a forelimb of a mouse. In general, at least one pair of additional electrodes can be placed at one or multiple pairs of points on any part of the body excluding the central nervous system, and particularly at any limb.

Electrodes connected to each of the stimulator units in FIG. 11 can be a single pair of electrodes or multiple pairs of electrodes. Each pair of electrodes includes an active electrode and a reference electrode. Further, each reference electrode can be replaced with a plurality of reference electrodes to prevent concentration of current to a single reference electrode and to enable increase in the current density at the point at which the corresponding active electrode is present.

The second stimulator unit can deliver monopolar positive current to the motor cortex either synchronously with the polarization current or asynchronously with the polarization current to reinforce the stimulation provided by the first stimulator. Further, the third stimulator unit, labeled "muscle 1," can deliver monopolar negative current to a muscle area either synchronously with the polarization current or asynchronously with the polarization current to reinforce the stimulation provided by the first stimulator. Selecting the polarity of the electrical stimulations so that the voltages applied to the motor cortex is in general positive and the voltages applied to the at least one muscle is in general negative can enhance the effectiveness of the treatment, especially when the electrical stimulations are applied synchronously.

As discussed above, the first and second monopolar stimulator units of FIG. 11 can be synchronized to deliver pulses simultaneously. Each unit can have its independent control panel. The third, polarizing stimulator unit can have the options to be either synchronized with the first and second stimulators, or can function independently, i.e., asynchronously from the first and second stimulators. In addition, the number of electrodes per connection (splitting into more than one electrode, e.g. 4) can be as in the previous design as described above. For some applications, a dipolar cortico-muscular stimulator in this configuration is more preferable for human intervention because the stimulator gives more flexibility in designing stimulation patterns, and can be safer and less painful.

In general terms, the invention described herein can be practiced employing a system for improving a neuromuscular condition of a vertebrate being. The system includes at least one active electrode, at least one reference electrode, a stimulator, and at least one first lead wire and at least one second lead wire, which are employed to form an electrical circuit that includes a vertebrate being.

Each of the at least one active electrode can be sized and configured to be placed at, or in proximity to, a first point. The first point is selected from the motor cortex and a muscle, and is located on one side of a spinal column of the vertebrate being. The at least one active electrode can be a single active electrode as illustrated in FIG. 1A (See the section on experimental data for description of components in FIG. 1A), or can be a plurality of active electrodes as illustrated in FIG. 10, or include a active electrode attached to a stimulator unit (labeled "brain") and at least another active electrode attached to another stimulator unit (labeled "polarizing") as illustrated in FIG. 11.

Each of the at least one reference electrode can be sized and configured to be placed at, or in proximity to, a second point. The second point is selected from the motor cortex and a muscle, and is located on the opposite side of the spinal column. The at least one reference electrode can be a single reference electrode as illustrated in FIG. 1A, or can be a plurality of reference electrodes as illustrated in FIG. 10, or include a reference electrode attached to a stimulator unit (labeled "muscle") and at least another reference electrode attached to another stimulator unit (labeled "polarizing") as illustrated in FIG. 11.

The stimulator can be configured to generate electrical stimulation waveforms. Each of the at least one first lead wire couples the stimulator to an active electrode among the at least one active electrode. Each of the at least one second lead wire couples the stimulator to one of the at least one reference electrode. In one embodiment, the system can be configured to form a current path through a motor pathway across the spinal column between the first point and the second point. In another embodiment, the system can be configured to form a current path between a first point in the spinal column and a second point outside the central nervous system.

The stimulator can configured to pass the electrical current as a plurality of pulses having a duration from 0.5 ms to 5 ms, although lesser and greater durations can also be employed. Further, the stimulator can configured to pass the electrical current as a plurality of pulses having a frequency from 0.5 Hz to 5 Hz.

The system can further include prompt means for providing a prompt to move a limb to the vertebrate being during, or immediately before, the passing of the electrical current. The prompt can be provided in any of the embodiments described above. The prompt can be an aural prompt, a visual prompt, or a tactile prompt. The prompt means can be an automated control unit configured to generate the prompt in synchronization with the passing of the electrical current. The prompt means can be used for any vertebrate being capable of understanding the prompt, or trained to recognize the prompt (for example, by conditional reflexes). In this case, a prompt to move a limb can be provided to the vertebrate being during, or immediately before, the passing of the electrical current. The prompt can be provided by an automated control unit configured to generate the prompt in synchronization with the passing of the electrical current.

Alternatively or in addition, the vertebrate being can be a human, and the prompt can be provided by another human to the human or to a non-human vertebrate being capable of understanding the prompt, or trained to recognize the prompt. The other human can be a therapist. In addition, the prompt means can provide the prompt indirectly to the vertebrate being by first providing a direct prompt to the therapist or a trainer as the case may be, and then allowing the therapist or the trainer to provide a prompt to the vertebrate being.

The vertebrate being can be a mammal, and the muscle can be a muscle in a limb of the mammal. The vertebrate being can a human, and the muscle can be a muscle in a human limb.

The stimulator can be configured to apply a first voltage to the at least one active electrode and a second voltage to the at least one reference electrode simultaneously. Further, the stimulator can be configured to pass the electrical current flows through a plurality of paths as illustrated in FIGS. 10 and 11. The plurality of paths can include a first path between the motor cortex and one of the plurality of muscles (for example, as provided by the first stimulator unit and the second stimulator unit in FIG. 1 and a second path between two of the plurality of muscles (for example, as provided by the third stimulator unit). Each of the plurality of paths can run across the spinal column. In this case, at least one of the plurality of paths run across the spinal column.

In the system of the present disclosure, the stimulator can be configured to apply a first voltage to the at least one active electrode and a second voltage to the at least one reference electrode simultaneously. Further, the stimulator can include at least one stimulator unit configured to provide the electrical current by applying a first voltage to the at least one active electrode and a second voltage to the at least one reference electrode. In this case, the electrical current can be provided by the stimulator including at least one stimulator unit that applies the first voltage to the at least one active electrode and the second voltage to the at least one reference electrode to improve the neuromuscular condition of the vertebrate being.

The at least one stimulator unit can be configured to apply the first voltage and the second voltage simultaneously. In this case, the at least one stimulator unit can apply the first voltage and the second voltage simultaneously to improve the neuromuscular condition of the vertebrate being.

The at least one stimulator unit can include a plurality of stimulator units. A first stimulator unit can be configured to apply the first voltage and a second stimulator unit can be configured to apply the second voltage simultaneously with application of the first voltage by the first stimulator unit. Thus, the first voltage can be applied by a first stimulator unit and the second voltage can be applied by a second stimulator unit simultaneously.

The plurality of stimulator units can further include a third stimulator unit configured to deliver polarizing current between the brain of the vertebrate being and a muscle of the vertebrate. Polarizing current can be delivered between the brain of the vertebrate being and a muscle of the vertebrate being employing the third stimulator unit to improve the neuromuscular condition of the vertebrate being. The third stimulator unit can be synchronized with the first and second stimulator units so that the polarizing current is delivered simultaneously with the first voltage and the second voltages. Alternatively, the third stimulator unit can be configured to operate independently from the first and second stimulator units so that the polarizing current is delivered asynchronously from the first voltage and the second voltages. In this case, the third stimulator unit can be operated independently from the first and second stimulator units so that the polarizing current is delivered asynchronously from the first voltage and the second voltages.

The at least one stimulator unit can be a plurality of stimulator units including a stimulator unit configured to apply the first voltage and the second voltage simultaneously. The first voltage and the second voltage can be applied by a stimulator unit simultaneously. Another stimulator unit, such as the third stimulator unit, can be configured to deliver polarizing current between the brain of the vertebrate being and a muscle of the vertebrate being. In this case, polarizing current can be delivered between the brain of the vertebrate being and a muscle of the vertebrate being employing another stimulator unit. The other stimulator unit, e.g., the third stimulator unit, can be synchronized with the stimulator unit that delivers the first voltage and/or the second voltage so that the polarizing current is delivered simultaneously with the first voltage and the second voltages. Alternatively, the other stimulator unit can be configured to be operated independently from the stimulator unit so that the polarizing current is delivered asynchronously from the first voltage and the second voltages. In this case, the other stimulator unit is operated independently from the stimulator unit so that the polarizing current is delivered asynchronously from the first voltage and the second voltages to improve the neuromuscular condition of the vertebrate being.

In general, direct current (DC) stimulation is a non-invasive technique used to modulate the excitability of the central nervous system. When DC stimulation is delivered trans-cranially, a positively- or negatively-charged stimulating electrode (anode or cathode, respectively) is positioned at the cortical area to be stimulated, while a reference electrode is usually situated at a distance. Trans-cranial DC stimulation (tcDC) is used to modulate the excitability of the motor cortex, ameliorate the perception of pain, modulate cognitive functions, and/or treat depression. The effect of DC stimulation depends on the topography of neurons relative to the applied field, interactions between functional neuronal circuits, and the polarity of the electrode. For example, while cathodal stimulation depresses neuronal activity, anodal stimulation activates neurons.

The spinal cord contains various populations of excitatory and inhibitory interneurons that mediate cortical and sub-cortical inputs. By acting on these interneurons, as well as motoneurons and ascending and descending processes, DC stimulation at the spinal level could exert modulatory effects on cortical and sub-cortical inputs to the spinal cord. Although DC stimulation has been found to improve functional recovery after spinal cord injury, only a few studies have investigated the effects of trans-spinal direct current (tsDC) on the excitability of spinal neurons, and its effects on corticomotoneuronal transmission have never been investigated.

Research leading to the present disclosure show differential modulatory effects of tsDC polarity on spontaneous activity, which are shown below. Cortically-elicited triceps surae (TS) twitches were increased during cathodal trans-spinal direct current (c-tsDC), then depressed after termination, and were decreased during anodal trans-spinal direct current (a-tsDC), then potentiated after termination. While a-tsDC and rCES produced similar effects as a-tsDC alone, c-tsDC and rCES showed the greatest improvement in cortically-elicited TS twitches.

In one embodiment. DC stimulation can be employed to improve spinal responses to cortical stimulation. In many neurological disorders, connectivity between the cortex and spinal cord is compromised (e.g., spinal cord injury or stroke). Stimulation protocols can be employed to strengthen spinal responses. As illustrated in the studies described below, neuronal activity is important in shaping c-tsDC after-effects. Specifically, c-tsDC can optimize cortico-spinal activity during stimulation, and depress it at other times. The ability of c-tsDC to interact with conical activity to cause different outcomes is an interesting phenomenon that can support many clinical uses of c-tsDC. Translating this to rehabilitative strategies, either artificial cortical stimulation (when voluntarily muscle activation is impossible) or voluntary training during the application of c-tsDC can be employed to strengthen signal responses. Moreover, the depressive effect of c-tsDC can be used to manage spasticity resulting from many neurologic disorders.

C-tsDC can cause motoneurons to be more responsive to synaptic activation, but less inclined to generate spontaneous activity. This may explain why cortically-elicited TS twitches were potentiated during c-tsDC application. Moreover, pre-synaptic hyperpolarization has been shown to increase excitatory post-synaptic potentials (EPSPs). See Eccles J., Kostyuk, P. G., Schmidt, R. F., The effect of electric polarization of the spinal cord on central afferent fibres and on their excitatory synaptic action, J. Physiol. 162: 138-150 (1962); Hubbard J. I. and Willis W. D., Hyperpolarization of mammalian motor nerve terminals, J. Physiol. 163: 115-137 (1962); Hubbard J. I., and Willis W. D., Mobilization of transmitter by hyperpolarization, Nature 193: 174-175 (1962). Such hyperpolarization is expected to occur in cortico-spinal tract terminals and in spinal interneurons between the cortico-spinal tract and spinal motoneurons. Thus, nerve terminal hyperpolarization and dendrite depolarization induced by c-tsDC would cause potentiation of cortically-elicited TS twitches.

In a study leading to the present disclosure presented below, cortically-elicited TS twitches were depressed following c-tsDC and potentiated following a-tsDC. DC stimulation of the brain has similar results, as anodal stimulation increases while cathodal stimulation decreases the excitability of the motor cortex in humans and in mice. Anodal-induced excitability appears to depend on membrane depolarization, while cathodal-induced depression depends on membrane hyperpolarization. In addition, after-effects of both anodal and cathodal stimulation involve the N-methyl-D-aspartate (NMDA) glutamate receptor.

Figure 19:
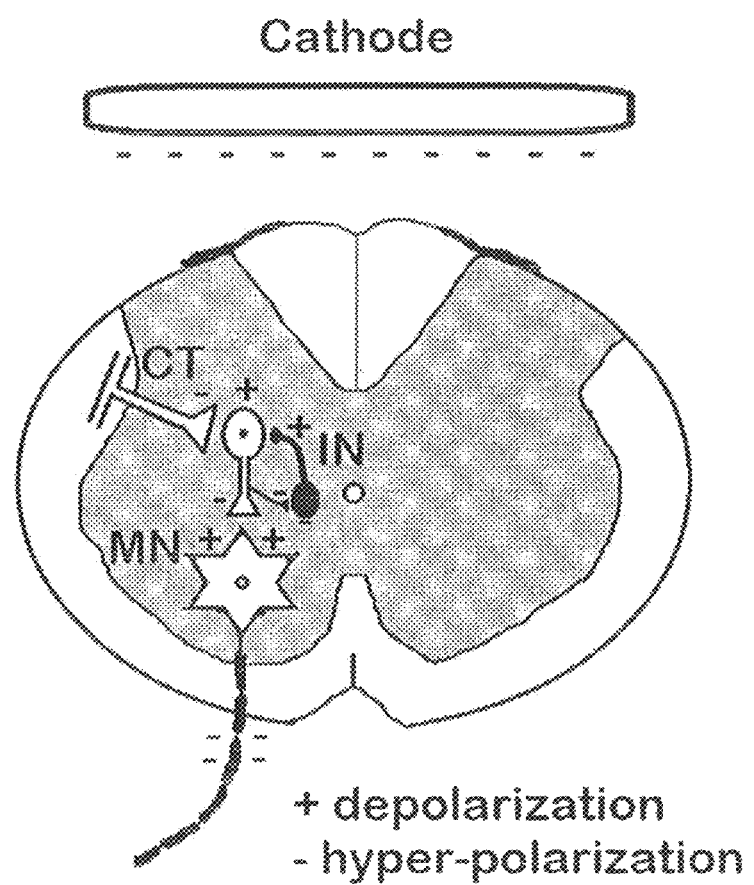
FIG. 19 is a hypothetical diagram illustrating possible changes in membrane potential when the spinal electrode negative delivers a polarizing current (not to scale).

Paining rCES with c-tsDC can not only prevent depression of cortically-elicited TS twitches after c-tsDC termination, but remarkably improve twitches C-tsDC seems to induce a polarizing pattern as shown in FIG. 19, including pre-synaptic hyperpolarization and post-synaptic depolarization within the corticomotoneuronal pathway.

In theory, neuronal compartments in close proximity to the negative electrode should depolarize, and distant compartments should hyperpolarize. Therefore, excitability of neurons with dendrites oriented dorsally and axons oriented ventrally should increase, and excitability of neurons oriented in the opposite direction (ventral to dorsal) should decrease. Reversing the direction of the polarizing current should result in opposite changes of membrane potential. The negative (−) and positive (+) signs indicate the status of the trans-membrane potential. CT, corticospinal tract; IN, interneuron; MN, motoneuron.

This pattern, combined with rCES, would evoke long-term potentiation. Specifically, pre-synaptic hyperpolarization has been shown to increase the size of EPSPs, which would subsequently increase neurotransmitter release and thereby cortical input. Although a low frequency stimulation was applied to the motor cortex in the study described below, the actual frequency of conical input was probably much higher. In addition, post-synaptic depolarization would activate the NMDA receptor. The association between pre-synaptic increase of neurotransmitter release and steady post-synaptic depolarization would trigger the induction of long-term potentiation. This could serve as the main mechanism for c-tsDC-induced enhancement of cortically-elicited TS twitches. Furthermore, reduction of inhibitory inputs to spinal circuits could also mediate the after-effects of paired rCES and c-tsDC.

First Experiment

A new configuration of electrical stimulation is provided herein as it was tested in anesthetized control and spinal cord injury (SCI) mice. Constant voltage output was delivered through two electrodes. While the negative voltage output (ranging from −1.8 to −2.6V) was delivered to the muscle (two-wire electrode, 500 μm), the positive output (ranging from +2.4 to +3.2V) was delivered to the primary motor cortex (M1) (electrode tip, 100 μm). The configuration was named dipolar cortico-muscular stimulation (dCMS) and consisted of 100 pulses (1 ms pulse duration, 1 Hz frequency).

In experimental testing, constant voltage output was delivered through two electrodes. While the negative voltage output (ranging from −1.8 to −2.6V) was delivered to the muscle, the positive output (ranging from +2.4 to 3.2V) was delivered to the primary motor cortex (M1). The configuration consisted of 100 pulses (1 ms pulse duration, 1 Hz frequency). In SCI animals, after dCMS, muscle contraction improved remarkably at the contralateral (456%) as well as ipsilateral (457%) gastrocnemius muscle. The improvement persisted for the duration of the experiment (60 min.). The enhancement of the muscle force was accompanied by the reduction of M1 maximal threshold and the potentiation of spinal motoneuronal evoked responses at the contralateral (313%) and ipsilateral (292%) sides of the spinal cord. Moreover, spontaneous activity recorded from single spinal motoneurons was substantially increased contralaterally (121%) and ipsilaterally (54%). Interestingly, spinal motoneuronal responses and muscle twitches evoked by stimulation of non-treated M1 (received no dCMS) were significantly enhanced as well. Similar results obtained from control animals albeit the changes were relatively smaller. These findings demonstrated that dCMS could improve functionality of motor pathway and dramatically attenuates the effects of spinal cord injury.

In SCI animals, after dCMS, muscle contraction improved markedly at the contralateral (456%) and ipsilateral (457%) gastrocnemius muscles. The improvement persisted for the duration of the experiment (60 min). The enhancement of the muscle force was accompanied by the reduction of M1 maximal threshold and the potentiation of spinal motoneuronal evoked responses at the contralateral (313%) and ipsilateral (292%) sides of the spinal cord. Moreover, spontaneous activity recorded from single spinal motoneurons was substantially increased contralaterally (121%) and ipsilaterally (54%). Interestingly, spinal motoneuronal responses and muscle twitches evoked by the test stimulation of non-treated M1 (received no dCMS) were significantly enhanced as well. Similar results obtained from control animals albeit the changes were relatively smaller. Conclusion. These findings demonstrated that dCMS could improve functionality of motor pathway and thus it may have therapeutic potential.

Methods

Animals

Specifically, experiments were carried out on CD-1, male and female adult mice in accordance with National Institute of Health ("NIH") guidelines. All protocols were approved by the College of Staten Island IACUC. Animals were housed under a 12 h light-dark cycle with free access to food and water.

Spinal Cord Contusion Injury

Mice were deeply anaesthetized with ketamine/xylazine (90/10 mg/kg i.p.). A spinal contusion lesion was produced (n=15 mice) at spinal segment T13 using the MASCIS/NYU impactor. 1 mm-diameter impact head rod (5.6 g) was released from a distance of 6.25 mm onto T13 spinal cord level exposed by a T10 laminectomy. After injury, the overlying muscle and skin was sutured, and the animals were allowed to recover under a 30° C. heating lamp. To prevent infection after the wound was sutured, a layer of ointment contained gentamicin sulfate was applied. Following surgery, animals were maintained under pre-operative conditions for 120 days before testing. The time of recovery was selected to ensure that animals developed a stable chronic spinal cord injury.

Behavioral Testing

Behavioral testing (n=15 animals with SCI) was performed 120 days post-injury to confirm that animals developed behavioral signs of locomotor abnormalities, spasticity syndrome, and sensorimotor incoordination at the hindlimbs. We have only used animals that demonstrated higher (proximately symmetrical in both hindlimbs) behavioral abnormalities. After acclimation to the test environment, three different testing procedures were used to quantify these behavioral problems.

Basso mouse scale (BMS): Motor ability of the hindlimbs was assessed by the motor rating of Basso mouse scale (BMS). The following rating scale was used: 0, no ankle movement; 1-2, slight or extensive ankle movement; 3, planter placing or dorsal stepping; 4, occasional planter stepping; 5, frequent or consistent planter stepping; no animal scored more than 5. Each mouse was observed for 4 min in an open space, before a score was given.

Abnormal pattern scale (APS): After SCI, animals usually developed muscle tone abnormalities that were exaggerated during locomotion and lifting the animal off the ground (by the tail). APS was developed to quantify the number of muscle tone abnormalities demonstrated by animals after SCI in two situations: on ground and off ground. The following rating scale was used: 0, no abnormalities; 1, for each of the following abnormalities: limb crossing of midline, abduction, and extension or flexion of the hip joint, paws curling or fanning, knee flexion or extension, ankle dorsi or planter flexion. The total score was the sum of abnormalities from both hindlimbs. The maximal score in APS was 12. Abnormal patterns were usually accompanied by spasmodic movements of the hindlimbs.

Horizontal ladder scale (HLS): For accurate placing for the hindlimb, animals had to have normal coordination between sensory and motor systems. For testing sensorimotor coordination, a grid with equal spacing (2.5 cm) was used. Animals were placed on the grid and were allowed to take 20 consecutive steps. Foot slips were counted as errors.

Electrophysiological Procedures.

Intact (n=10) and SCI (n=21) animals underwent a terminal electrophysiological experiment. Animals were anesthetized using ketamine/xylazine (90/10 mg/kg i.p.), which was found to reserve corticospinal evoked potential. Electrophysiological procedures started ~45 min after the first injection of anesthesia to perform the experiments at intermediate to light levels of anesthesia, as recommended by Zandieh and colleagues. See Zandieh S., Hopf R., Redl H., Schlag M. G., The effect of ketamine/xylazine anesthesia on sensory and motor evoked potentials in the rat. Spinal Cord, 41:16-22 (2003). This was determined by the presence of front or hind limb withdrawal reflex. As needed, anesthesia was kept at this level using supplemental dosages (~5% of the original dose).

The entire dorsal side of each animal was shaved. The skin covering the two hindlimbs, lumbar spine, and the skull was removed. The two gastrocnemii muscles (right and left) were carefully separated from the surrounded tissue preserving blood supply and nerves. The tendon of each of the muscles was threaded with a hook shaped 0-3 surgical silk, which was connected to the force transducers. Next, a laminectomy was performed in the 2nd, 3rd, and 4th lumbar vertebrae (below the lesion in animals with SCI); the 13th rib was used as a bone land mark to identify the level of spinal column. Since spinal cord levels are ~3 levels displaced upward relative to vertebral levels, the recording was assumed to be performed at spinal cord levels: 5th and 6th lumbar and 1st sacral. A craniotomy was made to expose the primary motor cortex (M1) (usually the right M1) of the hindlimb muscles located between 0 to −1 mm from the Bregma and 0 to 1 mm from midline. The dura was left intact. The exposed motor cortical area was explored with a stimulating electrode to locate the motor point from which the strongest contraction of the contralateral gastrocnemius muscle was obtained using the weakest stimuli. In experiments aimed to test the effect of dCMS on nonstimulated motor pathway, two craniotomies were made over the right and left hind limb areas of M1.

Both hind and fore limbs and the proximal end of the tail were rigidly fixed to the base. Both knees were also fixed into the base to prevent transmitting any movement from stimulated muscles to the body and vice versa. Muscles were attached to force displacement transducers and the muscle length was adjusted to obtain the strongest twitch force (optimal length). The head was fixed in a custom made clamping system. The whole setup was placed on an anti-vibration table. Animals were kept warm during the experiment with radiant heat.

A stainless steel stimulating electrode (500 µm shaft diameter, 100 µm tip) was set on the exposed motor cortex. Paired stainless steel stimulating electrode (~15 mm spacing; 550 µm diameter) was placed on the belly of the gastrocnemius muscle. The same electrode was alternated between left and right muscles according to experimental procedure. Electrodes were then connected to stimulator outputs. Extracellular recordings were made with pure iridium microelectrodes (0.180 shaft diameter; 1-2 µm tip; 5.0 MΩ). Two microelectrodes were inserted through two small openings that were carefully made into the spinal dura matter on each half (right and left) of the spinal cord. The insertion was made at approximately the same segmental level of the spinal cord. Reference electrodes were placed in the tissue slightly rostral to the recording sites. The ground electrodes were connected to the flap of skin near the abdomen. Motorized micromanipulators were used to advance the microelectrodes into the ventral horns. Extracellular activity was passed through a standard head stage, amplified, filtered (bandpass, 100 Hz to 5 KHz), digitized at 4 KHz, and stored in the computer for further processing. A power lab data acquisition system and LabChart 7 software by ADInstruments, Inc, CO, USA were used to acquire and analyze the data.

Once a single motoneuron was isolated at the left and right side of the spinal cord, few antidromic pulses (range, −9 to −10 V) were applied to the homonymous gastrocnemius muscle. As described by Porter, the presence of antidromically-evoked response with a short latency (3.45 ms) indicated that the recording electrode was placed in the vicinity of the neuron innervating stimulated muscle. See Porter R., Early facilitation at corticomotoneuronal neuronal synapses. J. Physiol. 207:733-745 (19700. These recordings were also used to calculate the latency of ipsilateral and contralateral spinal responses to muscle stimulation. A cortical pre-test stimulation of 10 pulses (anodal monopolar) at maximal stimulus strength (usually +8 to +10V) was applied to the primary motor cortex (M1). Maximal stimulus strength was defined as the strength of stimulation when no further increase in muscle contraction was observed. This was also used to calculate the maximal threshold of M1 stimulation.

Next, dCMS was applied through two electrodes as shown in FIG. 1A. The positive and negative voltage outputs were connected to electrodes situated on the primary motor cortex (M1), and on the contralateral gastrocnemius muscle, respectively. Each of the two gastrocnemii muscles was attached to a force transducer (not shown). Recording from single motoneuron (Rec) was performed simultaneously on each side of the spinal cord below the lesion. In FIG. 1A, IGM represents the ipsilateral gastrocnemius muscle, and CGM represents the contralateral gastrocnemius muscle.

Specifically, the negative output was connected to an electrode situated on the gastrocnemius muscle and the positive electrode was at M1. The voltage strength and polarity were computer-controlled. The strength of dCMS stimulation was adjusted so that contraction of the ipsilateral muscle (to M1) was at maximal strength which was reached just before the appearance of tail contraction (visually observed). This level of response was achieved by simultaneously applying a negative output (range, −2.8 to −1.8 V) to the muscle and positive output (range, +2.2 to +3.2 V) to M1. At this maximal strength, dCMS was delivered (100 pulses, 1 ms pulse duration, 1 Hz frequency), 15 to 20 seconds after the stimulating paradigm was ended, a post-test (with identical parameters as pre-test) stimuli were delivered to M1.

Figure 1B:
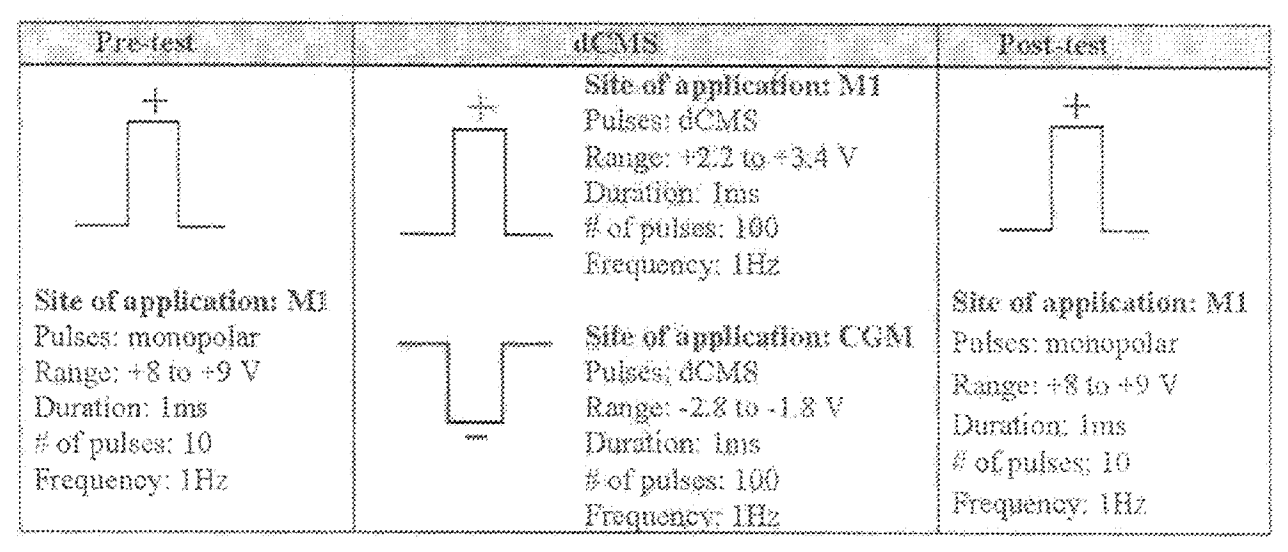

FIG. 1B shows the experimental design for the pulsing, range, duration, number of pulses, and frequency. The experimental procedure included three phases designed to stimulate the preparation and to evaluate its reactions to dCMS. The force of muscle contraction and cortically-evoked spinal responses were evaluated before and after the application of dCMS in Pre-test and Post-test phases by application of ten monopolar pulses. The type of stimulation and location of the stimulation and recording electrodes was the same in these two phases. During dCMS phase the preparation was stimulated by application of the positive and negative pulses to the motor cortex (M1) and contralateral gastrocnemius muscle (CGM) respectively. While the number of pulses delivered during Pre- and Post-test phases was the same (10), the number of pulses delivered during dCMS was 100. The duration (1 ms) and the frequency of stimulation (1 Hz) were the same in all three phases of the experiment. The shape of the stimulating current at each phase is shown. There was a continuous recording of ipsilateral and contralateral muscle twitches and evoked and spontaneous spinal activity during the entire experiment.

Spontaneous activity was followed for 5 min, then the experiment was ended and animals were injected with a lethal overdose of anesthesia. In a subgroup of animals, the maximal threshold of M1 was re-tested. In addition, in this subgroup, in order to determine the long lasting effect of dCMS, the magnitude of cortically-evoked muscle twitches and spinal responses were retested every 20 min for 60 min after dCMS.

White Matter Staining

At the end of each experiment, animals were injected with a lethal dose of Ketamine. Two parts of the spinal column (including vertebrae and spinal cord) were dissected, one part (1.5 cm) included the lesion epicentre and another part (~0.5 cm) included the recording area (to confirm the electrodes location). Tissues were kept overnight (4° C.) in 4% paraformaldehyde in 0.1 m PBS and cryoprotected in 20% sucrose in PBS at 4° C. for 24 h. The spinal column was freeze mounted and cut into 30 µm sections and placed on poly-L-lysine-coated glass slides. The spinal column part including the lesion epicentre was sequentially sectioned from rostral. Slides were numbered to identify their locations relative to the lesion epicentre.

Four slides from each SCI animal (n=6) containing the lesion epicentre and two slides containing no signs of damaged spinal cord tissue from above and below the lesion were taken for luxol fast blue (Sigma) staining. The lesion epicentre was identified as the section containing the least amount of Luxol fast blue. Sections from control animals (n=3) at spinal cord T13 level were stained with luxol fast blue. Sections from the recording area were stained with cresyl violet.

The amount of spared white matter was measured using Adobe Photoshop CS4 by Adobe Systems, San Jose, Calif., USA. To assess the extent of the spinal cord damage, the spared white matter at the lesion epicentre was compared with the white matter at spinal cord level T13 in control animals.

Data Analysis

To evaluate the latencies, the time was recorded from the start of the stimulus artifact to the onset of the first deflection of spinal response. Measurements were made with a cursor and a time meter on LabChart software. The amplitude of spinal responses was measured as peak-to-peak. Analysis of muscle contractions were performed with peak analysis software by ADInstruments. Inc, CO, USA, as the height of twitch force measured relative to the baseline. Spike Histogram software was used to discriminate and analyze extracellular motoneuronal activity. All data were reported as group means±standard deviation (SD). Paired student's t-test was performed for before-after comparison or two sample student's t-test to compare two groups; statistical significance at the 95% confidence level ($p<0.05$). To compare responses from both sides of spinal cords recorded from control animals and from animals with SCI, one way ANOVA was performed followed with Solm-Sidak post hoc analysis. Statistical analyses were performed using SigmaPlot (SPSS, Chicago, Ill.), Excel (Microsoft, Redwood, Calif.), and LabChart software (ADInstruments, Inc, CO. USA).

Results

1. Behavioral Assessment.

A contusion lesion of the spinal cord resulted in the appearance of signs of spasticity syndrome such as crossing of both limbs and fanning of the paws (compare 2A and 2C). These postural changes were quantified using the abnormal pattern scale (APS). APS showed substantial increase for both on ($APS_{on}$ 9.8±0.70) and off ($APS_{off}$ 9.8±0.70) ground conditions. These postural abnormalities were also accompanied by reduction in Basso Mouse Scale (BMS) scores from 9 in control mouse to 1.2±0.47 and 1.0±0.63 for right and left hindlimb in SCI mouse (n=15), respectively. In addition, the number of errors on a horizontal ladder test was close to maximum (20) for left (19.5±0.50) and right (18.83±1.16) hindlimb. Collectively, these results indicate that spinal cord injury procedure used in the current study was reliable in inducing behavioral signs of the injury. This strengthens the interpretation of our data.

2. Anatomical Assessment.

Figure 2A:
FIG. 2A is a photograph of a control animal showing the normal posture of the hind limbs.
Figure 2B:
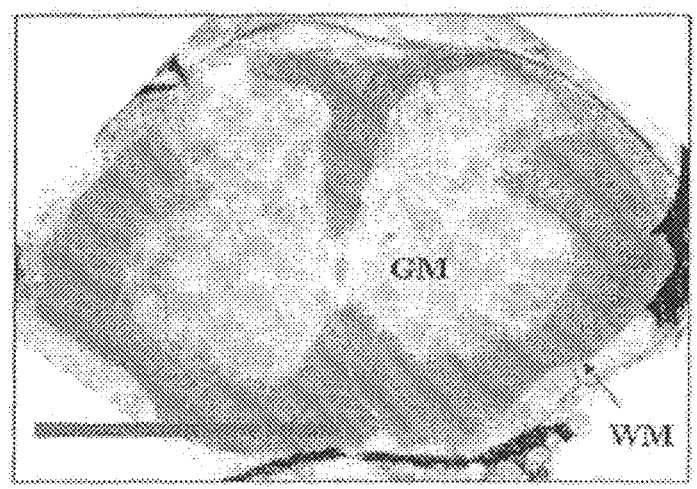
FIG. 2B is a photograph of spinal cord cross-sectional slice taken from the thoracic level of a control animal, wherein WM is white matter and GM is gray matter.
Figure 2C:
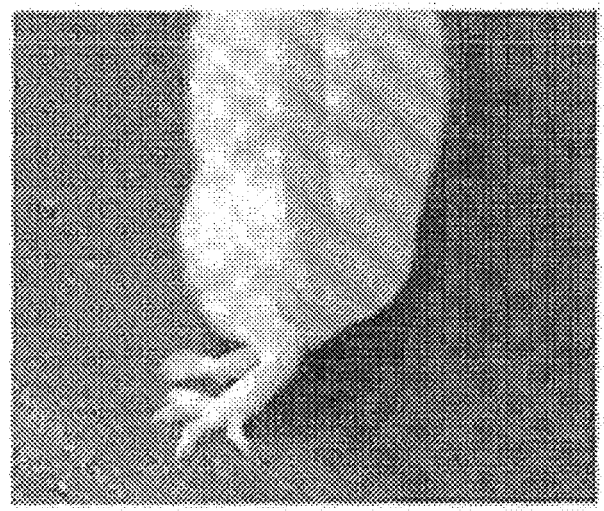
FIG. 2C is a photograph of an animal with SCI showing the abnormal pattern of the hind limbs.
Figure 2D:
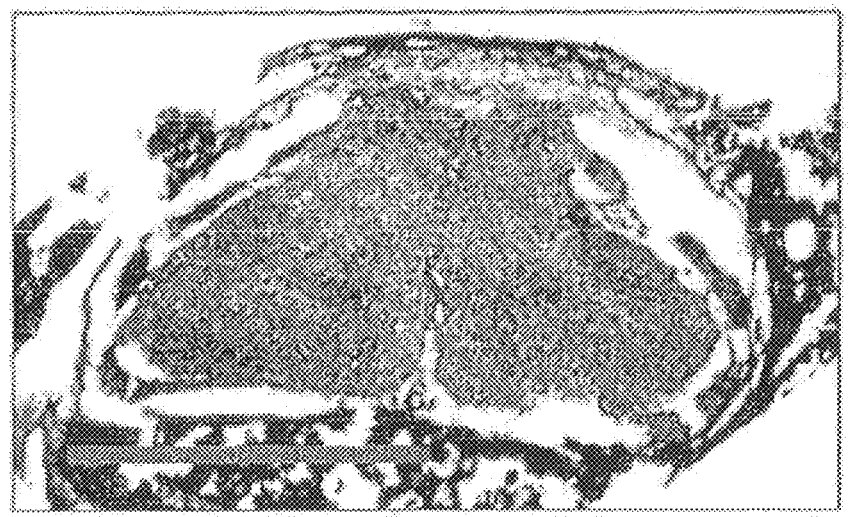
FIG. 2D is a photograph of a spinal cord cross-sectional slice taken from the thoracic level of an animal with SCI showing the lesion epicenter.
Figure 2E:
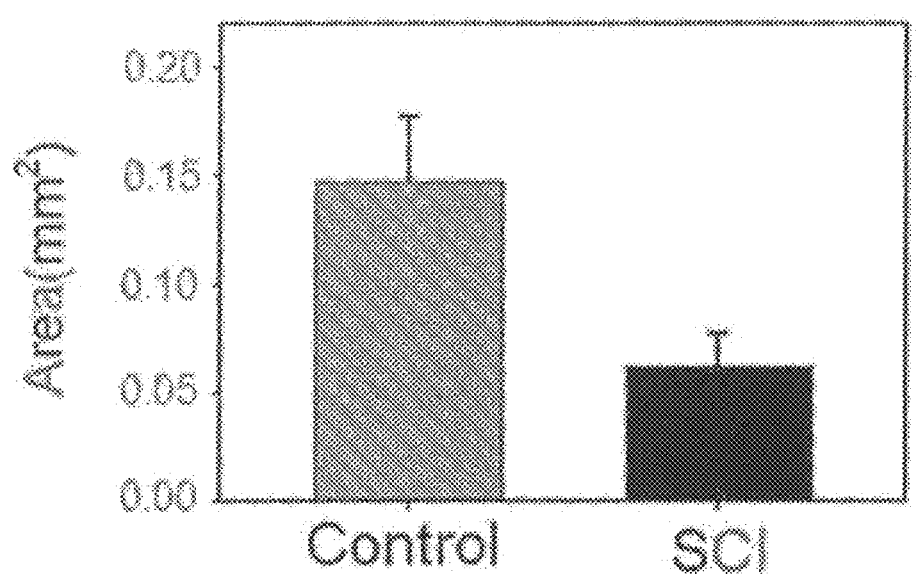
FIG. 2E is a graphical representation of a quantification of spared white matter at the lesion epicenter of animals with SCI and control animals.

FIG. 2A is a photograph of a control animal showing the normal posture of the hindlimbs. FIGS. 2B and 2D show photographs of cross-sectional slices from the thoracic spinal cord region and the lesion epicentre taken from normal and SCI animals, respectively. The lesion size was proximally equal in all injured animals tested histologically (n=6). A rim of white matter was spared on the lateral and ventral side of the spinal cord. The area of spared white matter at the lesion epicentre (0.06±0.03 mm2) was significantly reduced 16 weeks after SCI compared to the area of white matter at the same spinal level (0.15±0.06 mm2) in control animals (n=3) (p=0.04, t-test), FIG. 2E. On average, the total cross-sectional area (white and gray matters) of the lesion epicenter was 75±14% of the total cross-sectional area of the same spinal level in control animals.

3. Spinal Motor Neuron Identification.

Spinal motoneurons (or motor neurons) innervating the gastrocnemius muscle were at first identified by their large spontaneous spikes. The motoneuronal spike was also accompanied by a distinctive and crisp sound recorded with a loud speaker. Second criterion used to identify spinal motoneurons was their response to the stimulation of the gastrocnemius muscle. Stimulating the gastrocnemius muscle produced a short latency antidromically-generated response that was recorded from motor neurons in the ipsilateral spinal cord. Simultaneously, the microelectrode on the contralateral side of the spinal cord recorded a response that had relatively longer latency than the one picked up from the ipsilateral side. In FIG. 3A, three representative conditions were seen during the identification of motoneurons. The two panels, far left and middle, show simultaneous motoneuronal responses to stimulated gastrocnemius muscle. The far left panel shows the response of the motoneuron in the ipsilateral side. The middle panel shows the response of the motoneuron in the contralateral side. The far right panel shows a situation when the motoneuron was not responding to the antidromic stimulation of the homonymous gastrocnemius muscle. This confirmed that the unit was not innervating the stimulated gastrocnemius muscle. Third, as depicted in FIG. 3 B the muscle twitches (lower panel) were correlated with motoneuron activity (upper panel). This association between spontaneous spikes and muscle twitches was used to confirm the connection. FIG. 3I shows typical spike generated by motoneuron. Finally, it was histologically confirmed that recording electrodes were localized in the ventral horn of the spinal cord.

4. Latencies.

Figure 4A:
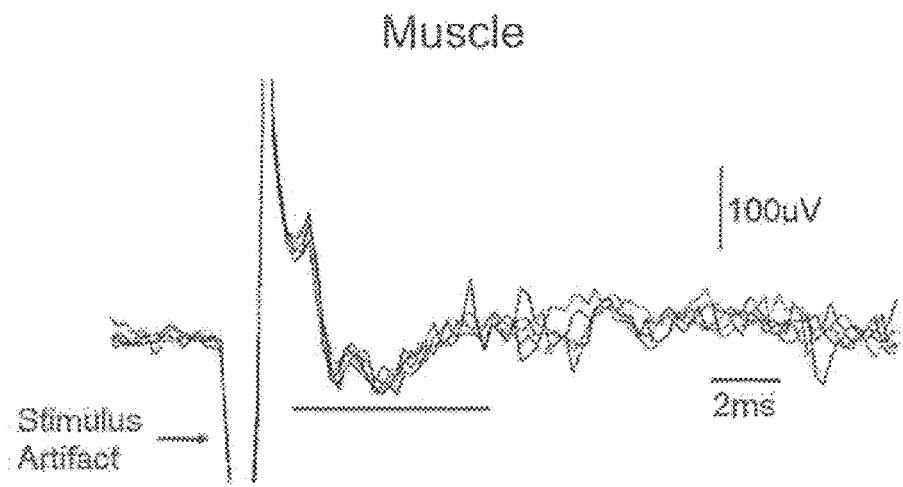
FIG. 4A is an illustration of six superimposed spinal responses after homonymous gastrocnemius muscle stimulation.

Stimulating the gastrocnemius muscle resulted in short and long latency spinal responses recorded by microelectrodes placed in the ipsilateral and contralateral ventral horns of the spinal cord, respectively. FIG. 4A shows superimposed traces of 6 antidromically-evoked responses, and the line marks the spinal responses. While the average latency of antidromically-evoked responses was 3.45±1.54 ms, the average latency of the contralateral responses (not shown) was longer (5.94±1.24 ms) indicating a transynaptic pathway. The difference between ipsilateral and contralateral spinal responses was statistically significant (n=15, $p<0.001$, t-test). Stimulating M1 resulted in ipsilateral and contralateral spinal motoneuronal responses.

Figure 4B:
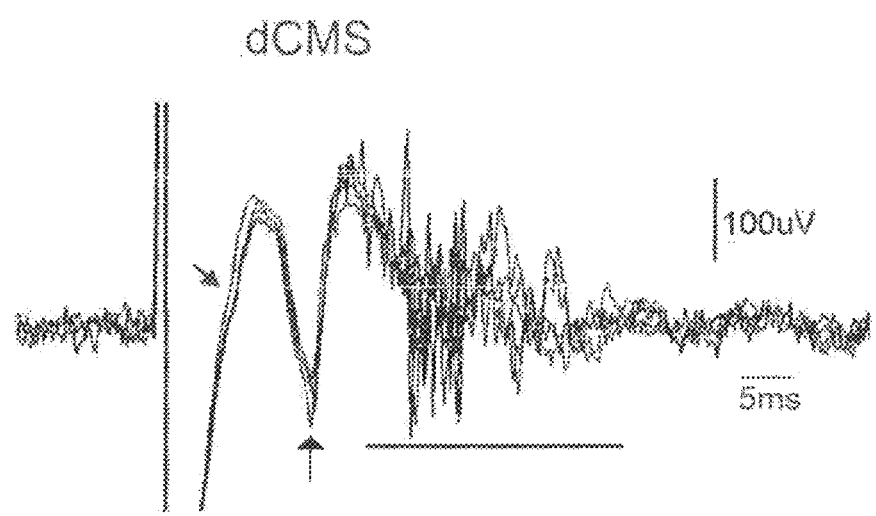
FIG. 4B is an illustration of six superimposed spinal responses after motor cortex (M1) stimulation.

FIG. 4B shows six superimposed contralateral responses after M1 stimulation. The ipsilateral response is not shown in FIG. 4A or 4B. The average latency of ipsilateral and contralateral responses was 16.09±1.02 ms and 22.98±1.96 ms, respectively. The difference in latency between ipsilateral and contralateral responses (6.9 ms) was statistically significant (n=15, $p<0.001$, t-test). The application of dCMS resulted in successive spinal motoneuronal responses picked up from the contralateral (to M1) electrode.

Figure 4C:
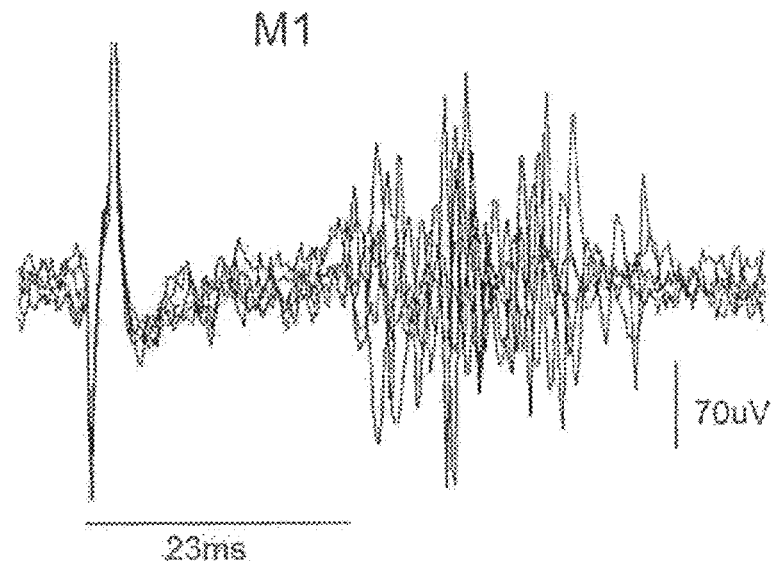
FIG. 4C is an illustration of six superimposed spinal responses after dCMS.

FIG. 4C shows six superimposed recorded traces. In FIG. 4C, three distinctive responses are seen, one with short latency (3.45±1.54 ms), the second with longer latency (6.02±1.72 ms), and a third with much longer latency (19.21±2.28 ms) (n=15). The latency of the ipsilateral (to M1) spinal motoneuronal responses (not shown) was 6.02±2.8 ms.

Figure 4D:
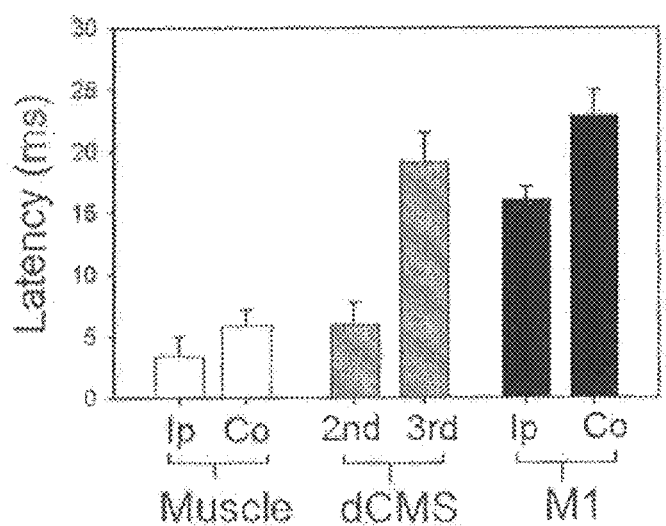
FIG. 4D is a graphical representation of the average latency of spinal responses after muscle stimulation, dCMS, and after M1 stimulation.

FIG. 4D summaries the average latencies collected during muscle. M1, and dCMS paradigms. Ipsilateral spinal response to M1 stimulation (Ip) was faster than the contralateral response (Co) ($p<0.05$). Muscle stimulation generated shorter response at ipsilateral motoneuron than the ones at the contralateral side ($p<0.05$).

5. Changes in Muscle Contraction and Spinal Responses During Dipolar Cortico-Muscular Stimulation (dCMS).

The application of dCMS gradually increased the twitch peak force recorded from the gastrocnemii muscles and neuronal activity recorded from the spinal cord. Since the magnitude of these enhancements were similar in control and injured animals, only data obtained from SCI animals (n=9) are presented. The increase in the force of the contralateral muscle contraction is shown in FIGS. 5A and 5B.

Figure 5A:
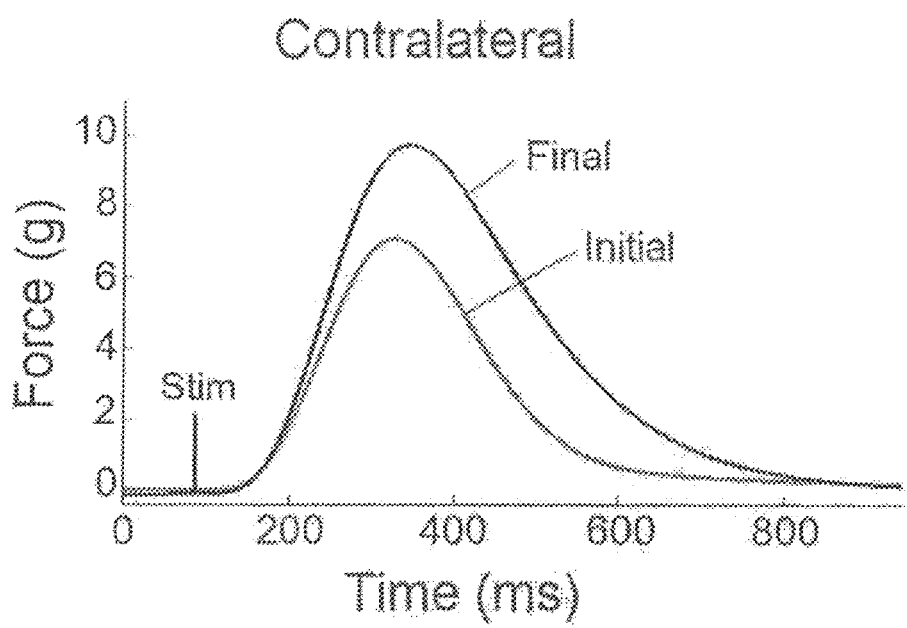
FIGS. 5A and 5B are graphical representations of contraction for the contralateral muscle during dCMS in animals with SCI.
Figure 5B:
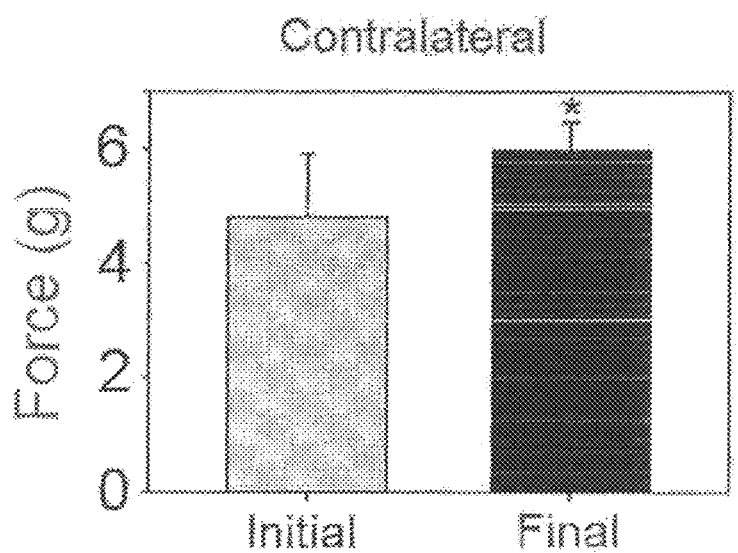

FIG. 5A shows that initial and final muscle twitches demonstrated greater twitch peak force at the end (final) than the beginning (initial) of dCMS on the contralateral muscle to stimulated M1. While FIG. 5A depicts representative recordings, the averaged results obtained from all 9 SCI animals are shown in FIG. 5B. The increase from an initial twitch peak force of 4.8±1.12 g to a final twitch peak force of 6.1±0.71 g was statistically significant (percent change=25.0±3.8%, p=0.001, paired t-test). The twitch peak force of ipsilateral muscle increased as well.

Figure 5C:
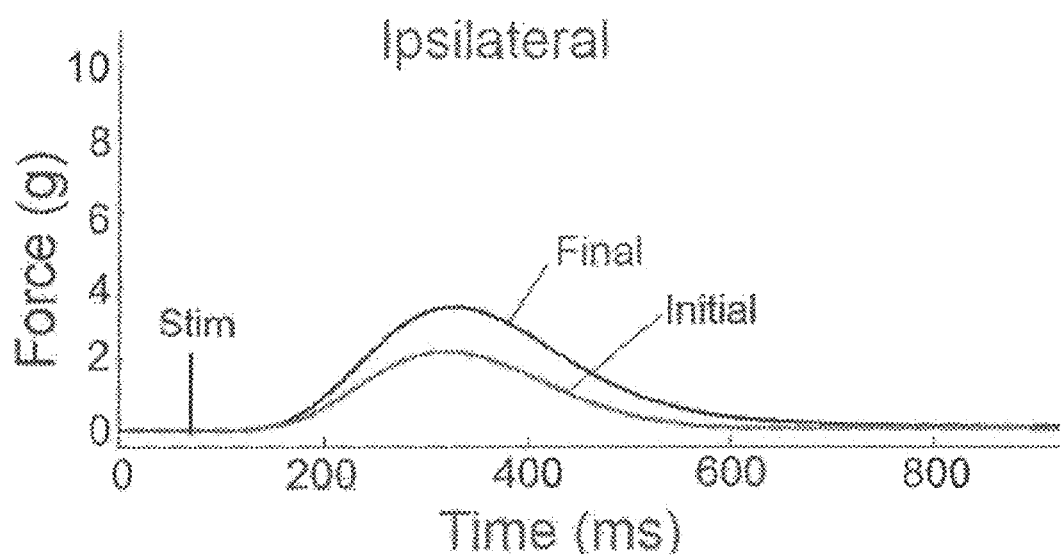
FIGS. 5C and 5D are graphical representations of contraction for the ipsilateral muscle during dCMS in animals with SCI.
Figure 5D:
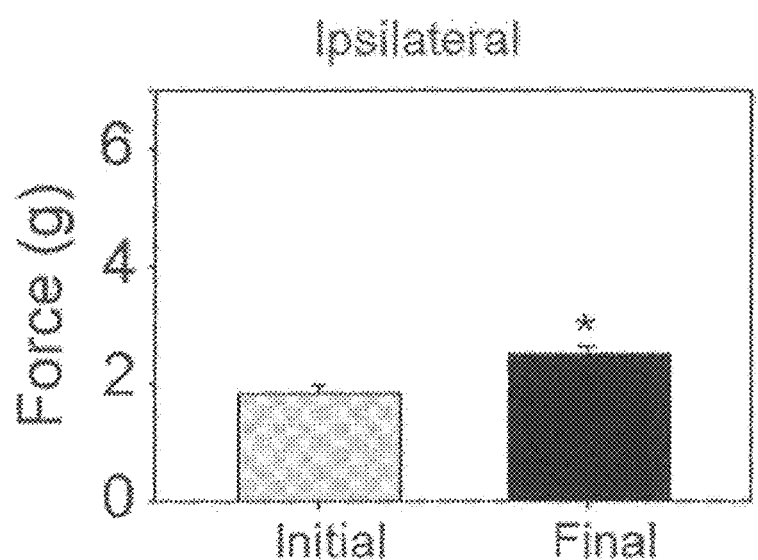

Representative recordings and averaged results are shown in FIGS. 5C and 5D. FIG. 5C shows initial and final muscle twitches of the ipsilateral muscle (to stimulated M1) during dCMS, which demonstrated an increase in twitch force in response to dCMS. FIG. 5D is a bar graph showing averages (n=9) of initial and final twitch peak force of the ipsilateral muscle. The final twitch force increased significantly from its initial value of 1.8±0.74 g (percent change=37.7±1.14%; p=0.001, paired t-test).

Similar results were obtained by comparing the first and the last spinal motoneuronal responses of the 100 pulses of dCMS protocol. On average, the contralateral (to stimulated M1) spinal motoneuronal responses showed significant increase (percent change=49.75±16.9%, p=0.013, one sample t-test), as did the ipsilateral (to stimulated M1) spinal motoneuronal responses (percent change=48.10±19.8%, p=0.04, one sample t-test). These findings suggest that physiological processes that mediate stronger connections of the corticomotoneuronal pathway were initiated during dCMS application.

6. The Influence of dCMS Application on Muscle Twitches and Neuronal Activity in SCI Animals.

Figure 6A:
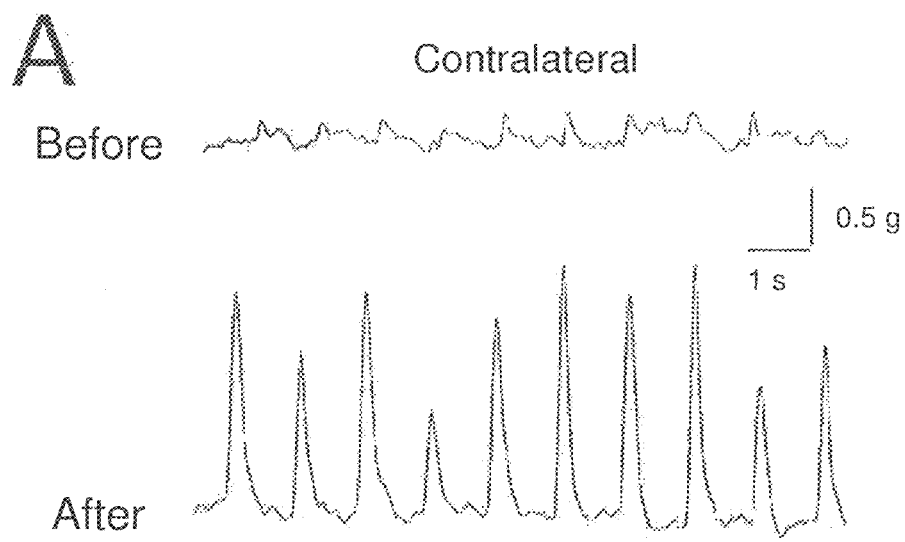
FIGS. 6A and 6B show a plot of contralateral gastrocnemius muscle activity after dCMS (contaralateral) in animals with SCI.
Figure 6B:
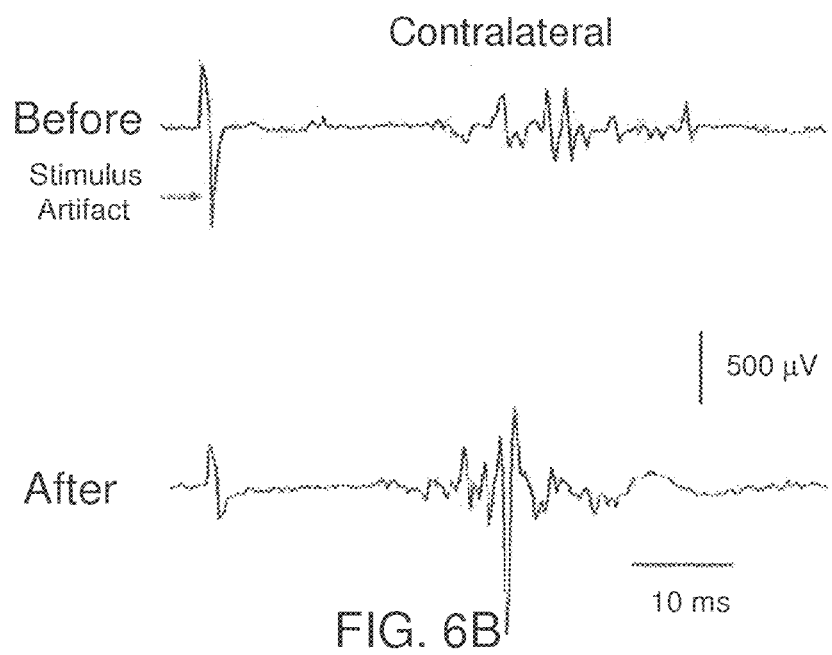
Figure 6C:
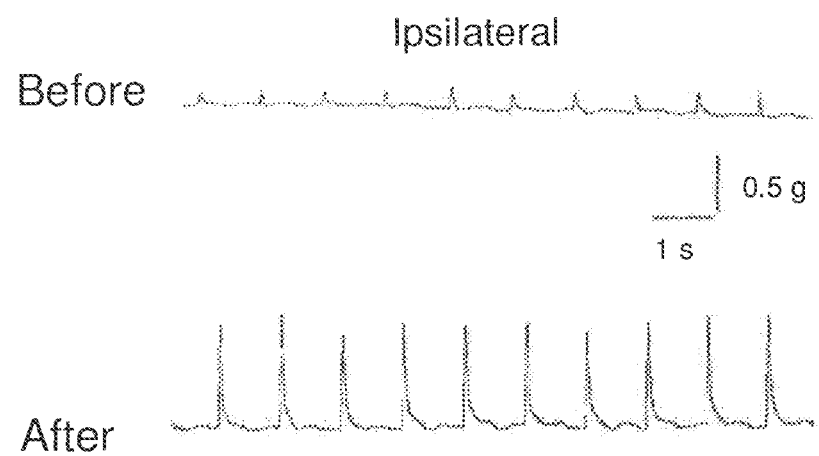
FIGS. 6C and 6D show a plot of contralateral gastrocnemius muscle activity after dCMS (contaralateral) in animals with SCI.
Figure 6D:
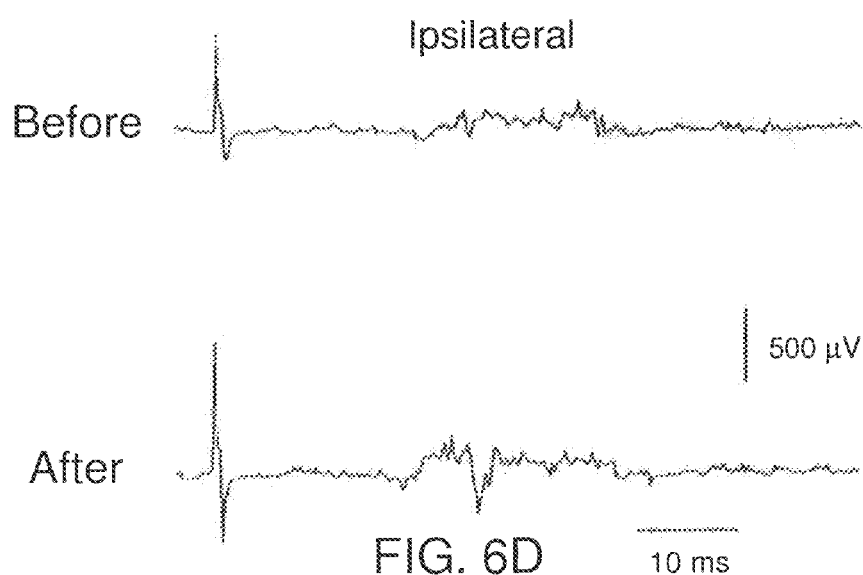

Cortically induced muscle twitches (measured as peak twitch force) were examined before and after dCMS in SCI animals. In all animals used in these experiments, twitch force was remarkably increased after dCMS. An example of twitches of the contralateral (to stimulated M1) (FIG. 6A) and ipsilateral (to stimulated M1) (FIG. 6C) gastrocnemius muscles before (upper panels) and after (lower panel) dCMS are shown in FIGS. 6A and 6C. The cortically induced spinal responses (measured as peak-to-peak) were also examined, which also substantially increased. Examples of contralateral (FIG. 6B) and ipsilateral (FIG. 6D) spinal responses are shown.

Figure 6E:
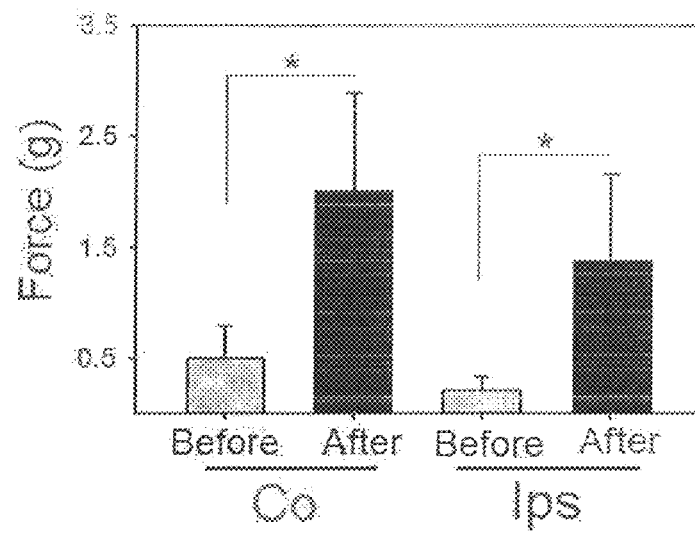
FIGS. 6E and 6F are graphical representations of muscle twitch force before and after dCMS in animals with SCI (contralateral and ipsilateral).
Figure 6F:
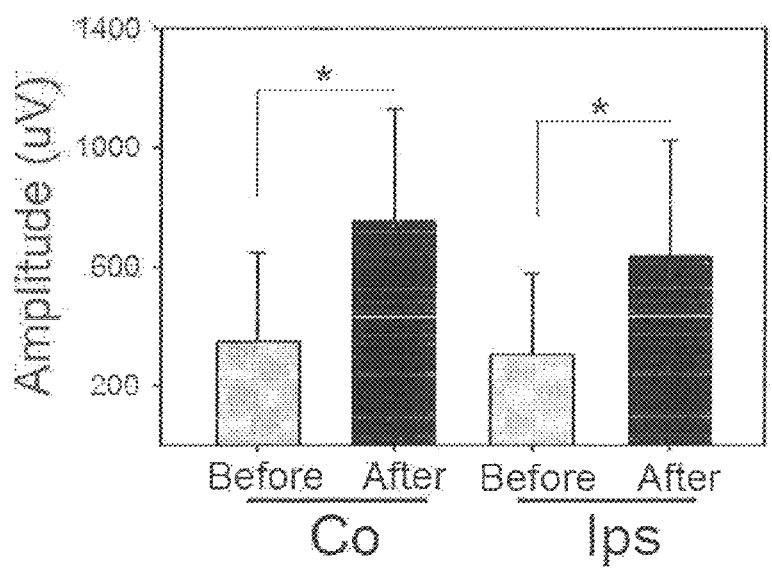

In FIG. 6E, the twitch peak force of the contralateral muscle showed significant increase (n=9; p<0.001) (average before=0.50±0.28 g vs. average after=2.01±0.80 g) after dCMS, as did the twitch peak force of the ipsilateral (to stimulated M1) muscle (average before=0.21±0.12 vs. average after=1.36±0.77, p<0.001, paired t-test). In FIG. 6F, spinal motoneuronal responses (n=9) contralateral (to stimulated M1) showed significant increase after dCMS (average before=347.67±294.68 µV vs. average after=748.90±360.59 µV, p=0.027, paired t-test) (increased by 313±197%), as did ipsilateral (to stimulated M1) spinal motoneuronal responses (average before=307.13±267.27 µV vs. average after=630.52±369.57 µV, p=0.001, paired t-test) (increased by 292±150%). Data are shown as means±SD. These results show that dCMS greatly potentiates the motor pathway in injured animals.

The maximal cortical threshold defined as the lowest electrical stimulus eliciting the strongest muscle twitch peak force was reduced from 9.4±0.89 V to =5.7±0.95 V after dCMS application (n=4, p<0.001, t-test). The muscle twitch force and the magnitude of spinal motoneuronal responses, evaluated 60 min after dCMS in 5 SCI animals, were still significantly elevated on both sides (repeated measure ANOVA followed with post hoc, p<0.001).

7. Effects of dCMS on the Nonstimulated Cortico-Muscular Pathway in Animals with SCI.

The test stimulation of the other M1, contralateral to M1 where dCMS has been applied, revealed an increase of the contraction force recorded from contralateral and ipsilateral gastrocnemii muscles. The increase in contralateral (percent change=182.8±87.18%), and ipsilateral muscles (percent change=174.8±136.91%) was statistically significant (n=6, p<0.05, t-test).

Contralateral spinal motoneuronal response was increased significantly (p=0.006, t-test) (average percent change=373.8±304.99%), as did ipsilateral (average percent change=289.2±289.62%, p=0.025, t-test). These results indicate that even though dCMS was unilaterally applied, it affected the cortico-muscular pathway bilaterally.

8. The Influence of dCMS Application on Muscle Twitches and Neuronal Activity in Control Animals.

Figure 7A:
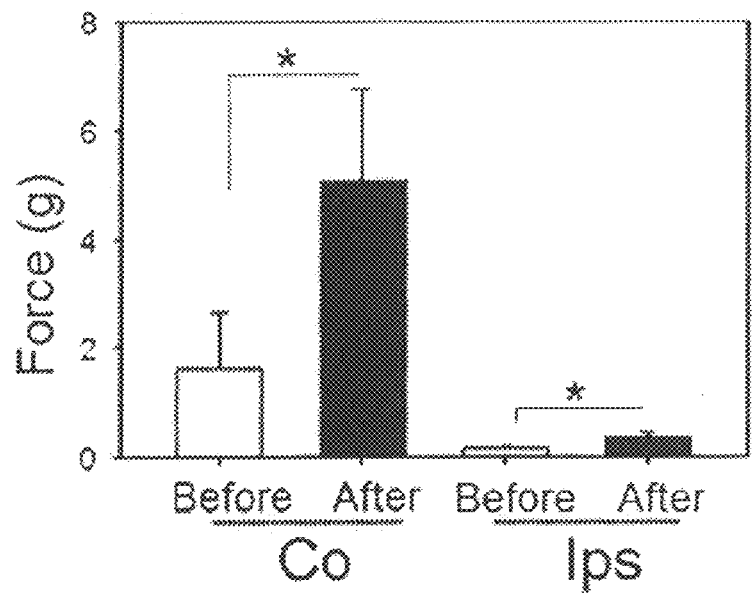
FIGS. 7A and 7B are graphical representations of muscle twitch force before and after dCMS in control animals.
Figure 7B:
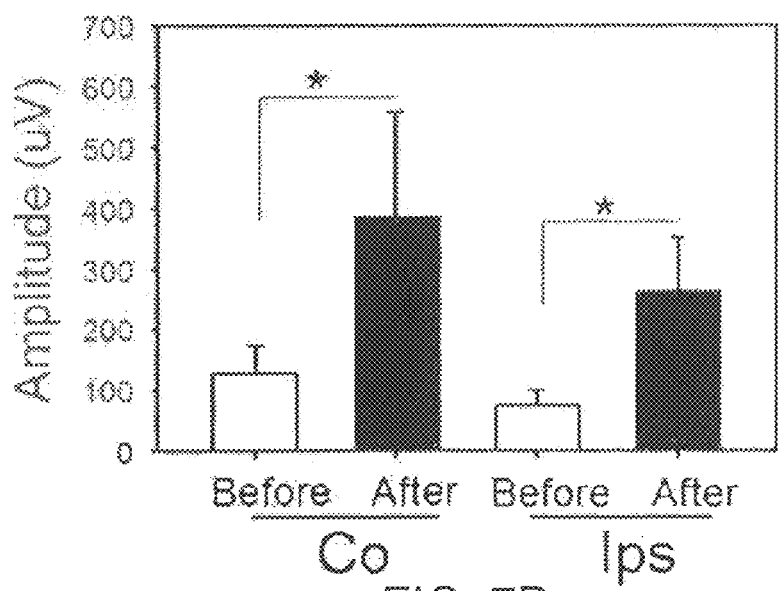

The application of dCMS across the cortico-muscular pathway in control animals (n=6) resulted in an increase in the contraction force produced by both gastrocnemii muscles. FIGS. 7A and 7B show twitch force and cortically evoked spinal responses after dipolar cortico-muscular stimulation (dCMS) in normal mice. FIG. 7A is a quantification of results from 6 control animals, which revealed significant increase in contralateral (CO) and ipsilateral (Ips) (to stimulated M1) muscle twitch force after dCMS. FIG. 7B shows contralateral (to stimulated M1) cortically evoked spinal responses, which significantly increased after dCMS, as did ipsilateral responses. The twitch peak force of the contralateral muscle increased from 1.62±1.0 g before to 5.12±1.67 after dCMS application (percent change=250.75±129.35%, p=0.001, paired t-test. FIG. 7A). The twitch peak force of the muscle on the ipsilateral side increased as well, although the increase was less pronounced (from 0.16±0.05 g to 0.39±0.08 g, before and after dCMS, respectively (percent change=166.36±96.56%, p=0.001, paired t-test, FIG. 7A).

The amplitude of evoked responses recorded from spinal motoneurons was also enhanced by dCMS application. As depicted in FIG. 7B, the average amplitude of these spikes recorded at the contralateral side increased from 127.83±46.58 µV to 391.17±168.59 µV (percent change=168.83±152.00%, p=0.009, paired t-test). The increase at the ipsilateral side was even greater (percent change=369.00±474.00%, 77.50±24.73 µV before versus 267.00±86.12 µV after dCMS, p=0.007, paired t-test).

9. Comparison Between Control and SCI Animals.

The cortically-induced twitches of the contralateral muscle, recorded from control animals were stronger than twitches observed in SCI animals regardless of whether they were recorded before (p=0.009, t-test), or after (p=0.001, t-test) the dCMS procedure. The response of ipsilateral muscles, however, was more complex. Before dCMS, SCI animals showed higher ipsilateral twitch peak force than control animals, although the difference was not statistically significant (p=0.39, t-test). This difference was significantly enhanced after dCMS intervention (p=0.01, t-test).

Similarly, before dCMS, the cortically-induced responses recorded from spinal motoneurons were higher in SCI animals at ipsilateral and contralateral sides, although the difference did not reach statistical significance (p=0.13, t-test). However, following dCMS, this difference was increased and became statistically significant (p=0.009, t-test).

Next a relative measure was obtained, which was characterized as a "fidelity index". Fidelity index (FI) is the normalized conically induced spinal motoneuronal response to the corresponding muscle twitch peak force (spinal response/muscle twitch ratio). Lower fidelity index value indicates better association between spinal responses and their corresponding muscle twitches. In other words, it means better ability of a spinal response to induce muscle contraction. Therefore, changes in this index may indicate changes in relation between spinal and peripheral excitability.

Figure 8:
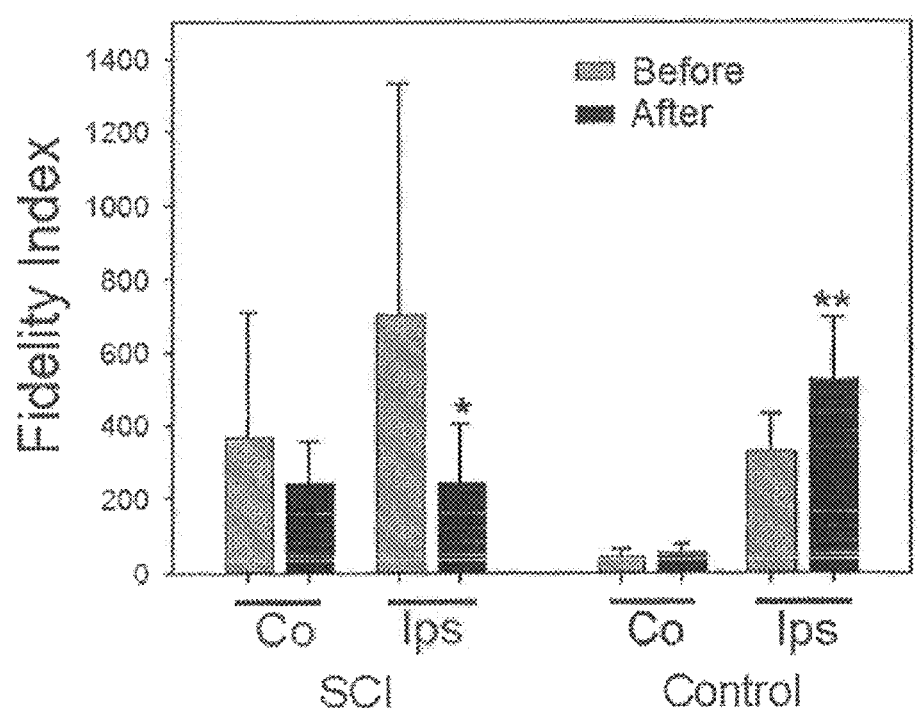
FIG. 8 is a graphical representation of a fidelity index analysis for animals with SCI and control animals.

After dCMS, SCI animals showed overall significant group reduction in FI (F=3.3, p<0.033, ANOVA) (FIG. 8). In FIG. 8, Solm-Sidak post hoc test showed reduction in FI in contralateral (average before=368.35±342.51 vs. average after=246.15±112.24), however, the difference was not statistically significant (p=0.46). The ipsilateral FI was significantly reduced after dCMS (average before=704.59±625.7 vs. average after=247.95±156.27) (p=0.011). The effect of dCMS treatment was the opposite in control animals which demonstrated overall group increase in FI after this procedure (F=31.51, p<0.001, ANOVA). FI was significantly increased after dCMS (Solm-Sidak post hoc, p<0.001) in the ipsilateral side (average before=328.53±104.83 vs. average after 526.83±169.36). There was also a trend reflecting an increase in the contralateral side (average before=48.59±17.71 vs. average after =56.15±24.19), but was not statistically significant (Solm-Sidak post hoc, p=0.89).

Comparing FI from control animals with FI from SCI animals showed a statistically significant lower index in the contralateral side of control animals (p<0.001, ANOVA, Solm-Sidak post hoc) both before and after dCMS. These results indicate that an inexcitability problem exists at the level of peripheral nerve and muscle.

10. Increase in Spinal Motoneurons Spontaneous Activity Due to dCMS.

Figure 9A:
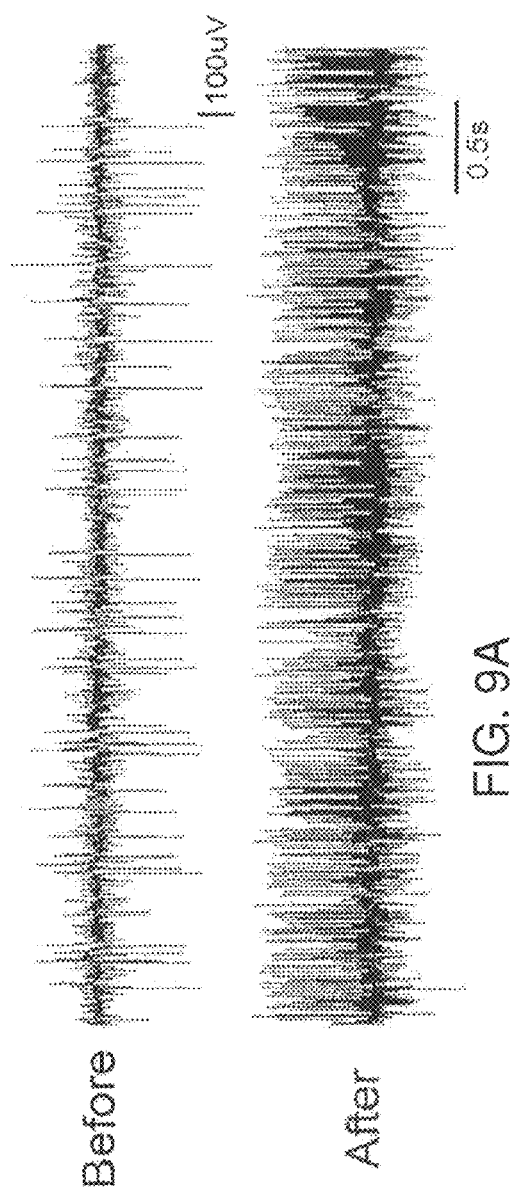
FIG. 9A shows a plot of spontaneous activity of spinal motoneurons before and after dCMS intervention.
Figure 9B:
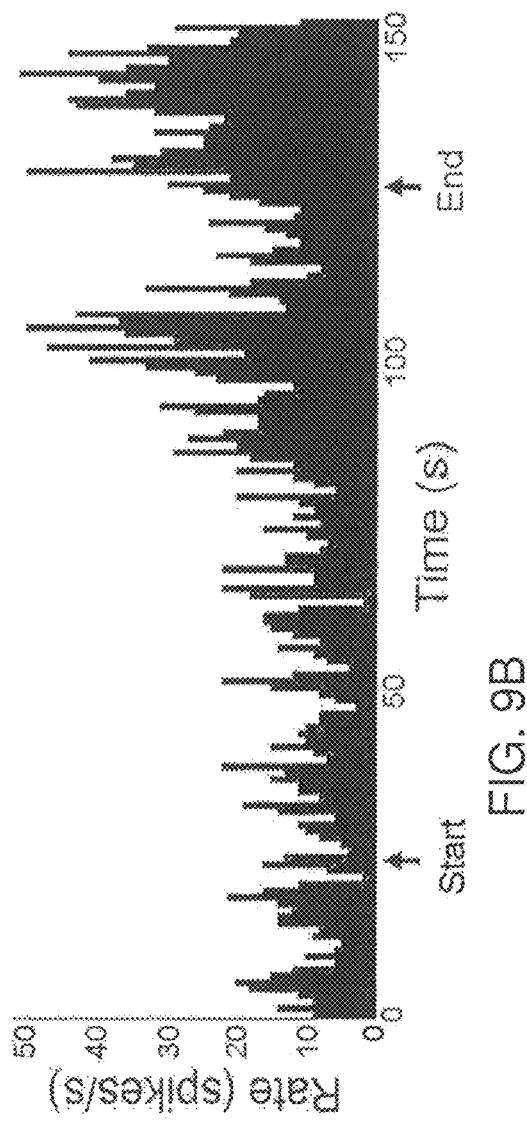
FIG. 9B is a graphical representation of firing rates during an entire experiment for an animal with SCI.
Figure 9C:
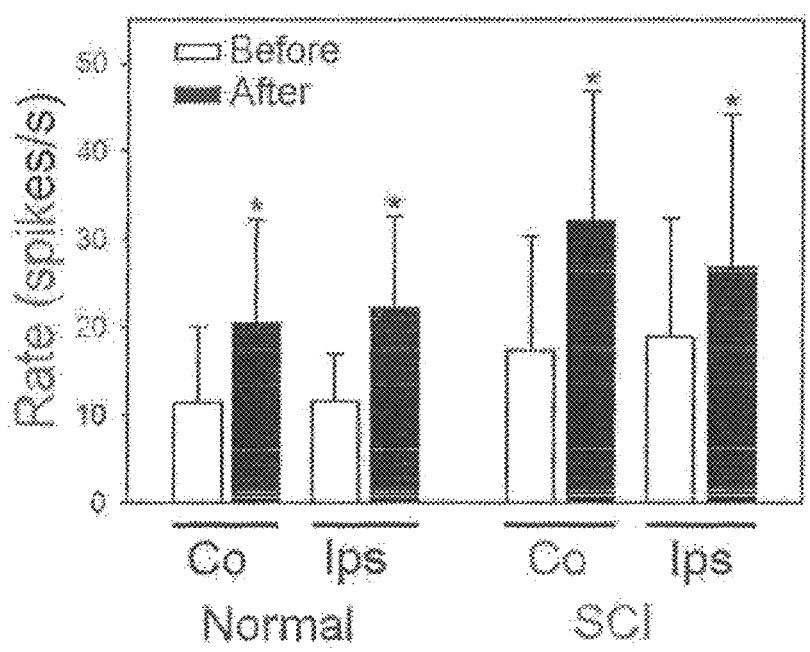
FIG. 9C is a graphical representation of firing rates before and after dCMS in control animals (contralateral and ipsilateral) and animals with SC (contralateral and ipsilateral).

Comparing the firing rate of spontaneous activity before and after dCMS intervention demonstrated significant increase in both control and SCI animals. In FIGS. 9A and 9B, a representative spontaneous activity recording from an SCI animal is shown. In SCI animals, spontaneous activity was significantly increased in the contralateral side of the spinal cord (average before=17.31±13.10 spikes/s vs. average after=32.13±14.73 spikes/s; p=0.001) (121.71±147.35%), as it did in the ipsilateral side (average before=18.85±13.64 spikes/s vs. average after=26.93±17.25; p=0.008) (percent change=54.10±32.29%). In control animals, spontaneous activity was significantly increased in the contralateral (to stimulated M1) side of the spinal cord (average before=11.40±8 65 spikes/s vs. average after=20.53±11.82 spikes/s; p=0.006) (percent change=90.10±42.53%), as it did in the ipsilateral side (average before=11.63±5.34 spikes/s vs. average after=22.18±10.35 spikes/s, p=0.01) (percent change=99.10±1.10%). One way ANOVA showed no significant difference between control and SCI animals in firing rate, although, SCI animals demonstrated higher firing rate.

11. Effects of One Point (Monopolar) Stimulation of Muscle or Cortex.

In order to determine that the effect was unique to dCMS, the influence of monopolar stimulation (maximal stimulation for 100 pulses, 1 Hz frequency) of either the muscle or the motor cortex on spinal motoneuronal response and muscle twitch peak force was examined.

As expected, muscle stimulation resulted in significant reduction in muscle twitch force (−20.28±7.02%, p<0.001, t-test) (n=5, 3 SCI and 2 control). It also resulted in a significant reduction in spinal motoneuronal responses evoked by the contralateral (to stimulated muscle) M1 test stimulation (average before=747.50±142.72 µV, vs. average after=503.14±74.78) (F=17.11, one way ANOVA, Solm-Sidak post hoc, p<0.001), however, no significant change was seen in responses recorded in the ipsilateral (to stimulated muscle) side of the spinal cord (average before 363.33±140.67 µV vs. average after=371.43±35.61, p=0.84).

In a separate group of animals (n=5, 3 SCI and 2 control), the effect of the monopolar stimulation paradigm applied only at the motor cortex on contralateral muscle twitch peak force and spinal motoneuronal response was tested. Both, the muscle twitch and motoneuron response were significantly reduced by over 50% (−53.69±4.3%, p=0.001, t-test) and almost 15% (−14.59±9.10%, p=0.003, t-test), respectively. These results indicate that one point muscle or cortical stimulation at maximal strength results in fatigue of muscle twitch force and reduction in spinal responses.

In general, the results show remarkable enhancement of the excitability of the motor pathway induced by unilateral application of dCMS. This enhancement was observed in control animals and in SCI animals that had severe locomotor impairment associated with signs of spastic syndrome. The effect was observed both in the ipsilateral and contralateral pathways. Maximal threshold of the ipsilateral cortex has been reduced. Improvement in muscle strength was accompanied by an increase in spontaneous activity and potentiation of evoked responses of the spinal motoneurons. Spinal motoneuronal responses and muscle twitches evoked by stimulation of the contralateral, non-treated M1 were significantly enhanced as well. The dCMS-induced effect persisted beyond the phase of stimulation and extended through the entire period of the experiment (60 min).

Figure 17A:
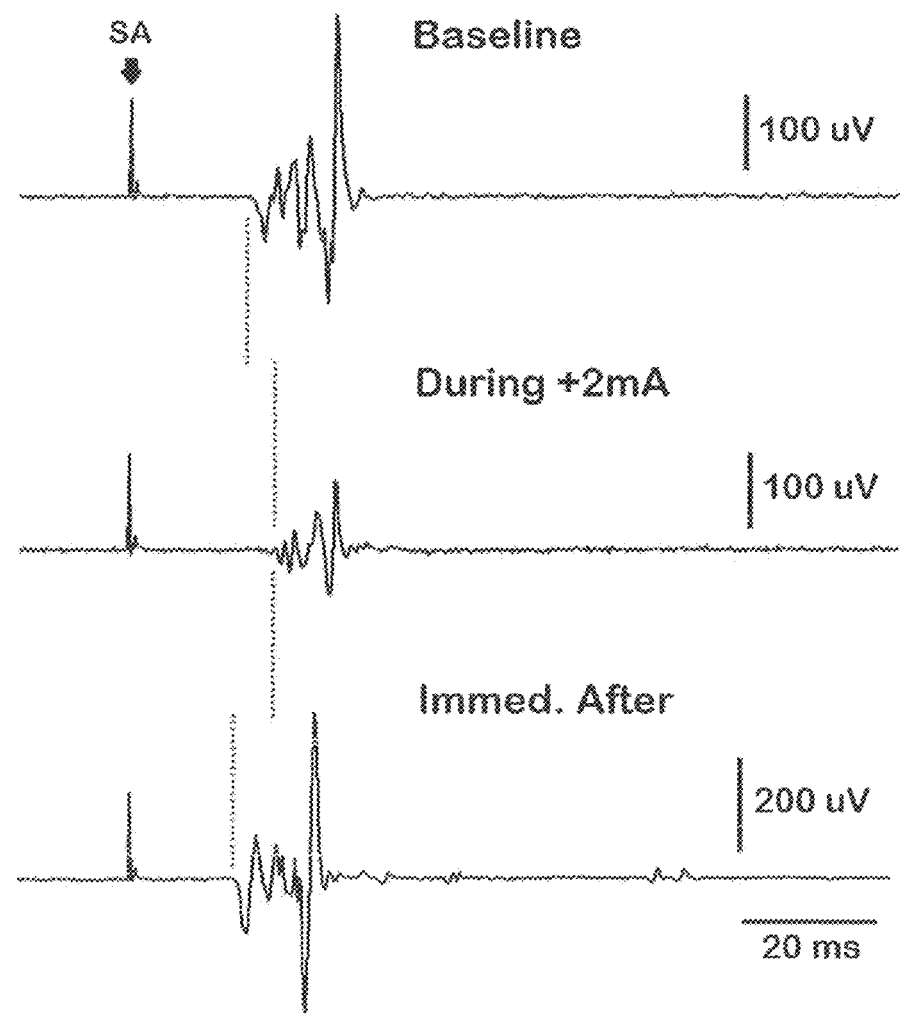
FIGS. 17A-17D demonstrate that tsDC induced changes in cortically-elicited tibial nerve potentials.
Figure 17B:
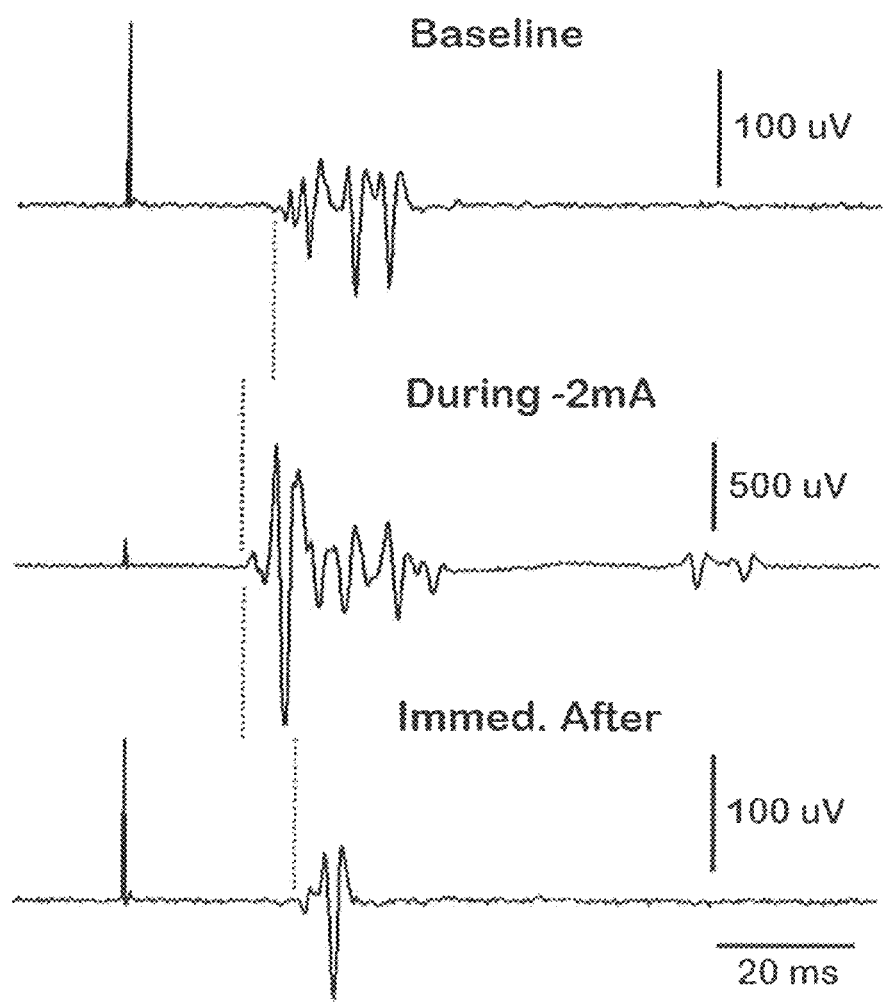
Figure 17C:
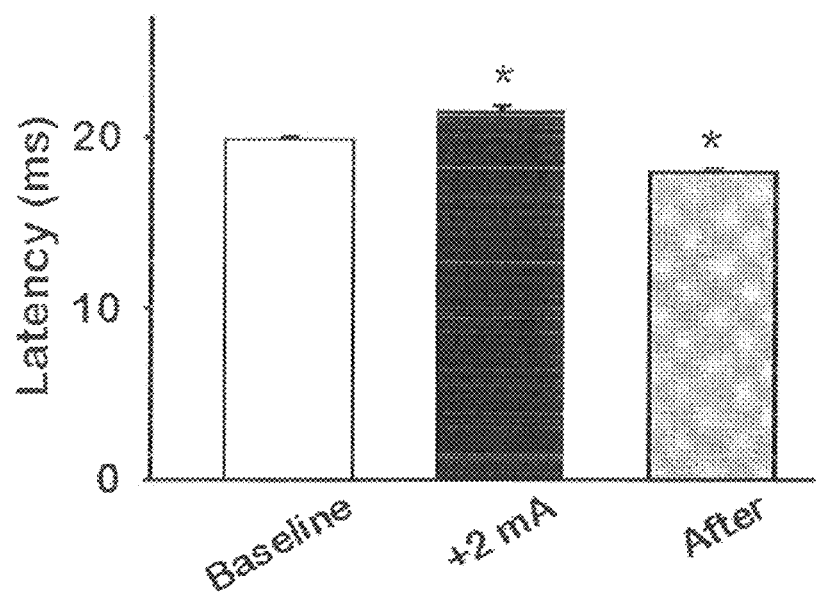
Figure 17D:
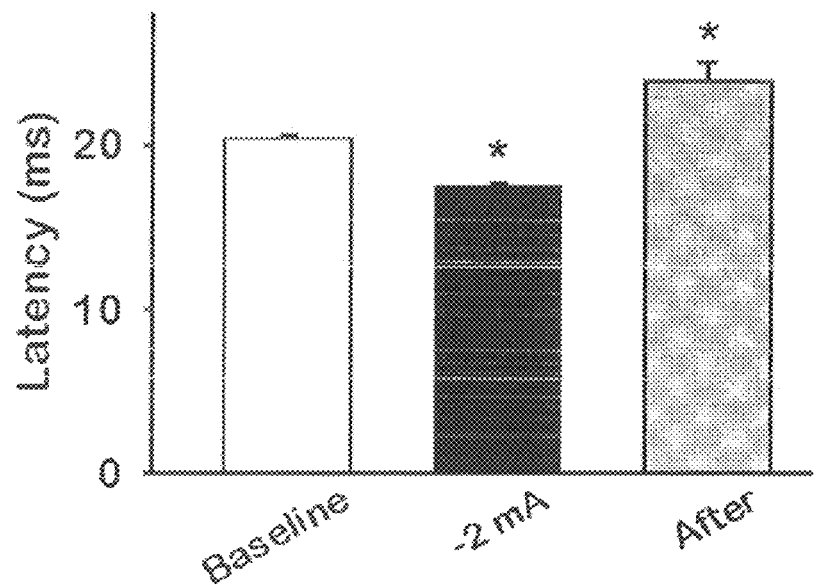

Bilateral responses to cortical stimulation have been routinely observed. They can be mediated by interhemispheric connections, ipsilateral cortico-spinal connections (5-6% of the contralateral projections), or commissural spinal neurons. As seen in FIGS. 17F and 18B, ipsilateral responses to unilateral stimulation of motor cortex evoked larger responses in SCI animals compared to controls. These results further support the idea that ipsilateral corticospinal projections are more efficient in evoking muscle contraction after SCI.

The mechanism of dCMS-induced increase in the efficiency of the motor pathway is not clear and one can only speculate what processes have been modulated. It is obvious that the potentiation in muscle force during dCMS is not like the potentiation seen after neuromuscular stimulation. See Luke R, Harris W, Bobet J, Sanelli L, Bennett D J, Tail Muscles Become Slow but Fatigable in Chronic Sacral Spinal Rats With Spasticity, J. Neurophysiol. 95:1124-1133 (2006). While neuromuscular stimulation leads to a brief potentiation of muscle force followed by a steep reduction in force, dCMS leads to a gradually proceeding increase in the amplitude of cortically-elicited muscle contraction. Since the enhancement occurred at contra- and ipsilateral sides, the locus of potentiation is most likely either spinal or supraspinal. The enhancement of cortically-elicited muscle contraction was accompanied by a reduction in maximal threshold to conical stimulation, an increase in spinal motoneuronal responses, and an increase in cortically-elicited spinal motoneuronal responses. Therefore, one can assume that improvements occurred simultaneously at several functional levels of the corticomotoneuronal pathway.

In view of the fact that the current employed in the stimulation paradigm was always positive at one end and negative at the other, the stimulation can be considered in part polarizing. In the past, the paradigm of polarizing current was used to study excitability of different parts of the nervous system. See Landau W. M., Bishop G. H., Clare M. H., Analysis of the form and distribution of cortical potentials under the influence of polarizing currents, J. Neurophysiol. 27:788-813 (1964); Gorman A. L. F., Differential patterns of activation of the pyramidal system elicited by surface anodal and cathodal cortical stimulation, J. Neuro Physiol. 29:547-64 (1965); Terzoulo C. A., Bullock T. H., Measurement of imposed voltage gradient adequate to modulate neuronal firing, Proc. Natl. Acad. Sci. USA, 42:687-694 (1956); Bindman L. J, Lippold O C. J., Redfeamn J. W. T., Long-lasting changes in the level of the electrical activity of the motor cortex produced by polarizing currents, Nature 196:584-585 (1962). In these studies, polarizing current produced potential membrane changes in which hyperpolarization occurs at cellular parts near the positive electrode and depolarization occurs near the negative electrode. Complying with this rule, for example, the situation of two polarizing electrodes on the spinal cord (one on the ventral side and the other on the dorsal side) produced changes in membrane and spike potentials of primary fibres from muscles. See Landau et al. supra.

The results of the above study suggest that the current is polarizing during the brief, steady moment of pulse duration (1 ms). Given the electrodes placement, in which negative at the muscle and positive at the cortex, the cell body of conticospinal neurons is expected to hyperpolarize and their nerve terminals depolarize. Moreover, spinal motoneurons expected to hyperpolarize at the cell body and dendrites, and depolarize at the neuromuscular junction.

According to cell topography relative to the applied electrical field, membrane potential changes are also expected to occur at intervening interneurons. These membrane changes that occur briefly during each pulse of dCMS, seem to prime corticomotoneuronal pathway for potentiation. In addition, the stimulating pulse has two more periods: rising (0.250 ms) and falling (0.250 ms). These changing periods caused a flow of current that exited from one end and entered at the other end of the corticomotoneuronal pathway. This idea is supported by the observation of stimulus artifact picked up by electrodes in the spinal cord. The current flowed throughout the entire pathway independent from the factors confounding active excitability (see introduction). This might cause activation of the corticomotoneuronal pathway at any possible excitable site/s. This will ensure eliciting spike-timing-dependent plasticity that might be one of the mechanisms that mediates the effect of the dCMS. See Dan Y, Poo M, Spiking Timing-dependent plasticity; From synapse to perception, Physiol. Rev., 86:1033-1048 (2006) for spike-timing-dependent plasticity.

In addition, the high frequency multiple spinal responses, evoked during dCMS, can, in principle, induce long-term potentiation. Because dCMS can engage a variety of neuronal mechanisms as well as non-neuronal activity, its effect might be a combination of many changes along the corticomotoneuronal pathway.

The dCMS-induced enhancement of muscle force has been observed both in control and injured animals. The mechanisms responsible for this amplification in these two groups of animals may overlap, but they do not have to be identical. Although, as discussed above the potentiating effect of dCMS could be mediated by strengthening synaptic responses, the nature and source of these changes may differ substantially in the motor pathway of control and injured animals. Axonal sprouting is probably the primary source of synaptic connections in the damaged spinal cord. See Murray et al. supra; Bareyre et al., supra; and Brus-Ramer et al. supra. However, axonal sprouting does not grant the formation of functional connections. Therefore, one of the probable mechanisms that may mediate the potentiating effect of dCMS is the refining and strengthening of the weak synaptic connections that have resulted from sprouting. Moreover, dormant connections that exist throughout the sensorimotor system may be activated and become functional after dCMS. See Brus-Ramer M., Carmel J. B., Martin J. H., Motor cortex bilateral motor representation depends on subcortical and interhemispheric interactions, J. Neurosci. 29:6196-206 (2009). Potentiating the spared normal connections could also happen after dCMS. While in control animals, potentiating of normal connections and facilitating dormant connections might be the only processes that mediate the effect of dCMS. The results show that dCMS stimulation was almost twice as effective in injured animals comparing with controls. This indicates that injured spinal cord is more prone for dCMS stimulation and posses extra mechanisms mediating the dCMS effect.

In SCI animals, even before the application of dCMS, the spinal motoneurons were responding more aggressively to cortical stimulation than controls. Nevertheless, very weak or no muscle contraction was seen (FIG. 6). This might be due to one of two mechanisms. One would be located in the spinal cord caudal to the lesion and/or the other being, the inexcitable peripheral nerves and/or the irresponsiveness of the muscle. Caudal to the lesion, the activity of the spinal motoneuron pool was probably desynchronized as a result of reorganization. Supporting this idea are the findings by Brus-Ramer and colleagues. See Brus-Ramer et al. supra. Bruce-Rarner et al. reported that chronic stimulation of corticospinal tracts resulted in preferential axonal outgrowth toward the ventral horn. This indicates that inter motoneuronal connections are dynamic processes, which may change by decentralization. Inexcitable peripheral axons were found in patients with SCI. See Lin C. S., Macefield V. G., Elam M., Wallin B. G., Engel S., Kiernan M. C., Axonal changes in spinal cord injured patients distal to the site of injury, Brain, 130:985-994 (2007). Assuming that the axons in SCI animals are in similar conditions, they could experience an action potential failure resulting in reduced muscle contraction. Muscle atrophy is always seen in animals with SCI and humans. See, for example, Ahmed Z., Wieraszko A., Combined effects of acrobatic exercise and magnetic stimulation on the functional recovery after spinal cord lesions, J. Neurotrauma, 25:1257-1269 (2008); Liu M., Bose P., Walter C. A., Thompson F. J., Vandenborne K., A longitudinal study of skeletal muscle following spinal cord injury and locomotor training, Spinal Cord, 46:488-93 (2008); Shah P. K., Stevens J. E., Gregory C. M., Pathare N. C., Jayaraman A., Bickel S. C., Bowden M., Behrman A. L., Walter G. A., Dudley G. A., Vandenborne K., Lowerextremity muscle cross-sectional area after incomplete spinal cord injury, Arch. Phys. Med. Rehabil. 87:772-778 (2006); Gordon T., Mao J., Muscle atrophy and procedures for training after spinal cord injury, Phys. Ther. 74:50-60 (1994). This might also be one of the reasons why spinal motoneurons responses were not translated adequately into muscle contraction.

The adequacy of motoneuronal responses was quantified by calculating the fidelity index, which is the ratio of spinal response to muscle twitch force. The dCMS-induced changes in fidelity index were opposite in control and injured animals. While this index has been reduced in injured animals, indicating improvement in the effectiveness of the motor pathway, it had increased in control animals suggesting lowering of the pathway effectiveness probably due to fatigue interference. Therefore, one can imply that injury to the spinal cord initiates processes which favor regeneration of the function. The dCMS procedure likely synchronizes and facilitates these processes, promoting recovery.

Before the dCMS application, the spontaneous activity of motoneurons in animals with SCI was higher than that of control animals. This and the exaggerated evoked spinal responses in animals with SCI, is consistent with the behavioral measurements that show spastic syndrome-like characteristics. The exaggerated spontaneous filing rate of spinal motoneurons is also consistent with data from motor unit firing in humans and animals after SCI and with results from intracellular recordings from sacrocaudal motoneurons that show sustained and exaggerated firing rate in animals with SCI. See, for example, Gorassini M., Bennett D. J., Kiehn O., Eken T., Hultborn H., Activation patterns of hindlimb motor units in the awake rate and their relation to motoneuron intrinsic properties. J. Neuro Physiol. 82:709-717 (1999); Thomas C. K., Ross B. H., Distinct patterns of motor unit behavior during muscle spasms in spinal cord injured subjects, J. Neuro Physiol. 77:2847-2850 (1997); Harvey J. P., Gorassini M., Bennett D. J., *The spastic rat with sacral spinal cord injury* in Animal model of movement disorders, edited by Mark LeDoux, El Sevier Academic Press, 691-697 (2005). Minutes after dCMS, motoneuronal spontaneous activity was still substantially increased. Some of these activities were coordinated, as shown in FIG. 3B, although most of the spontaneous activity was in un-modulated pattern of firing as shown in FIG. 9A. Voltage-dependent persistent inward currents (PICs) that strengthen synaptic inputs in normal behavior depend on descending brain-stem-released serotonin (5-HT) or noradrenaline. Here the increase in the spontaneous firing rate and the appearance of modulated activity in some animals after dCMS may indicate better connections with brain-stem centers.

Second Experiment

The application of dCMS on humans yielded similar results. A fourteen year old male with history of erb's palsy (right upper limb) had very weak external rotator muscles of the shoulder. The patient had no voluntary control over these muscles and could not rotate the shoulder outward. In addition, the shoulder external rotators were apparently moderately atrophied, which was determined by clinical observation. The dCMS was applied by situating the first point negative electrode on the muscles belly (the right supraspinatus and infraspinatus muscles) and the second point positive electrode on the contralateral muscles (same group). The current passed in between the two locations on opposite sides of the body, forcing the current to cross the spinal cord. It is assumed that the current follows the least resistant pathway which most likely involved right muscles (supraspinatus and infraspinatus muscles), the nerves innervating these muscles (the right suprascapular nerve from C5, C6), the motor center in the spinal cord, the nerve innervating contralateral muscles (the left suprascapular nerve from C5, C6) and finally the contralateral muscles (the left supraspinatus and infraspinatus muscles), themselves. After only 15 pulses the patient was able to rotate, with ease, the right shoulder externally, and the patient had sensation in the arm during movement. The patient's movement, which was gained during this treatment, persisted for at least four weeks.

A 14 year old female with spastic quadriplegic cerebral palsy was also treated with dCMS. She had significant muscle weakness throughout the four extremities and trunk. She also had spasticity and rigidity of most of her joints, especially the distal ones. She had extreme difficulty walking, especially climbing up and down stairs. A similar application of dCMS was performed on this patient. The locations of the electrodes were varied: 1) a positive electrode was situated on the right fibular nerve and a negative electrode on the left fibular nerve. 2) a positive electrode on the right fibular nerve and a negative electrode on the left median nerve. 3) a positive electrode on the left fibular nerve and a negative electrode on the right median nerve. 4) a positive electrode on the right median nerve and a negative electrode on the left median nerve. These configurations all allowed the current to travel across the spinal cord. After 6 sessions of the dipolar stimulation spread into two weeks (30 minutes/session), the patient could climb 17 steps independently.

The above results clearly show that dCMS is an effective method that enhances the excitability of the cortico-muscular connections in both animals and humans. Thus, the method of the present disclosure can be used in humans suffering after spinal cord injury, stroke, multiple sclerosis, and others. For example, the method of the present disclosure can be employed to strengthen or awaken any weak or dormant pathway in the nervous system as demonstrated in clinical trials.

Third Experiment

A nine-month-old child with quadriplegic paralysis due to chromosomal anomaly was treated with the same dCMS method as described in the second experiment. The child had been completely paralyzed without movement in the head, the neck, the trunk, and the upper and lower extremities. Over a course of three weeks, the child was treated in four dCMS treatment sessions that lasted 20 minutes each. After the four sessions, the child was able to make movement in all directions in the upper extremities. She could also move her fingers in all directions and hold a toy. She could hold her head up and turn her head around. Further, she was able to move her toes and lower extremities.

Fourth Experiment

Using one disc electrode situated subcutaneously over the vertebral column from T10 to L1 and another at an extravertebral location (lateral abdominal aspect), the effects of anodal tsDC (a-tsDC) or cathodal tsDC (c-tsDC) were tested on spontaneous activity and amplitude of cortically-elicited triceps surae (TS) muscle twitches. In a different set of experiments, the effects of a-tsDC or c-tsDC combined with rCES were tested. The data below demonstrate a unique pattern of modulation of corticomotoneuronal pathway activity by tsDC.

This study aimed to test whether: 1) tsDC could modulate the spontaneous activity of spinal motoneurons in a polarity-dependent manner; 2) tsDC could modulate corticomotoneuronal transmission; and 3) repetitive cortical stimulation (rCES) could affect spinal cord responses to tsDC. Using one disc electrode situated subcutaneously over the vertebral column from T10 to L1 and another at an extra-vertebral location (lateral abdominal aspect), the effects of anodal tsDC (a-tsDC) or cathodal tsDC (c-tsDC) were tested on spontaneous activity and amplitude of cortically-elicited triceps surae (TS) muscle twitches.

Methods

Animals

Experiments were carried out in accordance with NIH guidelines for the care and use of laboratory animals. Protocols were approved by the College of Staten Island IACUC. Adult CD-1 mice (n=31) were used for this study. Animals were housed under a 12-h light-dark cycle with free access to food and water.

Surgical Procedure

Animals were anesthetized using ketamine/xylazine (90/10 mg/kg, i.p.), which has been reported to preserve corticospinal evoked potential. Anesthesia was kept at this level using supplemental dosages (~5% of the original dose) as needed, and animals were kept warm throughout the procedure by a lamp.

The skin covering the two hindlimbs, thoracic and lumbar spines, and the skull was removed. On one side, TS muscle was carefully separated from the surrounding tissue, taking care to preserve the blood supply and nerves. The tendon of each of TS muscle was threaded with a hook-shaped 0-3 surgical silk, which was then connected to force transducers. Tissue surrounding the distal part of the sciatic nerve was removed. Both the sciatic nerve and TS muscle were soaked in warm mineral oil.

A craniotomy was performed to unilaterally expose the primary motor cortex (M1; usually on the right side) of the hindlimb muscles, which is located between 0 to −1 mm from bregma and 0 to 1 mm from the midline. The dura was left intact. The exposed motor cortical area was explored with a stimulating electrode to locate the motor point from which the strongest contraction of the contralateral TS muscle was obtained with the weakest stimulus.

Electrodes

An active tsDC electrode (0.8 mm2) was situated over T10-T13; the reference electrode (Ref) was situated subcutaneously over the lateral aspect of the abdominal muscles. The surrounding tissue was removed from the sciatic nerve and TS muscle, and the TS muscle was connected to force transducers. A recording microelectrode (R) was inserted into the tibial nerve. A concentric stimulating electrode (S) was placed over the contralateral motor cortex. The spinal column and skull were rigidly supported using a clamping system (not shown).

DC was induced through a gold surface electrode (0.8 cm2; Grass Technologies, West Warwick, R.I., USA) situated over the vertebral column from T10-L1. A similar reference electrode (0.8 cm2) was situated over the lateral aspect of the abdominal muscles, as shown in FIG. 12. A layer of salt-free electrode gel (Parker Laboratories, Inc., Fairfield, N.J., USA) was applied between the electrodes and the tissue. Cortical stimulation was induced by a concentric electrode (shaft diameter, 500 μm; tip, 125 μm; FHC Inc., Bowdoinham, Me., USA), which was placed over the motor cortex presentational field of the TS muscle. Extracellular recordings were made from the TS branch of the sciatic nerve with pure iridium microelectrodes (shaft diameter, 180 μm; tip, 1-2 μm; resistance, 5.0 MΩ; WPI, Sarasota, Fla., USA). Tibial nerve potentials were recorded from the same location (about 3 mm from the TS muscle) in all animals. The proper location was confirmed by penetration-elicited motor nerve spikes, which were correlated with muscle twitches.

Muscle Force Recording

The hindlimb and the proximal end of the tail were rigidly fixed to the base of the apparatus. The knee was also fixed to the base to prevent any movements from being transmitted between the stimulated muscles and the body. The tendon of the TS muscle was attached to force displacement transducers (FT10, Grass Technologies), and the muscle length was adjusted to obtain the strongest twitch force (optimal length). The head was fixed in a custom-made clamping system. Animals were kept warm during the experiment with radiant heat.

Data Acquisition

Extracellular activity was passed through a standard head stage, amplified (Neuro Amp EX, ADInstruments, Inc., Colorado Springs, Colo., USA), filtered (bandpass, 100 Hz to 5 KHz), digitized at 4 KHz, and stored in the computer for further processing. A power lab data acquisition system and LabChart 7 software (ADInstruments, Inc.) were used to acquire and analyze the data.

Polarization and Stimulation Protocols

DC was delivered by a battery-driven constant current stimulator (North Coast Medical, Inc., Morgan Hill, Calif., USA). A pie-test of cortical stimulation consisting of 10 pulses delivered at 1 Hz (intensity, 5.5 mA; pulse duration, 1 ms) was used to elicit TS muscle twitches. The intensity of anodal tsDC was increased in 30-s steps (0.5, 1, 1.5, 2, 2.5, and 3 mA) over a total duration of 3 min. Thus, the maximal current density was 3.75 A/m2 (0.003 A/0.008 m2). To avoid a stimulation break effect, the current intensity was ramped for 10 s. During each tsDC step, a test (identical to the pre-test) was conducted; this test was repeated immediately (about 10 s) after termination of tsDC, and then again 5 and 20 min later. To avoid complications by excitability changes resulting from current applications, each a-tsDC and c-tsDC protocol was tested in different group of animals (n=5/group).

In addition, in two different groups of animals (n=5/group), paired stimulation was delivered, consisting of rCES (5.5 mA, 1 ms, 1 Hz, 180 pulses) combined with either a-tsDC (+2 mA) or c-tsDC (−2 mA). A pre-test and three post-tests (0, 5 and 20 mill after) of cortical stimulation (5.5 mA, 1 ms, 1 Hz, 10 pulses) were also performed.

Control Experiments

To control for possible effects of conducting the testing procedure during tsDC, we performed experiments (n=3/group) in which only pre- and post-tests were conducted, but no tests were performed during tsDC stimulation. The procedure was performed identically to the procedure previously described, in which tsDC was increased in 30-s steps. In addition, to control for the possible tsDC-independent effects of rCES used in a paired stimulation protocol, we also performed experiments (n=2), in which rCES (180 pulses, 1 Hz) was performed alone.

Histological Analysis

After mice were exposed to a-tsDC (n=2) or c-tsDC (n=2), segments of spinal cord (~1 cm) located directly below the stimulating electrode were dissected for Hoechst stains to evaluate whether tsDC damaged spinal cord tissue. A similar spinal cord segment from an unstimulated control animal (n=1) was also analyzed. Tissues were kept overnight (4° C.) in 4% paraformaldehyde in 0.1 M PBS, then cryo-protected in 20% sucrose in PBS at 4° C. for 24 h. The spinal segments were freeze-mounted, cut into 30 μm sections, and placed on poly-L-lysine-coated glass slides. Sections were treated with Hoechst stain (5 µg/ml; Sigma) for 30 min. then washed with PBS four times. The sections were mounted and glass cover-slipped using mounting medium. Immunofluorescence was visualized using a Leica TCS SP2 confocal microscope with 405 and 488 nm lasers.

Injection of Glycine and GABA Blockers

Spinal cord segments (T13-L3) were exposed by laminectomy in anesthetized animals (n=2). The spinal column was clamped, and gastrocnemius muscles and sciatic nerves of both hindlimbs were exposed. The muscles were attached to force transducers, and recording microelectrodes and stimulating electrodes were situated as shown in FIG. 12. The spinal cord was injected at the level of L3-L4 with the inhibitory neurotransmitter blockers picrotoxin and strychnine (5 µM in 200 nl/2 min) using a microinjection pump (WPI, Sarasota, Fla. USA).

Calculations and Statistics

Cortically-elicited TS muscle twitches were calculated as the height of the twitch force relative to the baseline. The results of the pre-test, tests during tsDC, and post-tests were calculated as the average of 10 responses evoked at one Hz. Spike Histogram software (ADInstruments, Colorado Springs, Colo., USA) was used to discriminate and analyze extracellular spontaneous motoneuronal activity. Amplitude and frequency of spontaneous activity were measured as the average activity during a 20-s recording period before and at different points during and after stimulation. One-way ANOVA, repeated measures ANOVA, and Kruskal-Wallis one-way ANOVA on Ranks were used to test differences between the various treatment conditions. Post hoc tests (Holm-Sidak method or Dunn's Method) were then performed to compare cortically-elicited TS twitches at baseline or during paired stimulation with those post-stimulation. In addition, paired t-tests and Wilcoxon signed rank tests were used to compare the two treatment conditions. All data are reported as group means±standard error of the mean (S.E.M.). Statistical analyses were performed using SigmaPlot (SPSS, Chicago, Ill., USA) and LabChat software (ADInstruments, Inc.) with the level of significance set at $p<0.05$.

Results

Figure 13:
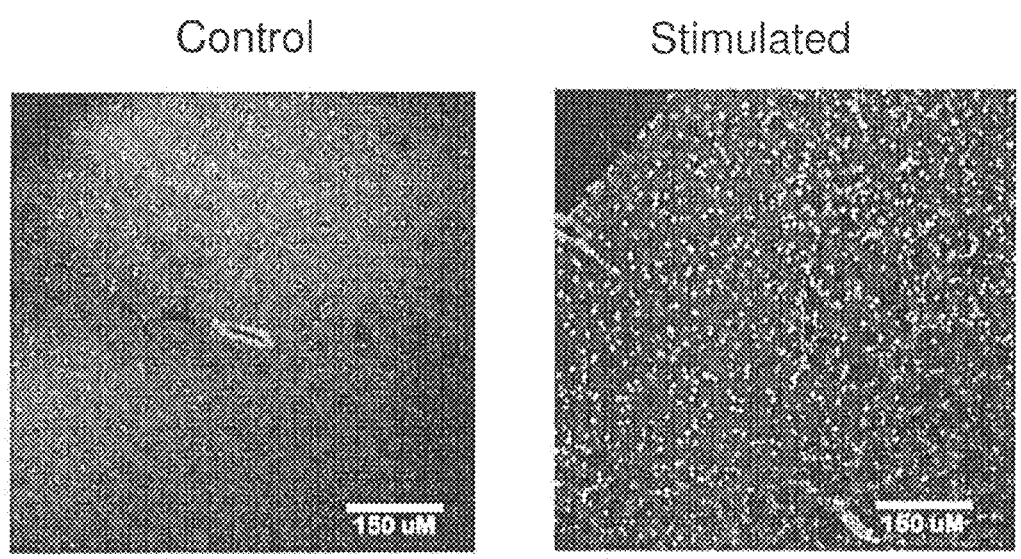
FIG. 13 shows Hoechst stains of transverse spinal cord sections from a segment (~1 cm in length) located directly under the stimulating tsDC electrode. Spinal cord sections from mice that received stimulation (right) were similar to sections from unstimulated controls (left), showing no evidence of morphological changes.

No morphological alterations were observed in the histochemical analysis of the spinal cold after a-tsDC or c-tsDC, as shown in FIG. 13.

1. tsDC Stimulation Modulates Spontaneous Activity of the Tibial Nerve.

Figures 14A, 14B:
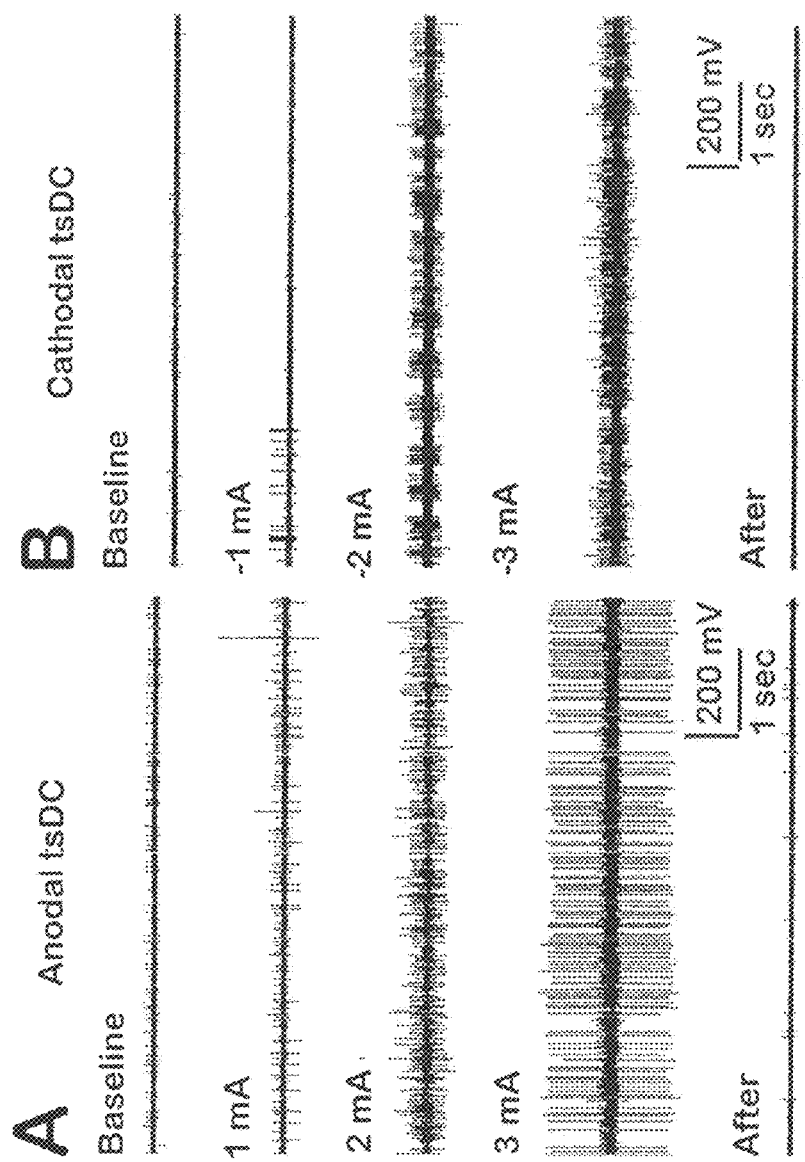
FIGS. 14A-14F illustrate that changes caused by tsDC in the frequency, amplitude, and pattern of spontaneous activity recorded from the tibial nerve.
Figure 14C:
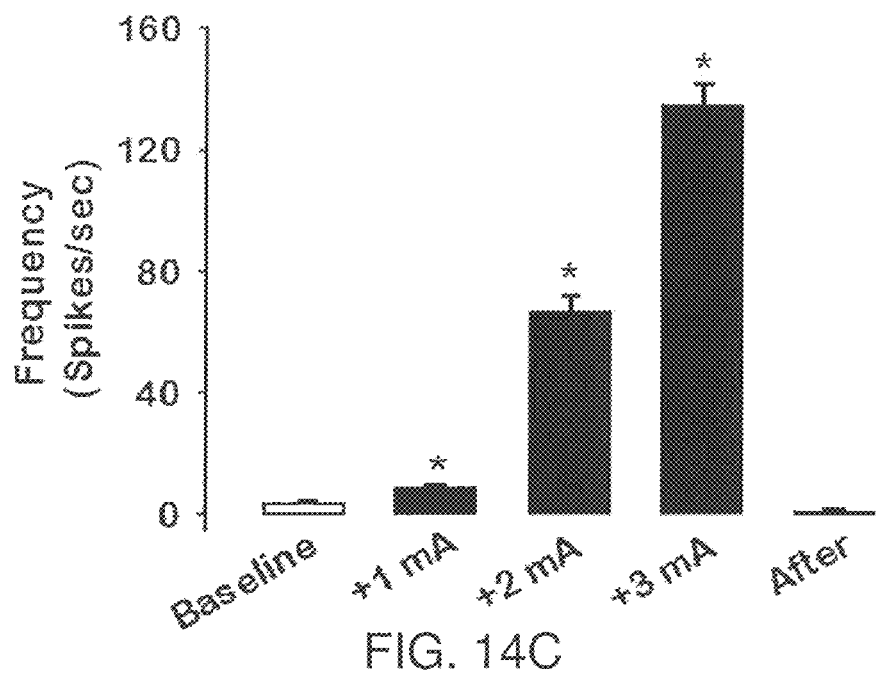
Figure 14D:
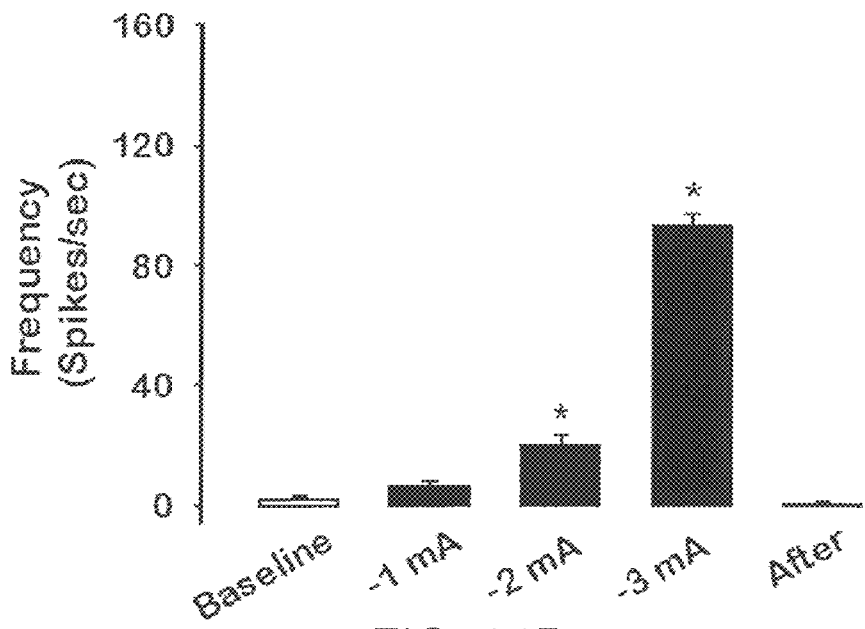

To characterize the effect of tsDC on spontaneous activity of spinal neurons, firing frequency was examined before, during and after tsDC, as shown in FIGS. 14A (a-tsDC) and B (c-tsDC). As shown in FIG. 14C, a-tsDC increased the firing frequency from a baseline of 3.3±0.3 spikes/sec to 8.5±0.5, 66.5±4.9 spikes/sec, and 134.2±6.7 spikes/sec at +1, +2, and +3 mA, respectively, yielding a significant effect of condition (repeated measures ANOVA). Immediately following the termination of a-tsDC, the spontaneous firing frequency returned to baseline levels. As shown in FIG. 14D, c-tsDC increased the firing frequency from a baseline of 2.2±0.6 spikes/sec to 6.5±3.0, 20.1±3.1 spikes/sec, and 93.1±3.8 spikes/sec at −1, −2, and −3 mA, respectively, yielding a significant effect of condition (repeated measures ANOVA). Immediately following the termination of c-tsDC, spontaneous firing frequency returned to baseline levels, was not statistically significantly different from baseline ($p>0.05$).

The a-tsDC effect on spontaneous firing frequency was significantly greater than that of c-tsDC (Kruskal-Wallis ANOVA). Post hoc tests revealed that all three a-tsDC intensity steps induced significantly higher changes in the frequency of spontaneous activity compared to the changes induced by corresponding intensities of c-tsDC ($p<0.05$).

Figure 14E:
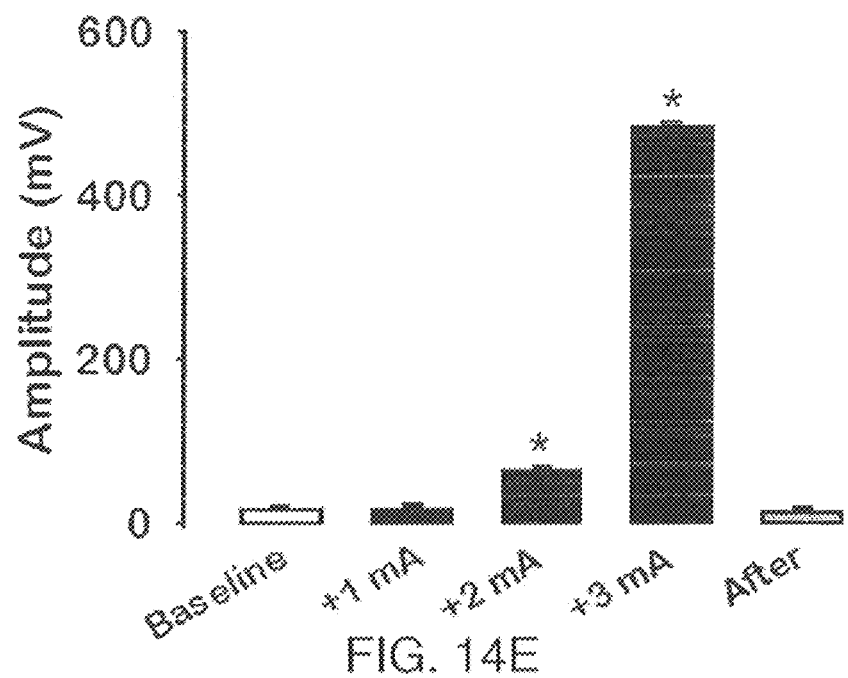
Figure 14F:
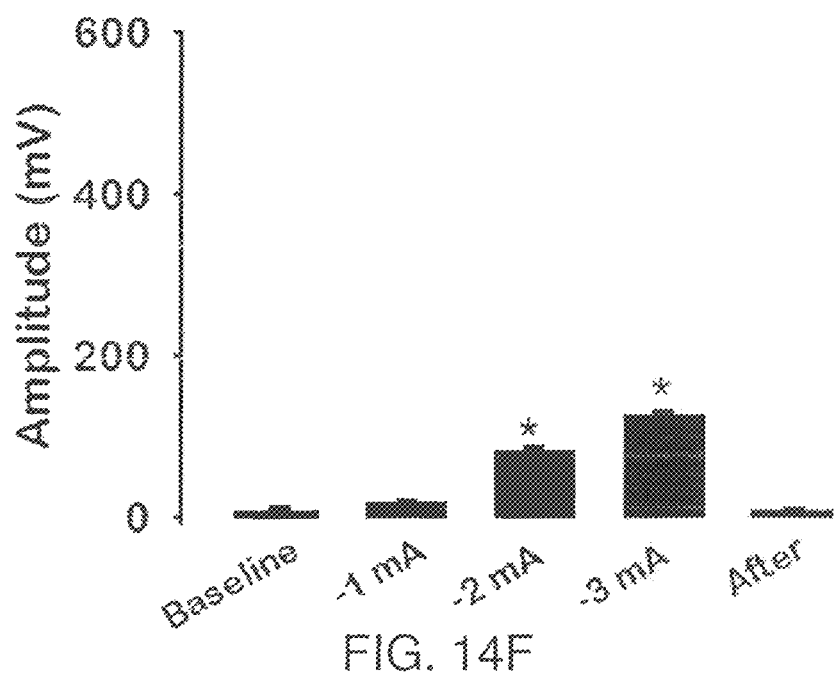

Changes in spike amplitude recorded during different intensities and polarities of tsDC were recorded across conditions (at baseline, at each intensity step, and after tsDC was terminated). Repeated measures ANOVA showed a significant overall effect of condition on the amplitude of activity recorded during baseline (16.8±0.3 mV), which increased during a-tsDC steps (step of +1=16.7±0.5 mV; step of +2=63.2 mV; step of +3=484.2±3.5 mV, then decreased after termination (11.9±0.7 mV), as shown in FIG. 14E. Subsequent post hoc tests showed that spike amplitude of activity recorded during intensity steps +2 mA and +3 mA were significantly higher than baseline activity ($p<0.05$). Repeated measures ANOVA also showed a significant overall difference in the amplitude of activity recorded at baseline (7.0±0.3 mV), during c-tsDC (step of −1=17.3±1.5 mV; step of −2=80.4±2.2 mV; step −3=123.7±4.3 mV), and after termination (5.6±0.29 mV), as shown in FIG. 14F. Subsequent post hoc tests showed that the amplitude of activity recorded during steps of −2 mA and −3 mA was significantly higher than baseline ($p<0.05$).

These findings suggest that a higher intensity of tsDC can recruit more spinal neurons or potentially more classes of spinal neurons. Furthermore, the differences between amplitudes of activity recorded during a-tsDC of +2 mA and c-tsDC of −2 mA and between a-tsDC of +3 mA and c-tsDC of −3 mA were statistically significant (t tests, p's<0.001). Overall, these findings indicate that a-tsDC and c-tsDC affect spinal neuron excitability through different mechanisms.

Figure 15A:
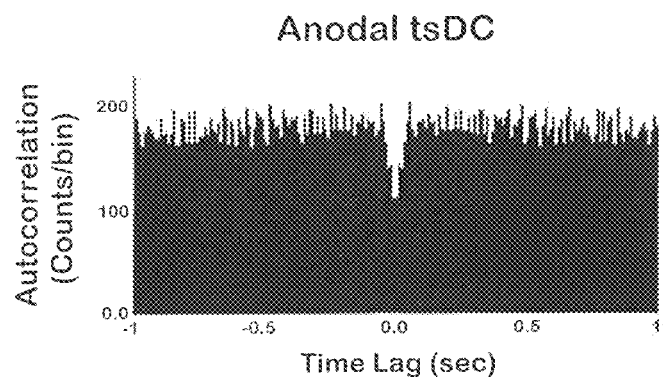
FIGS. 15A-15C show that cathodal stimulation may access rhythm-generating circuitry in the spinal cord.
Figure 15B:
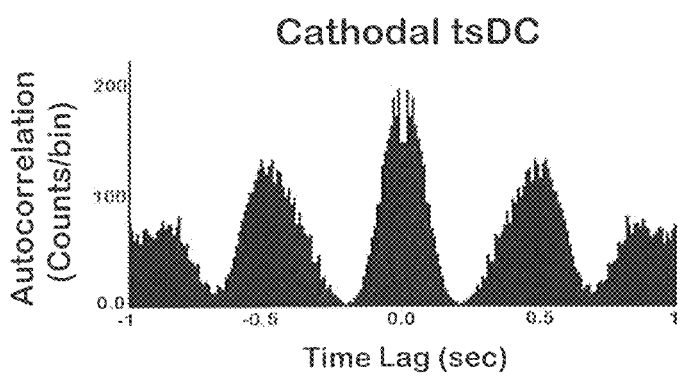
Figure 15C:
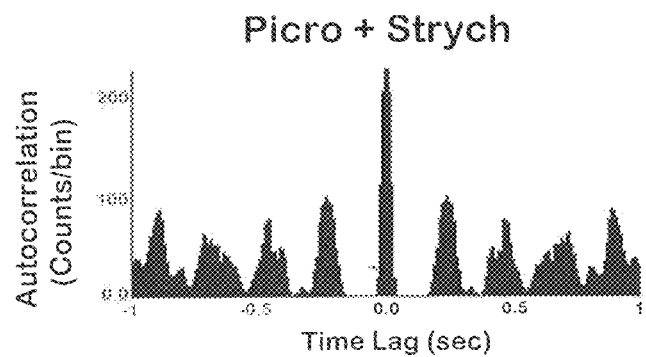

To further investigate the differential effects of a-tsDC and c-tsDC on spontaneous activity, we generated autocorrelograms for activity induced by these two conditions, as well as by injection of glycine and GABA receptor blockers. The results show tonic activity with no bursting or oscillation during a-tsDC, as shown in FIG. 15A. Conversely, c-tsDC induced bursting, as well as oscillatory activity, as shown in FIG. 15B. Similar to c-tsDC, glycine and GABA receptor blockers induced bursting and oscillatory activity, as shown in FIG. 15C. This similarity indicates that c-tsDC and glycine and GABA receptor blockers may share a mechanism of effect, which involves rhythmic-generating circuitry in the spinal cord.

2. tsDC Modulated Cortically-Elicited TS Twitches

Figure 16A:
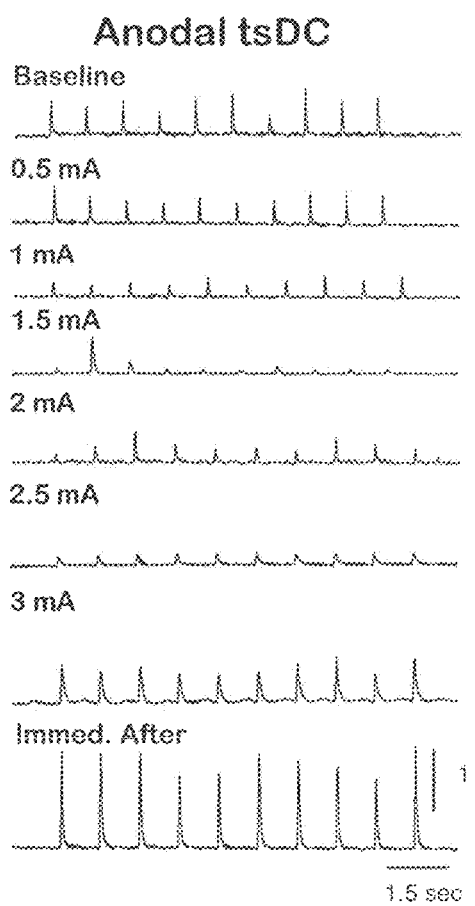
FIGS. 16A-16D illustrate that a-tsDC and c-tsDC differently modulated cortically-elicited TS twitches.
Figure 16B:
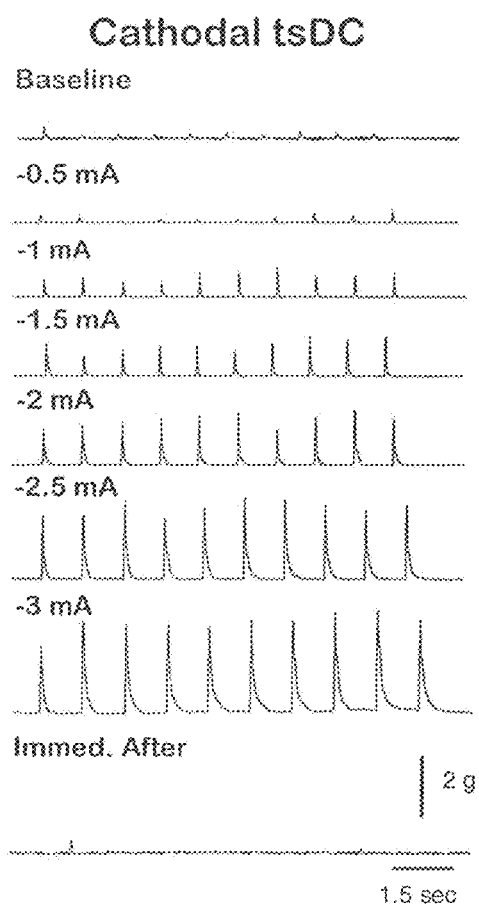
Figure 16C:
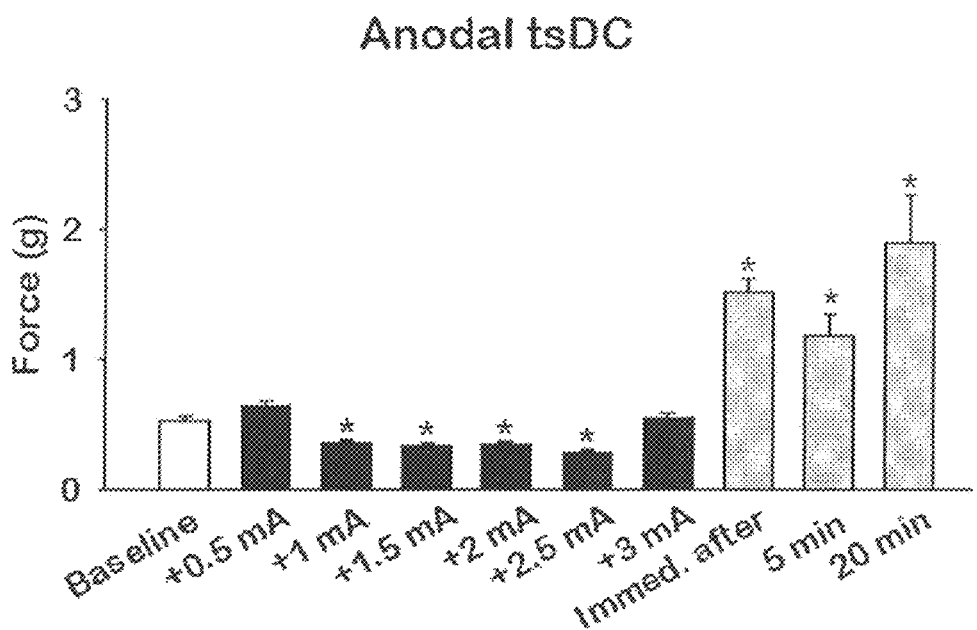

To address whether tsDC could modulate cortically-elicited TS twitches in an intensity- and polarity-dependent manner, TS twitches were elicited by stimulating the motor cortex before stimulation, at five intensity steps during tsDC, and after stimulation (at 0, 5, and 20 min). Repeated measures ANOVA, combined with post hoc tests, showed that a-tsDC affects the ability of the motor cortex to elicit TS twitches ($p<0.001$). Examples are shown in FIG. 16A. As shown in FIG. 16C, the baseline average of TS twitch peak force was 0.52±0.04 g, which was depressed to 0.35±0.02 g, 0.32±0.01 g, 0.34±0.02 g, and 0.28±0.01 g at intensities of +1 mA, +1.5 m, +2 mA, and +2.5 mA, respectively. In contrast, immediately after termination of a-tsDC, cortically-elicited TS twitches were significantly improved (1.51±0.12 g), and this improvement persisted at 5 min (1.20±0.15 g), and at 20 min (1.9±0 38) after a-tsDC.

In the a-tsDC group, there was a main effect of group (F=19.60, $p<0.001$, repeated measures ANOVA), and post hocs showed that TS twitches were significantly weaker during intensities 1 to 2.5 mA and were significantly stronger at all three time points after a-tsDC, compared to baseline. In the c-tsDC group, there was also a main effect of group (F=489.60, p<0.001, repeated measures ANOVA), and post hocs showed that TS twitches were significantly stronger during intensities −1 to −3 mA and significantly weaker afterwards, compared to baseline. Error bars represent S.E.M. *p<0.05 relative to baseline.

Figure 16D:
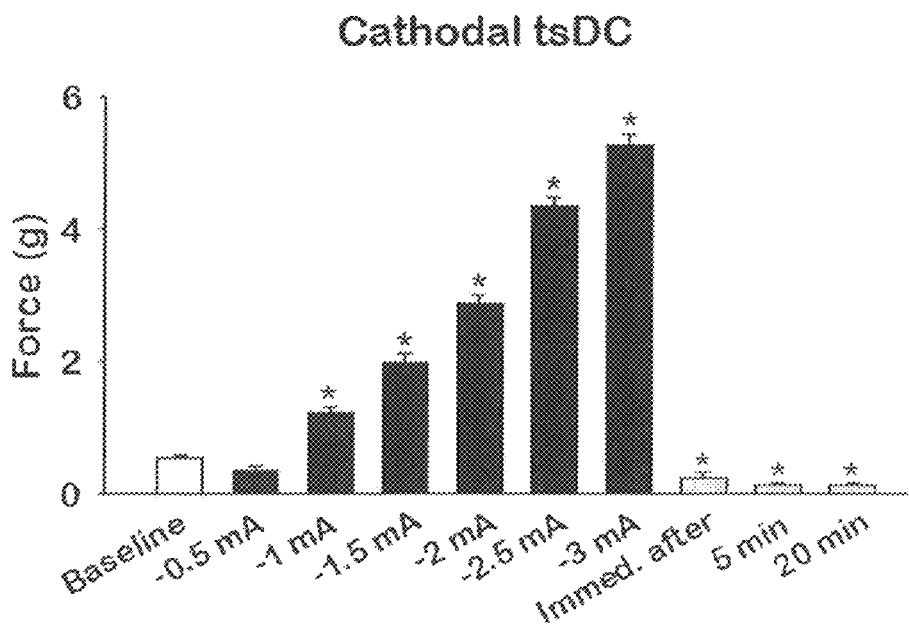

Compared to a-tsDC, the application of c-tsDC had an opposite effect on cortically-elicited twitches. Repeated measures ANOVA, combined with post hoc tests, showed a significant enhancement of cortically-elicited TS twitches during c-tsDC and depression after c-tsDC. Examples are shown in FIG. 16B. As shown in FIG. 16D, the average baseline TS twitch peak force was 0.53±0.04, which was enhanced to 1.23±0.08 g, 1.98±0.13 g, 2.88±0.13 g, 4.35±0.14 g, and 5.28±0.17 g at −1 mA, −1.5 mA, −2 mA, −2.5 mA, and −3 mA, respectively. A depressive effect was seen after termination of c-tsDC with a peak force of 0.23±0.10 g, 0.12±0.12 g, and 0.12±0.012 g at 0, 5, and 20 min, respectively. Taken together with the a-tsDC results, these data indicate that trans-spinal application of direct current can modulate the ability of the motor cortex to elicit activity at the level of the lumbar spine. This modulation depends on the polarity and intensity of the stimulation, as well as the timing of test relative to stimulation.

3. Testing Procedure Did not Change tsDC after-Effects

To investigate a possible effect of conducting the testing procedure during a-tsDC or c-tsDC, we repeated these experiments (n=3/group) with only pre- and post-tests, but no tests during the tsDC stimulation. For a-tsDC, there was no significant difference between conditions that included or excluded testing during the a-tsDC stimulation (H=5.3, p=0.06, Kruskal-Wallis ANOVA). In conditions with and without testing during stimulation, a-tsDC induced immediate improvement of TS twitches (301.14±49.33% vs. 366.9±46.9%), which persisted after 5 min (229.59±66.03% vs. 325.9±170.14%), and 20 min (387.87±117.13% vs. 299.6±137.57%). Similarly, there was no effect of the testing procedure on the c-tsDC depressive after-effect (H=5.3, p>0.05, Kruskal-Wallis ANOVA). In conditions with and without testing during stimulation, c-tsDC depressed cortically-elicited TS twitches immediately (33.48±6.40% vs. 17.65±6.40%), after 5 mm (21.24±3.8% vs. 25.45±2.98%), and after 20 min (23.95±3.44% vs. 25.35±3.0%). These results confirm that the testing procedure used in this study had no effect on the after-effects induced by a-tsDC or c-tsDC.

4. Effects of a-tsDC and c-tsDC on Latency of Cortically-Elicited Tibial Nerve Potentials Latency of cortically-elicited tibial nerve potentials was measured before, during, and after a-tsDC and c-tsDC. Only latencies measured at a-tsDC of +2 mA and c-tsDC of −2 mA are presented because no differences were found between latencies at these intensities and those at other intensities that caused significant increases in TS twitches. However, the mean latency was calculated based on measurements at all time points following tsDC. For a-tsDC, Kruskal-Wallis ANOVA showed a significant effect of time (baseline, during, and after stimulation), as shown in FIG. 17A. Post hoc tests revealed that the latency of cortically-elicited tibial nerve potentials was significantly longer during +42 mA stimulation (21.5±0.34 ms) and shorter after termination (17.92±0.21 ms) relative to baseline (19.82±0.17 ms). Similarly, for c-tsDC application, Kruskal-Wallis ANOVA showed a significant effect of time. Post hoc tests revealed that the latency of cortically-elicited tibial nerve potentials was significantly shorter during −2 mA stimulation (17.42±0.22 ms) and longer after termination (23.90±1.19 ms) relative to baseline (20.33±0.19 ms).

Taken together, these data indicate that tsDC affects the excitability of spinal neurons in a way that changes their ability to respond to the motor cortex. Thus, changes in latency may be due to redirection of the intra-spinal pathway to a faster or slower route depending on the number of synapses or simply due to changes in the recruitment pattern of spinal neurons.

5. Paired rCES and tsDC Stimulation

Figure 18A:
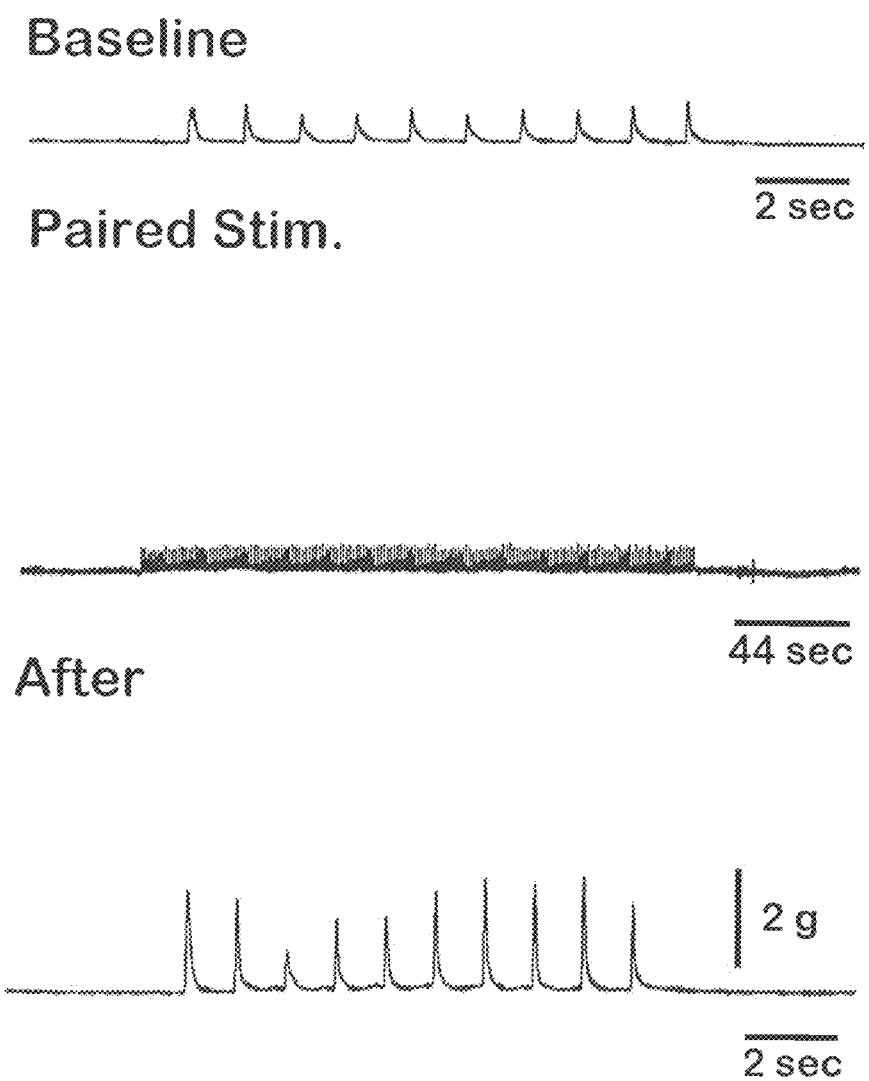
FIGS. 18A-18D illustrate the effect of paired tsDC and repetitive cortical stimulation (rCES) on cortically-elicited TS twitches. Representative recordings of TS twitches before stimulation (baseline), during stimulation, and after stimulation are shown for a-tsDC (+2 mA) paired with rCES in FIG. 18A and c-tsDC (−2 mA) paired with rCES in FIG. 18B. rCES was adjusted to give the maximal response (−5.5 mA) and was delivered at 1 Hz for 3 min. Both a-tsDC paired with rCES in FIG. 18C and c-tsDC paired with rCES in FIG. 18D significantly improved cortically-elicited TS twitches compared to baseline. Error bars represent S.E.M. *p<0.001 compared to baseline, Wilcoxon Signed Rank Test
Figure 18B:
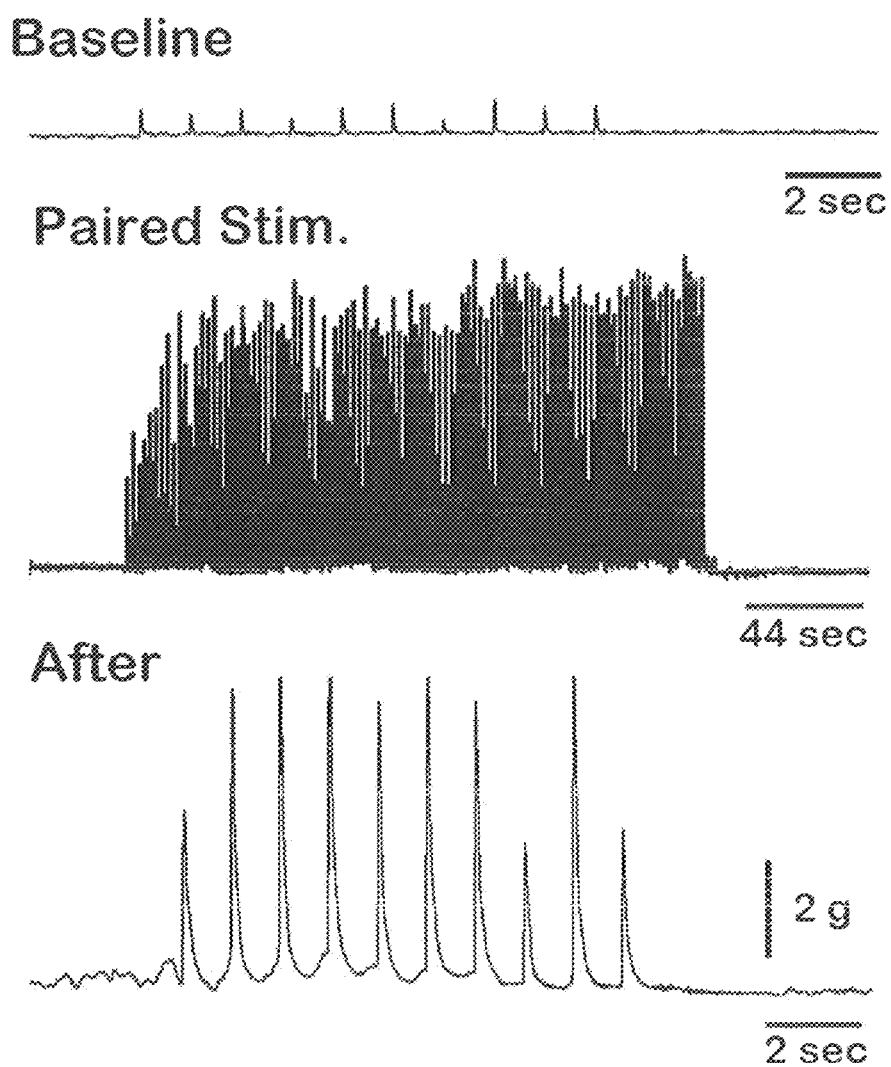
Figure 18C:
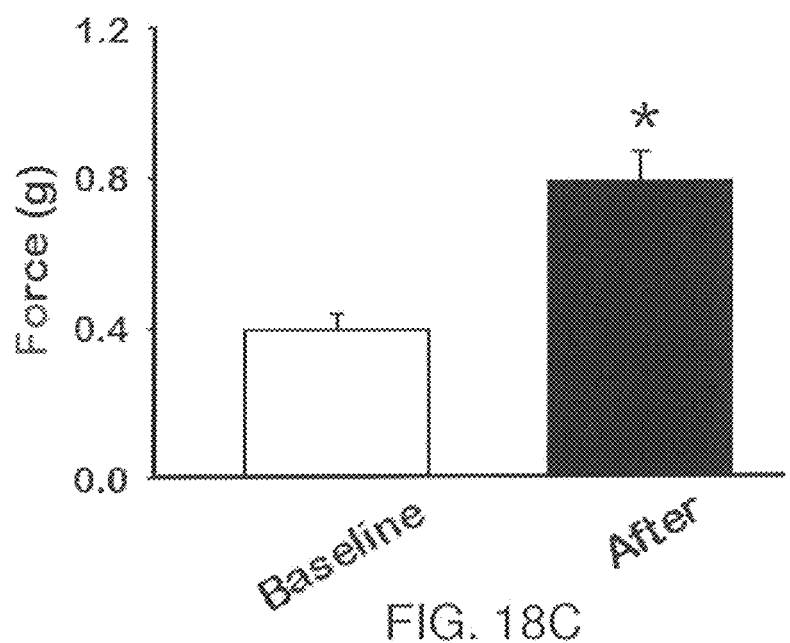
Figure 18D:
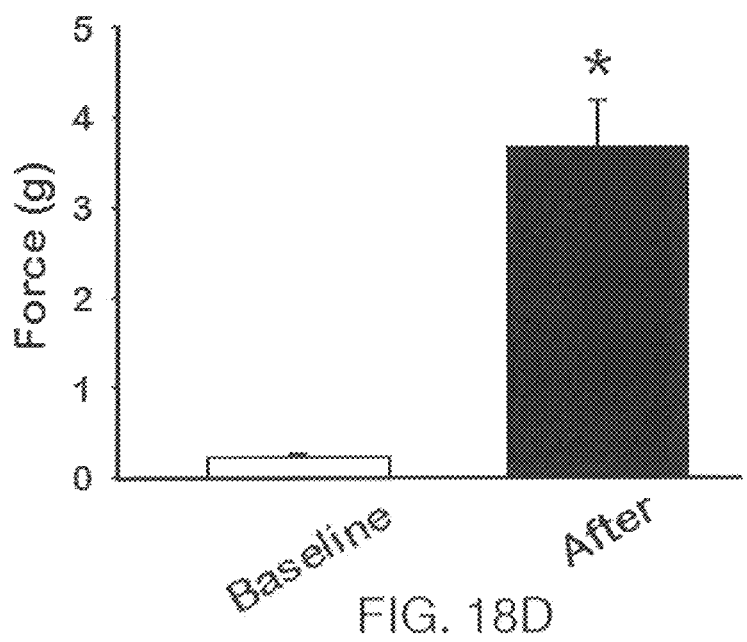

The motor cortex was stimulated for 3 min (180 pulses, 1 Hz, maximal intensity ∼5.5 mA) during either a-tsDC (+2 mA) or c-tsDC (−2 mA), as shown in FIGS. 18A and 18B. Paired rCES and a-tsDC was associated with a significant improvement in cortically-elicited TS twitches after termination of stimulation (0.80±0.10 g) compared to baseline (0.39±0.05 g) (p<0.001), as shown in FIG. 18C. Notably, paired rCES and c-tsDC showed a similar improvement after termination (3.67±0.51 g) compared to baseline (0.21±0.51 g) (p<0.001), as shown in FIG. 18D. Improvement following those two different stimulation paradigms persisted with no notable change immediately, at 5 min and at 20 min after termination. Thus, results presented after termination represent the average of these three time points. The effect of rCES alone was tested in separate group of animals (n=2), and no change was found after termination compared to baseline (t test, p>0.05) (data not shown).

A total of four stimulation paradigms used in the current experiment affected cortically-elicited TS contraction: a-tsDC, c-tsDC, a-tsDC with rCES, and c-tsDC with rCES. Kruskal-Wallis ANOVA showed a significant effect of condition (H=66.97, p<0.001). Multiple comparisons showed that paired c-tsDC and rCES was more effective than all other paradigms (2287.07±342.49%) (p<0.05), especially for reversing the depressive effect seen after c-tsDC (33.66±9.82%). Paired a-tsDC and rCES showed no significant difference (252.88±30.79%) compared to a-tsDC alone (329.18±38.79%) (p>0.05). These findings indicate that cortical activity had a strong influence on c-tsDC after-effects, however, it had no influence on a-tsDC after-effects.

Discussion

Histological analysis demonstrated no harmful morphological effects of the tsDC parameters used in the present study. The maximal current density used was 3.75 A/m$^2$ for a duration of 3 min, which is much lower than the range typically used in tats and mice as known in the art. In this study, spinal cord stimulation differed from cranial stimulation in three respects: (1) the distance from the electrode surface to the ventral aspect of the spinal cord was ∼7 mm, as opposed to the distance to the cranium of ∼0.3 mm; (2) bone, muscle and fat tissue was present between the electrode and spinal cord, while only bone was present at the cranium; and (3) the volume of the conductor surrounding the target tissue was much larger in the spinal cord than in the brain, potentially deforming the current and reducing its density.

Both a- and c-tsDC markedly increased the frequency and amplitude of spontaneous tibial nerve activity in an intensity-dependent fashion. Interestingly, a-tsDC was more effective than c-tsDC in increasing firing frequency and recruiting units with larger amplitude. These results are in agreement with data from a-tsDC stimulation of the cerebral cortex, hippocampal slices, and cerebellum. The effects of c-tsDC on neuronal discharges were more complex in three respects. First, c-tsDC only caused significant changes at higher intensities (−2 and −3 mA). Second, c-tsDC did not cause firing of neurons with large spikes, but was observed in some experiments to inhibit firing of large spikes (1 mV), while increasing firing of smaller spikes. Third, as seen in FIG. 14B, c-tsDC evoked rhythmic firing. The c-tsDC-induced increase in firing rate supports previous observations in which negative currents occasionally increased firing rate. See Bindman L. J., Lippold O. C., and Redfearn J. W., The action of brief polarizing currents on the cerebral cortex of the rat (1) during current flow and (2) in the production of long-lasting after-effects, J. Physiol. 172: 369-382 (1964).

During stimulation, a-tsDC depressed cortically-elicited TS twitches, while c-tsDC markedly potentiated twitches. From immediately after termination of tsDC until at least 20 min later, cortically-elicited TS twitches were markedly potentiated after a-tsDC and depressed after c-tsDC. Moreover, while a-tsDC increased the latency of cortically-elicited tibial nerve potentials, c-tsDC decreased this latency. After a-tsDC or c-tsDC stimulation was terminated, the effect on latency was reversed.

Changes in latency were observed despite a steady intensity of cortical stimulation, suggesting that factors underlying these changes are not likely to include the switch from a cortical site of activation to a deeper location (Rothwell et al. 1994). Instead, these factors may include: (1) axonal hyperpolarization (Moore and Westerfield 1983) by c-tsDC or (2) activating preferential spinal circuits that mediate corticomotoneuronal transmission. In rodents, the corticomotoneuronal pathway has two indirect routes, a faster route mediated via reticulospinal neurons and a slower route mediated via segmental interneurons. The present findings suggest that c-tsDC may shift the pattern of excitability at the spinal cord toward the faster reticulospinal route. Interestingly, pairing a-tsDC with rCES (1 Hz) potentiated cortically-elicited TS twitches, but was not different from a-tsDC alone. Conversely, pairing c-tsDC with rCES potentiated cortically-elicited TS twitches and had the greatest effects of any stimulation condition.

The differences in the effects of a-tsDC and c-tsDC on neuronal activity suggest that the two conditions affect distinctive neuronal types through different mechanisms. The topography of spinal neurons relative to the direction of current determines the current locus and type of effect (i.e., increase or decrease in excitability). As illustrated in FIG. 19, a dorsal cathodal current should depolarize neuronal compartments closer to the electrode and hyperpolarize compartments farther from the electrode. Thus, an interneuron with its dendrites and soma at the ventral aspect of the spinal cord and its axon at the dorsal aspect would have a hyperpolarized dendritic tree and soma and a depolarized axon and nerve terminal. Such a neuron would be less responsive to synaptic activation, but would have a lower threshold to spontaneously fire an axonally-generated action potential. A spinal neuron oriented in the opposite direction would show an opposite response to cathodal stimulation. This argument is supported by the finding that motoneuron responses to dorsolateral and medial funiculus stimulation were facilitated by depolarizing currents in the dendrites and soma, but were not affected by hyperpolarizing currents, which have also been shown to occur in the hippocampus (Bikson 2004). See Delgado-Lezama R., Perrier J. F., and Hounsgaard J., Local facilitation of plateau potentials in dendrites of turtle motoneurones by synaptic activation of metabotropic receptors, J. Physiol. 515 (Pt 1): 203-207 (1999) and Bikson M., Effects of uniform extracellular DC electric fields on excitability in rat hippocampal slices in vitro, J. Physiol. 557: 175-190 (2004).

Presynaptic depolarization has been shown to decrease presynaptic nerve action potentials and EPSPs. See Hubbard J. I. and Willis W. D., The effects of depolarization of motor nerve terminals upon the release of transmitter by nerve impulses, J. Physiol. 194: 381-405 (1968); Hubbard J. I. and Willis W. D., Reduction of transmitter output by depolarization, Nature 193: 1294-1295 (1962). The decrease in the presynaptic nerve action potentials and EPSPs may play a role in depressing cortically-elicited TS twitches during a-tsDC. In addition, hyperpolarization of the soma and dendrites could depress motoneuron responses to cortical stimulation during a-tsDC. Alternative explanations could include: (1) increased numbers of refractory motor neurons due to increased spontaneous firing, or (2) preferential activation of the spinal or supraspinal inhibitory pathway.

Rhythmic activity was observed during c-tsDC but not a-tsDC, indicating that c-tsDC may have a depressive effect on spinal inhibitory interneurons. Such interneurons might be inhibited because of their topography relative to the applied electrical field. C-tsDC might hyperpolarize both excitatory and inhibitory spinal interneurons. If it is assumed that inhibitory and excitatory spinal interneurons contain different membrane channels (e.g., fewer low-voltage-activated T-type calcium channels and hyperpolarization-activated cation channels in inhibitory interneurons), then hyperpolarization would silence inhibitory interneurons, hence disinhibiting the excitatory interneurons. In contrast, in spinal rhythmogenic neurons, hyperpolarizing tsDC might activate the hyperpolarization-activated, nonselective cation current (Ih). In combination with T-type Ca channels, Ih should gradually depolarize the cell membrane to reach the threshold for an action potential, which could be another mechanism mediating c-tsDC-induced potentiation of cortically-elicited TS twitches.

Moreover, cathodal stimulation has been shown to increase the excitability of axons aligned perpendicular to the direction of current. See Ardolino G., Bossi B., Barbieri S., and Priori A., Non-synaptic mechanisms underlie the after-effects of cathodal transcutaneous direct current stimulation of the human brain, J. Physiol. 568: 653-663 (2005). Therefore, in the present study, the corticospinal tract, which passes below the cathodal electrode, would be expected to increase axonal excitability and hence spinal output. Conversely, the dendrites and soma of motoneurons would be hyperpolarized and axons would be depolarized in response to a-tsDC stimulation. Axonal depolarization at locations that affect voltage-sensitive membrane conductances could increase the firing rate and amplitude of spontaneous activity during a-tsDC.

In the spinal cord, L-type $Ca^{+2}$ channels present in motoneuron dendrites mediate the facilitatory action of depolarizing currents. However, the exact cellular mechanisms mediating DC stimulation after-effects are not clear. Notably, mechanisms mediating the depressive after-effects of cathodal DC stimulation are completely unknown. We suggest that the pattern of c-tsDC-induced polarization (e.g., pre-synaptic hyperpolarization and post-synaptic depolarization) might activate depression-mediating mechanisms, such as retrograde signaling by endocannabinoids that selectively depresses inhibitory pre-synaptic terminals.

While the invention has been described in terms of specific embodiments, it is evident in view of the foregoing description that numerous alternatives, modifications and variations will be apparent to those skilled in the art.

Accordingly, the invention is intended to encompass all such alternatives, modifications and variations which fall within the scope and spirit of the invention and the following claims.

What is claimed is:

1. A system for treatment of a neuromuscular condition of a target body part of a vertebrate being, comprising:
 a spinal stimulator having an output for delivery of a constant current stimulation current at a spinal point on a spinal column location of a vertebrate being for delivering a trans-spinal (tsDC) current stimulation between said spinal point and a distal return point across said spinal column location for innervating said spinal column location at said spinal point associated with neural activity of a target body part of the being along a cortico-muscular pathway of interest neurally extending from the cortex through said spinal point location to a target body part of the being;
 a cortical stimulator having an output for delivery of monopolar pulsed repetitive cortical stimulation (rCES) stimulation current at a motor cortex of the being on the cortico-muscular pathway at a cortex point associated with stimulation of the target body part;
 a muscle stimulator having an output for delivery of monopolar pulsed stimulation current to stimulate a target muscle location associated with the target body part on the cortico-muscular pathway; and
 a control system configured to control application of the tsDC and rCES and muscle stimulation current on the cortico-muscular pathway between the cortical stimulator and muscle location.

2. The system of claim 1 wherein the stimulation applied to the motor cortex is positive and the stimulation applied to the target muscle is negative.

3. The system of claim 2 wherein the muscle stimulator is configured to deliver negative monopolar current to stimulate the target muscle synchronously with the pulsed polarizing stimulation current.

4. The system of claim 1 wherein the cortical stimulator is configured to deliver pulsed positive monopolar current to the motor cortex synchronously with the pulsed polarizing stimulation current.

5. The system of claim 4 wherein the cortical stimulator is configured to supply repetitive stimulations of pulsed DC current.

6. The system of claim 1 wherein the spinal stimulator further includes a pair of reference electrodes with respective lead wires and a first of the pair of reference electrodes configured to be placed at a left anterior superior iliac spine and a second of the pair configured to be placed at a right anterior superior iliac spine of the being.

7. The system of claim 1 where the control system further includes a computer system to control interaction of the spinal stimulator, the cortical stimulator and the muscle stimulator.

8. The system of claim 7 wherein the cortical stimulator has the operating specifications selected from the group of Pulse Type: Constant current, Wave form: Rectangular, Pulse duration: 0.5 to 5 ms, Pulse amplitude: 1 to 15 mA, Pulse voltage: 1 to 35V, and Frequency range: 0.5 to 5Hz.

9. The system of claim 7 wherein the cortical stimulator provides up to a maximum of 5.5 mA.

10. The system of claim 7 wherein the cortical stimulator has the operating specifications including those selected from the group of: Pulse Type: Constant current, Wave form: Rectangular, Pulse duration: 0.5 to 5 ms, Pulse amplitude: 1 to 15 mA, Pulse voltage: 1 to 35V, and Frequency range: 0.5 to 5Hz.

11. The system of claim 1 wherein each of the spinal stimulator, the cortical stimulator and the muscle stimulator produces a pulsed constant current output at a respective milliamp level.

* * * * *